(12) United States Patent
Takafuji et al.

(10) Patent No.: US 7,803,380 B2
(45) Date of Patent: Sep. 28, 2010

(54) COMPOSITIONS AND METHODS FOR DIAGNOSIS AND TREATMENT OF TUMORS

(75) Inventors: Vivian Takafuji, Alexandria, VA (US); Xin Wei Wang, Rockville, MD (US)

(73) Assignee: The United States of America as represented by the Department of Health and Human Services, Washington, DC (US)

( * ) Notice: Subject to any disclaimer, the term of this patent is extended or adjusted under 35 U.S.C. 154(b) by 1 day.

(21) Appl. No.: 12/340,211

(22) Filed: Dec. 19, 2008

(65) Prior Publication Data

US 2009/0136524 A1 May 28, 2009

Related U.S. Application Data

(63) Continuation-in-part of application No. PCT/US2007/071712, filed on Jun. 20, 2007.

(60) Provisional application No. 60/805,298, filed on Jun. 20, 2006.

(51) Int. Cl.
A61K 39/38 (2006.01)
A61K 38/00 (2006.01)
(52) U.S. Cl. .................... 424/184.1; 530/300
(58) Field of Classification Search .............. 424/184.1; 530/300
See application file for complete search history.

(56) References Cited

U.S. PATENT DOCUMENTS

| 6,818,621 B2 | 11/2004 | Ashkar |
| 6,846,642 B2 | 1/2005 | Mok et al. |
| 2003/0044863 A1 | 3/2003 | Ashkar |
| 2004/0058849 A1 | 3/2004 | Sleeman et al. |
| 2004/0142865 A1 | 7/2004 | Weber |
| 2005/0054593 A1 | 3/2005 | Stromblad et al. |

FOREIGN PATENT DOCUMENTS

| EP | 1 375 518 A1 | 1/2004 |
| WO | WO 03/007794 A2 | 1/2003 |
| WO | WO 03/087766 A2 | 10/2003 |
| WO | WO 2006/043954 A1 | 4/2006 |
| WO | WO 2007/149948 A2 | 12/2007 |
| WO | WO2009052286 A1 | 4/2009 |

OTHER PUBLICATIONS

Freshney (Culture of Animal Cells, A Manual of Basic Technique, Alan R. Liss, Inc., 1983, New York, p. 4).*
Dermer (Bio/Technology, 1994, 12:320).*
Gura (Science, 1997, 278:1041-1042.).*
Accession No. AAO98254, 2003.
Accession No. AAP64039, 2003.
Accession No. AAQ71182, 2003.
Accession No. AAV20636, 2004.
Accession No. ABE20469, 2006.
Accession No. ABE20470, 2006.
Accession No. CAC16641, 2001.
Accession No. CAC16642, 2001.
Accession No. CAC16643, 2001.
Accession No. CAD26799, 2002.
Accession No. XP_517332, 2004.
Genseq Database Accession No. ADT50908, Macina et al., "Cancer Related Protein Sequence #71," 2005.
Abel et al., "The Osteopontin—CD44 Pathway is Superfluous for the Development of Autoimmune Myocarditis," *Eur. J. Immunol.* 36:494-499, 2006.
Agnihotri et al., "Osteopontin, a Novel Substrate for Matrix Metalloproteinase-3 (Stromelysin-1) and Matrix Metalloproteinase-7 (Matrilysin)," *J. Biol. Chem.* 276:28261-28267, 2001.
Bautista et al., "Inhibition of Arg-Gly-Asp (RGD)-Mediated Cell Adhesion to Osteopontin by a Monoclonal Antibody against Osteopontin," *J. Biol. Chem.* 269:23280-23285, 1994.
Bramwell et al., "Serial Plasma Osteopontin Levels Have Prognostic Value in Metastatic Breast Cancer," *Clin. Cancer Res.* 12:3337-3343, 2006.
Caers et al., "The Involvement of Osteopontin and Its Receptors in Multiple Myeloma Cell Survival, Migration and Invasion in the Murine 5T33MM Model," *Br. J. Haematol.* 132:469-477, 2006.
Dalman et al., Grant No. 1P50HL083800-01, "AAA Disease: Mechanism, Stratification and Treatment," *Computer Retrieval of Information on Scientific Projects*, 2006 (Abstract).
Denhardt et al., "Role of Osteopontin in Cellular Signaling and Toxicant Injury," *Ann. Rev. Pharmacol. Toxicol.* 41:723-749, 2001.
Gao et al., "Osteopontin-dependent CD44v6 Expression and Cell Adhesion in HepG2 Cells," *Carcinogenesis* 24:1871-1878, 2003.
Gotoh et al., "Overexpression of Osteopontin in Hepatocellular Carcinoma" *Pathol. Int.* 52:19-24, 2002.
He et al., "An Osteopontin Splice Variant Induces Anchorage Independence in Human Breast Cancer Cells," *Oncogene* 25:2192-2202, 2006.
Ishiwatari-Hayasaka et al., "Requirements for Signal Delivery Through CD44: Analysis Using CD44-Fas Chimeric Proteins," *J. Immunol.* 163:1258-1264, 1999.

(Continued)

*Primary Examiner*—Sean E Aeder
(74) *Attorney, Agent, or Firm*—Klarquist Sparkman, LLP

(57) ABSTRACT

Based on the observation of the cooperation of osteopontin (OPN) and matrixmetalloproteinase-9 (MMP-9) in the promotion of the metastatic phenotype, therapies and diagnostic assays are disclosed for the treatment of a tumor that overexpresses OPN, such as hepatocellular carcinoma (HCC), for example metastatic HCC. In one example, methods of treating a tumor include administration of an agent that reduces cellular invasion resulting from the interaction between a fragment of OPN (OPN-5kD) generated by MMP-9 cleavage and CD44 receptor. Examples of such agents include fragments of OPN-5kD and antibodies specific for OPN-5kD. Therapeutic compositions are also provided that include such agents. Also provided are methods of diagnosing or prognosing a tumor, for example by detecting expression of OPN-5kD peptide or OPN-c mRNA in a biological sample obtained from the subject. Also provided are antibodies that specifically bind OPN-5kD.

63 Claims, 9 Drawing Sheets

OTHER PUBLICATIONS

Ito et al., "An Inducible Short-Hairpin RNA Vector Against Osteopontin Reduces Metastatic Potential of Human Esophageal Squamous Cell Carcinoma In Vitro and In Vivo," *Clin. Cancer Res.* 12:1308-1316, 2006.

Kon et al., "Antibodies to Different Peptides in Osteopontin Reveal Complexities in the Various Secreted Forms," *J. Cell. Biochem.* 77:487-498, 2000.

Le, Grant No. 1R01CA118582-01, "Defining Molecular Markers for Tumor Hypoxia," *Computer Retrieval of Information on Scientific Projects*, 2006 (Abstract).

Liu et al., "Effect of Human Osteopontin on Proliferation, Transmigration and Expression of MMP-2 and MMP-9 in Osteosarcoma Cells," *Chin. Med. J. 117*:235-240, 2004.

Pan et al., "Overexpression of Osteopontin is Associated with Intrahepatic Metastasis, Early Recurrence, and Poorer Prognosis of Surgically Resected Hepatocellular Carcinoma," *Cancer* 98:119-127, 2003.

Qin and Tang, "Recent Progress in Predictive Biomarkers for Metastatic Recurrence of Human Hepatocellular Carcinoma: A Review of the Literature," *J. Cancer Res. Clin. Oncol. 130*:497-513, 2004.

Radisky and Bissell, "Matrix Metalloproteinase-Induced Genomic Instability," *Curr. Opin. Genet. Dev. 16*:45-50, 2006.

Rangaswami et al., "Osteopontin: Role in Cell Signaling and Cancer Progression," *Trends Cell. Biol. 16*:79-87, 2006.

Seth et al., "Osteopontin: An Early Marker for Alcoholic Liver Injury," *Abstract for Presentation at ISBRA 2006 World Congress on Alcohol Research*, 2006.

Takafuji et al., "An Osteopontin Fragment is Essential for Tumor Cell Invasion in Hepatocellular Carcinoma," *Oncogene* 26:6361-6371, 2007.

Tanaka et al., "Effect of Osteopontin Alleles on β-Glucan-Induced Granuloma Formation in the Mouse Liver," *Am. J. Pathol. 164*:567-575, 2004.

Tang et al., "A Decade's Studies on Metastasis of Hepatocellular Carcinoma," *J. Cancer Res. Clin. Oncol. 130*:187-196, 2004.

Thorgeirsson and Grisham, "Molecular Pathogenesis of Human Hepatocellular Carcinoma," *Nature Genet. 31*:339-346, 2002.

Wai et al., "Osteopontin Silencing by Small Interfering RNA Suppresses In Vitro and In Vivo CT26 Murine Colon Adenocarcinoma Metastasis," *Carcinogenesis 26*:741-751, 2005.

Weber et al., "Receptor-Ligand Interaction Between CD44 and Osteopontin (Eta-1)," *Science 271*:509-512, 1996.

Weber, "The Metastasis Gene Osteopontin: A Candidate Target for Cancer Therapy," *Biochim. Biophys. Acta 1552*:61-85, 2001.

Ye et al., "Predicting Hepatitis B Virus-positive Metastatic Hepatocellular Carcinomas Using Gene Expression Profiling and Supervised Machine Learning," *Nature Med.* 9:416-423, 2003.

Ye, "Research on Recurrence and Metastasis of Hepatocellular Carcinoma," *J. Gastroenterol. Heptatol. 19*:S264-S265, 2004.

Zwick et al., "Identification and Characterization of a Peptide That specifically Binds the Human, Broadly Neutralizing Anti-Human Immunodeficiency Virus Type 1 and Antibody b12," *J. Virol.* 75:6692-6699, 2001.

\* cited by examiner

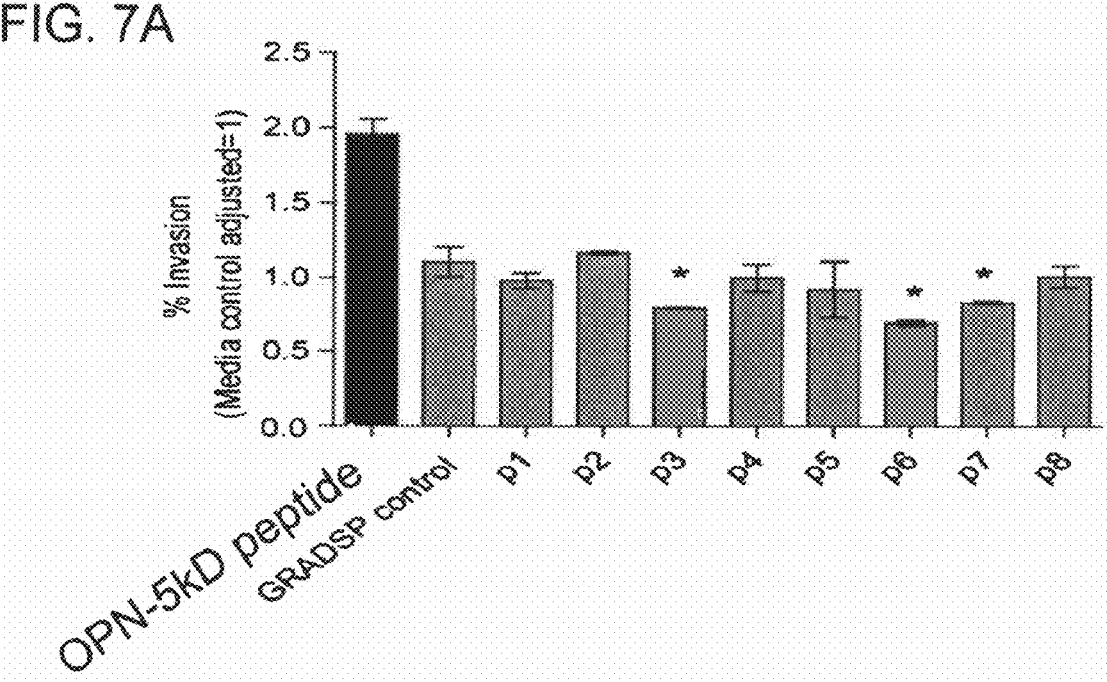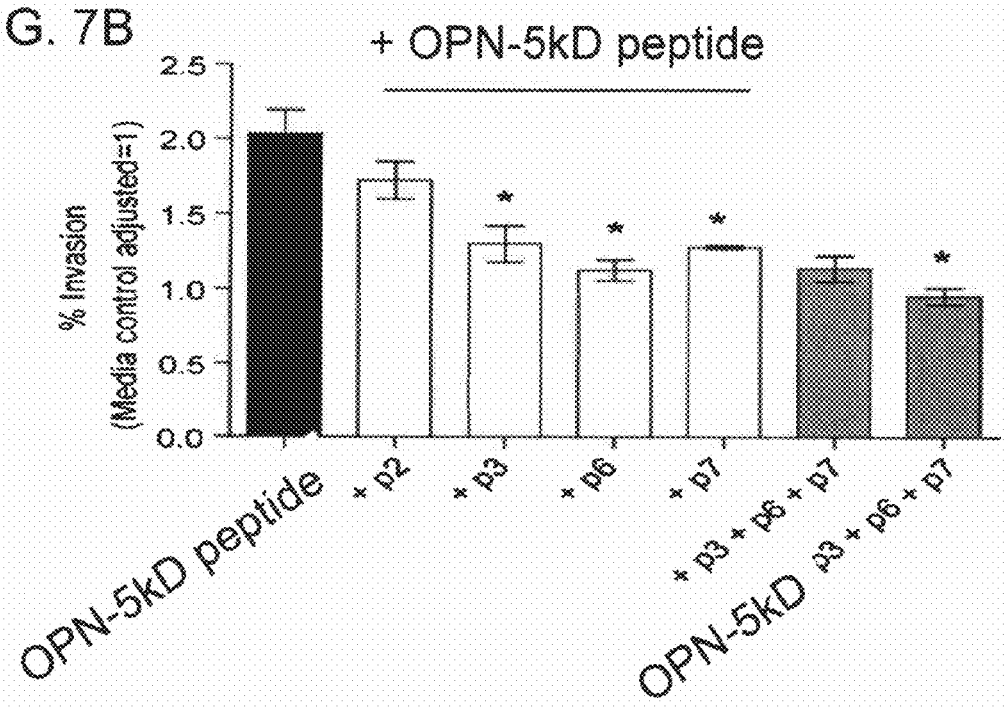

SEQUENCE LISTING

<160> NUMBER OF SEQ ID NOS: 19

<210> SEQ ID NO 1
<211> LENGTH: 1424
<212> TYPE: DNA
<213> ORGANISM: Homo sapiens

<400> SEQUENCE: 1

```
gaccagactc gtctcaggcc agttgcagcc ttctcagcca aacgccgacc aaggaaaact    60
cactaccatg agaattgcag tgatttgctt ttgcctccta ggcatcacct gtgccatacc   120
agttaaacag gctgattctg gaagttctga ggaaaagcag ctttacaaca aatacccaga   180
tgctgtggcc acatggctaa accctgaccc atctcagaag cagaatctcc tagccccaca   240
gaatgctgtg tcctctgaag aaaccaatga ctttaaacaa gagacccttc caagtaagtc   300
caacgaaagc catgaccaca tggatgatat ggatgatgaa gatgatgatg accatgtgga   360
cagccaggac tccattgact cgaacgactc tgatgatgta gatgacactg atgattctca   420
ccagtctgat gagtctcacc attctgatga atctgatgaa ctggtcactg attttcccac   480
ggacctgcca gcaaccgaag ttttcactcc agttgtcccc acagtagaca catatgatgg   540
ccgaggtgat agtgtggttt atggactgag gtcaaaatct aagaagtttc gcagacctga   600
catccagtac cctgatgcta cagacgagga catcacctca cacatggaaa gcgaggagtt   660
gaatggtgca tacaaggcca tccccgttgc ccaggacctg aacgcgcctt ctgattggga   720
cagccgtggg aaggacagtt atgaaacgag tcagctggat gaccagagtg ctgaaaccca   780
cagccacaag cagtccagat tatataagcg gaaagccaat gatgagagca atgagcattc   840
cgatgtgatt gatagtcagg aactttccaa agtcagccgt gaattccaca gccatgaatt   900
tcacagccat gaagatatgc tggttgtaga ccccaaaagt aaggaagaag ataaacacct   960
gaaatttcgt atttctcatg aattagatag tgcatcttct gaggtcaatt aaaaggagaa  1020
aaaatacaat ttctcacttt gcatttagtc aaaagaaaaa atgctttata gcaaaatgaa  1080
agagaacatg aaatgcttct ttctcagttt attggttgaa tgtgtatcta tttgagtctg  1140
gaaataacta atgtgtttga taattagttt agtttgtggc ttcatggaaa ctccctgtaa  1200
actaaaagct tcagggttat gtctatgttc attctataga agaaatgcaa actatcactg  1260
```

```
tattttaata tttgttattc tctcatgaat agaaatttat gtagaagcaa acaaaatact   1320
tttacccact taaaaagaga atataacatt ttatgtcact ataatctttt gttttttaag   1380
ttagtgtata ttttgttgtg attatctttt tgtggtgtga ataa                   1424
```

<210> SEQ ID NO 2
<211> LENGTH: 314
<212> TYPE: PRT
<213> ORGANISM: Homo sapiens

<400> SEQUENCE: 2

```
Met Arg Ile Ala Val Ile Cys Phe Cys Leu Leu Gly Ile Thr Cys Ala
1               5                   10                  15

Ile Pro Val Lys Gln Ala Asp Ser Gly Ser Ser Glu Glu Lys Gln Leu
            20                  25                  30

Tyr Asn Lys Tyr Pro Asp Ala Val Ala Thr Trp Leu Asn Pro Asp Pro
        35                  40                  45

Ser Gln Lys Gln Asn Leu Leu Ala Pro Gln Asn Ala Val Ser Ser Glu
    50                  55                  60

Glu Thr Asn Asp Phe Lys Gln Glu Thr Leu Pro Ser Lys Ser Asn Glu
65                  70                  75                  80

Ser His Asp His Met Asp Asp Met Asp Glu Asp Asp Asp His
                    85                  90                  95

Val Asp Ser Gln Asp Ser Ile Asp Ser Asn Asp Ser Asp Val Asp
                100                 105                 110

Asp Thr Asp Asp Ser His Gln Ser Asp Glu Ser His His Ser Asp Glu
            115                 120                 125

Ser Asp Glu Leu Val Thr Asp Phe Pro Thr Asp Leu Pro Ala Thr Glu
        130                 135                 140

Val Phe Thr Pro Val Val Pro Thr Val Asp Thr Tyr Asp Gly Arg Gly
145                 150                 155                 160

Asp Ser Val Val Tyr Gly Leu Arg Ser Lys Ser Lys Phe Arg Arg
                165                 170                 175

Pro Asp Ile Gln Tyr Pro Asp Ala Thr Asp Glu Asp Ile Thr Ser His
            180                 185                 190

Met Glu Ser Glu Glu Leu Asn Gly Ala Tyr Lys Ala Ile Pro Val Ala
        195                 200                 205

Gln Asp Leu Asn Ala Pro Ser Asp Trp Asp Ser Arg Gly Lys Asp Ser
    210                 215                 220

Tyr Glu Thr Ser Gln Leu Asp Asp Gln Ser Ala Glu Thr His Ser His
225                 230                 235                 240

Lys Gln Ser Arg Leu Tyr Lys Arg Lys Ala Asn Asp Glu Ser Asn Glu
                245                 250                 255

His Ser Asp Val Ile Asp Ser Gln Glu Leu Ser Lys Val Ser Arg Glu
            260                 265                 270

Phe His Ser His Glu Phe His Ser His Glu Asp Met Leu Val Val Asp
        275                 280                 285

Pro Lys Ser Lys Glu Glu Asp Lys His Leu Lys Phe Arg Ile Ser His
    290                 295                 300

Glu Leu Asp Ser Ala Ser Ser Glu Val Asn
305                 310
```

<210> SEQ ID NO 3
<211> LENGTH: 1343
<212> TYPE: DNA
<213> ORGANISM: Homo sapiens

```
<400> SEQUENCE: 3
gaccagactc gtctcaggcc agttgcagcc ttctcagcca acgccgacc aaggaaaact      60
cactaccatg agaattgcag tgatttgctt ttgcctccta ggcatcacct gtgccatacc    120
agttaaacag gctgattctg aagttctga ggaaaagcag aatgctgtgt cctctgaaga    180
aaccaatgac tttaaacaag agacccttcc aagtaagtcc aacgaaagcc atgaccacat    240
ggatgatatg gatgatgaag atgatgatga ccatgtggac agccaggact ccattgactc    300
gaacgactct gatgatgtag atgacactga tgattctcac cagtctgatg agtctcacca    360
ttctgatgaa tctgatgaac tggtcactga ttttcccacg gacctgccag caaccgaagt    420
tttcactcca gttgtcccca cagtagacac atatgatggc cgaggtgata gtgtggttta    480
tggactgagg tcaaaatcta agaagtttcg cagacctgac atccagtacc ctgatgctac    540
agacgaggac atcacctcac acatggaaag cgaggagttg aatggtgcat acaaggccat    600
ccccgttgcc caggacctga acgcgccttc tgattgggac agccgtggga aggacagtta    660
tgaaacgagt cagctggatg accagagtgc tgaaacccac agccacaagc agtccagatt    720
atataagcgg aaagccaatg atgagagcaa tgagcattcc gatgtgattg atagtcagga    780
actttccaaa gtcagccgtg aattccacag ccatgaattt cacagccatg aagatatgct    840
ggttgtagac cccaaaagta aggaagaaga taaacacctg aaatttcgta tttctcatga    900
attagatagt gcatcttctg aggtcaatta aaaggagaaa aaatacaatt ctcactttg     960
catttagtca aagaaaaaa tgctttatag caaaatgaaa gagaacatga aatgcttctt    1020
tctcagttta ttggttgaat gtgtatctat ttgagtctgg aaataactaa tgtgtttgat   1080
aattagttta gtttgtggct tcatggaaac tccctgtaaa ctaaaagctt cagggttatg   1140
tctatgttca ttctatagaa gaaatgcaaa ctatcactgt attttaatat ttgttattct   1200
ctcatgaata gaaattttatg tagaagcaaa caaaatactt ttacccactt aaaaagagaa   1260
tataacattt tatgtcacta taatcttttg ttttttaagt tagtgtatat tttgttgtga   1320
ttatctttt gtggtgtgaa taa                                            1343

<210> SEQ ID NO 4
<211> LENGTH: 44
<212> TYPE: PRT
<213> ORGANISM: Homo sapiens

<400> SEQUENCE: 4

Leu Arg Ser Lys Ser Lys Lys Phe Arg Arg Pro Asp Ile Gln Tyr Pro
1               5                   10                  15
Asp Ala Thr Asp Glu His Ile Thr Ser His Met Glu Ser Glu Glu Leu
            20                  25                  30
Asn Gly Ala Tyr Lys Ala Ile Pro Val Ala Gln Asp
        35                  40

<210> SEQ ID NO 5
<211> LENGTH: 10
<212> TYPE: PRT
<213> ORGANISM: Homo sapiens

<400> SEQUENCE: 5

Pro Asp Ile Gln Tyr Pro Asp Ala Thr Asp
1               5                   10

<210> SEQ ID NO 6
```

```
<211> LENGTH: 10
<212> TYPE: PRT
<213> ORGANISM: Homo sapiens

<400> SEQUENCE: 6

His Met Glu Ser Glu Glu Leu Asn Gly Ala
1               5                   10

<210> SEQ ID NO 7
<211> LENGTH: 10
<212> TYPE: PRT
<213> ORGANISM: Homo sapiens

<400> SEQUENCE: 7

Glu Leu Asn Gly Ala Tyr Lys Ala Ile Pro
1               5                   10

<210> SEQ ID NO 8
<211> LENGTH: 15
<212> TYPE: PRT
<213> ORGANISM: Homo sapiens

<400> SEQUENCE: 8

His Met Glu Ser Glu Glu Leu Asn Gly Ala Tyr Lys Ala Ile Pro
1               5                   10                  15

<210> SEQ ID NO 9
<211> LENGTH: 287
<212> TYPE: PRT
<213> ORGANISM: Homo sapiens

<400> SEQUENCE: 9

Met Arg Ile Ala Val Ile Cys Phe Cys Leu Leu Gly Ile Thr Cys Ala
1               5                   10                  15

Ile Pro Val Lys Gln Ala Asp Ser Gly Ser Ser Glu Glu Lys Gln Asn
                20                  25                  30

Ala Val Ser Ser Glu Glu Thr Asn Asp Phe Lys Gln Glu Thr Leu Pro
            35                  40                  45

Ser Lys Ser Asn Glu Ser His Asp His Met Asp Asp Met Asp Asp Glu
        50                  55                  60

Asp Asp Asp Asp His Val Asp Ser Gln Asp Ser Ile Asp Ser Asn Asp
65                  70                  75                  80

Ser Asp Asp Val Asp Asp Thr Asp Asp Ser His Gln Ser Asp Glu Ser
                85                  90                  95

His His Ser Asp Glu Ser Asp Glu Leu Val Thr Asp Phe Pro Thr Asp
            100                 105                 110

Leu Pro Ala Thr Glu Val Phe Thr Pro Val Val Pro Thr Val Asp Thr
            115                 120                 125

Tyr Asp Gly Arg Gly Asp Ser Val Val Tyr Gly Leu Arg Ser Lys Ser
        130                 135                 140

Lys Lys Phe Arg Arg Pro Asp Ile Gln Tyr Pro Asp Ala Thr Asp Glu
145                 150                 155                 160

Asp Ile Thr Ser His Met Glu Ser Glu Glu Leu Asn Gly Ala Tyr Lys
                165                 170                 175

Ala Ile Pro Val Ala Gln Asp Leu Asn Ala Pro Ser Asp Trp Asp Ser
            180                 185                 190

Arg Gly Lys Asp Ser Tyr Glu Thr Ser Gln Leu Asp Asp Gln Ser Ala
        195                 200                 205

Glu Thr His Ser His Lys Gln Ser Arg Leu Tyr Lys Arg Lys Ala Asn
```

-continued

```
                    210                 215                 220
Asp Glu Ser Asn Glu His Ser Asp Val Ile Asp Ser Gln Glu Leu Ser
225                 230                 235                 240

Lys Val Ser Arg Glu Phe His Ser His Glu Phe His Ser His Glu Asp
                245                 250                 255

Met Leu Val Val Asp Pro Lys Ser Lys Glu Glu Asp Lys His Leu Lys
            260                 265                 270

Phe Arg Ile Ser His Glu Leu Asp Ser Ala Ser Ser Glu Val Asn
        275                 280                 285

<210> SEQ ID NO 10
<211> LENGTH: 25
<212> TYPE: DNA
<213> ORGANISM: Artificial Sequence
<220> FEATURE:
<223> OTHER INFORMATION: Synthetic oligonucleotide primer.

<400> SEQUENCE: 10
tctcctagcc ccacagaatg ctgtg                                           25

<210> SEQ ID NO 11
<211> LENGTH: 25
<212> TYPE: DNA
<213> ORGANISM: Artificial Sequence
<220> FEATURE:
<223> OTHER INFORMATION: Synthetic oligonucleotide primer.

<400> SEQUENCE: 11
aggaaaagca gaatgctgtg tcctc                                           25

<210> SEQ ID NO 12
<211> LENGTH: 23
<212> TYPE: PRT
<213> ORGANISM: Homo sapiens

<400> SEQUENCE: 12

Asp Ile Val Met Thr Gln Ser Pro Asp Ser Leu Ala Val Ser Leu Gly
1               5                   10                  15

Glu Arg Ala Thr Ile Asn Cys
            20

<210> SEQ ID NO 13
<211> LENGTH: 14
<212> TYPE: PRT
<213> ORGANISM: Homo sapiens

<400> SEQUENCE: 13

Trp Tyr Gln Gln Lys Pro Gly Gln Pro Pro Leu Leu Ile Tyr
1               5                   10

<210> SEQ ID NO 14
<211> LENGTH: 32
<212> TYPE: PRT
<213> ORGANISM: Homo sapiens

<400> SEQUENCE: 14

Gly Val Pro Asp Arg Phe Gly Ser Gly Ser Gly Thr Asp Phe Thr
1               5                   10                  15

Leu Thr Ile Ser Ser Leu Gln Ala Glu Asp Val Ala Val Tyr Tyr Cys
            20                  25                  30

<210> SEQ ID NO 15
```

```
<211> LENGTH: 11
<212> TYPE: PRT
<213> ORGANISM: Homo sapiens

<400> SEQUENCE: 15

Phe Gly Gln Gly Gln Thr Lys Leu Glu Ile Lys
1               5                   10

<210> SEQ ID NO 16
<211> LENGTH: 30
<212> TYPE: PRT
<213> ORGANISM: Homo sapiens

<400> SEQUENCE: 16

Gln Val Gln Leu Val Gln Ser Gly Ala Glu Val Lys Lys Pro Gln Ala
1               5                   10                  15

Ser Val Lys Val Ser Cys Lys Ala Ser Gln Tyr Thr Phe Thr
            20                  25                  30

<210> SEQ ID NO 17
<211> LENGTH: 14
<212> TYPE: PRT
<213> ORGANISM: Homo sapiens

<400> SEQUENCE: 17

Trp Val Arg Gln Ala Pro Gly Gln Arg Leu Glu Trp Met Gly
1               5                   10

<210> SEQ ID NO 18
<211> LENGTH: 32
<212> TYPE: PRT
<213> ORGANISM: Homo sapiens

<400> SEQUENCE: 18

Arg Val Thr Ile Thr Arg Asp Thr Ser Ala Ser Thr Ala Tyr Met Glu
1               5                   10                  15

Leu Ser Ser Leu Arg Ser Glu Asp Thr Ala Val Tyr Tyr Cys Ala Arg
            20                  25                  30

<210> SEQ ID NO 19
<211> LENGTH: 11
<212> TYPE: PRT
<213> ORGANISM: Homo sapiens

<400> SEQUENCE: 19

Trp Gly Gln Gly Thr Leu Val Thr Val Ser Ser
1               5                   10
```

COMPOSITIONS AND METHODS FOR DIAGNOSIS AND TREATMENT OF TUMORS

CROSS REFERENCE TO RELATED APPLICATIONS

This is a continuation-in-part of International Patent Application No. PCT/US2007/071712 filed on Jun. 20, 2007, which claims priority from U.S. Provisional Application No. 60/805,298 filed Jun. 20, 2006, which is herein incorporated by reference.

FIELD

This application relates to methods of diagnosing and treating a tumor that has increased expression of osteopontin (OPN), such as metastatic hepatocellular carcinoma (HCC), as well as compositions and kits that can be used for such methods. Also provided are antibodies that specifically bind to a fragment of OPN (OPN-5kD) generated by metalloproteinase-9 (MMP-9) cleavage.

BACKGROUND

Elucidating the molecular events that promote tumor cell invasion continues to be a challenge for the treatment and prevention of hepatocellular carcinoma (HCC). HCC is a highly aggressive carcinoma of the liver which has been reported to occur world-wide in increasing numbers. Intrahepatic metastatic recurrences via the portal vein are the main cause of death in HCC patients who have undergone partial hepatectomy or liver transplantation (Korn, *World J. Gastroenterol.*, 7:777-8, 2001). Identifying the main 'players' and how they contribute to the tumor cell metastatic cascade, for example at the early stages of cellular invasion, can present opportunities for lessening the severity of HCC through new therapeutic interventions.

Osteopontin (OPN, SPP1) is a secreted multi-functional glycoprotein expressed at high levels in tumors and the surrounding stroma of numerous cancers, including those of the liver, and is alternatively spliced into at least 3 isoforms (OPN-a, OPN-b, OPN-c) (Butler, *Ann. N.Y. Acad. Sci.*, 760: 6-11, 1995; Coppola et al., *Clin. Cancer Res.*, 10: 184-90, 2004). Increased serum and plasma OPN levels (~4-10 fold) are associated with advanced stage lung, hepatic, breast, colon, and prostate carcinomas (Oates et al., *Invasion Metastasis*, 17:1-15, 1997; Fedarko et al., *Clin. Cancer Res.*, 7:4060-6, 2001; Singhal et al., *Clin. Cancer Res.*, 3:605-11, 1997.). OPN expression can predict high grade, late stage and early recurrence HCC (Pan et al., *Cancer*, 98:119-27, 2003) and is highly correlated with tumor recurrence and decreased patient survival following orthotopic liver transplantation (Wang, *Hepatology*, 42(4), Suppl. 1:391 A, 2005). Prominent OPN levels have been detected in metastatic HCC tumor cells at the leading edge of pseudopodia and filopodia (Suzuki et al., *J. Bone Miner. Res.*, 17:1486-97, 2002) and in macrophages at the tumor-stroma interface (Senger et al., *Ann. N. Y. Acad. Sci.*, 760: 83-100, 1995). A correlation between OPN mRNA expression and primary HCC tumor metastasis has been shown (Ye et al., *Nat. Med.*, 9: 416-423, 2003). Cytoplasmic OPN was detected in vascularized regions of primary HCC tumors but not in normal liver. In addition, a neutralizing antibody to OPN decreased pulmonary secondary lesions in nude mice and inhibited tumor cell invasion.

Local and extra-hepatic HCC tumor cell invasion is associated with extensive matrix remodeling, angiogenesis, and hepatocyte injury (McKenna et al., *Am. J. Surg.*, 183: 588-94, 2002). The members of the zinc-dependent endopeptidase family of matrix metalloproteinases (MMPs) catabolize extracellular matrix components (Theret et al., *Hepatology*, 34:82-88, 2001; Liaw and Crawford, *Braz. J. Med. Biol. Res.*, 32:805-812, 1999). Each MMP contains a catalytic and pro-peptide regulatory domain and a variable number of carboxy-terminal hemopoexin-like structural domains and are broadly divided into subclasses based on substrate activity. The two gelatinases (MMP-2 and MMP-9) play roles in tumor invasion and angiogenesis and participate in cancer progression in several neoplasias (Turpeenniemi-Hujanen, *Biochimie*, 87:287-97, 2005; Hanemaaijer et al., *Int. J. Cancer*, 86:204-7, 2000; Scorilas et al., *Br. J. Cancer*, 84:1488-96, 2001). Active MMP-9 enzymatically cleaves proteins of the basement membrane (such as collagens type IV, V, VII, X, and XIV) and can be detected at the invasive front of HCC (Kaneyoshi et al., *Clin. Cancer Res.*, 7:4027-32, 2001). A substantial increase in MMP-9 mRNA levels in HCC primary metastatic tumors has been observed (Ye et al., *Nat. Med.* 9:416-23, 2003), which is consistent with indications of HCC tumor malignancy and MMP-9 abundance (Ashida et al., *Am. J. Pathol.*, 149:1803-11, 1996; Wei et al., *Hunan. Yi. Ke. Da. Xue. Xue. Bao.*, 28:212-6, 2003).

Stromelysin-1 (MMP-3) and matrilysin (MMP-7) are reported to cleave OPN at residues 166 and 210 (Agnihotri et al., *J. Biol. Chem.*, 276:28261-7, 2001). MMP-3/-7 digested OPN fragments increase AsPC-1 and HeLa tumor cell adhesion via cell surface integrin receptors and MMP-3 cleaved OPN can increase mouse peritoneal macrophage cell migration. The thrombin coagulation factor also cleaves OPN at residue 168, resulting in two fragments of similar molecular weight (~28-30 kD) can be detected in the serum and plasma of patients with cancer (Senger et al., Cancer Res., 48:5770-4, 1988). Thrombin-cleaved OPN can mediate increased tumor and macrophage cell adhesion and migration via exposure of the amino-terminal reactive RGD sequence and binding to cell surface integrins, namely the vitronectin receptor αVβ3, although interactions with αVβ1, αVβ5, α4β1, and α9β1 have been described (Sodek et al., *Crit. Rev. Oral Biol. Med.*, 11:279-303, 2000; Wai and Kuo, *J. Surg. Res.*, 121:228-41, 2004; Weber, *Biochim. Biophys. Acta*, 1552:61-85, 2001). Conversely, the COOH-terminal thrombin-cleaved fragment has been proposed to induce macrophage migration primarily through CD44 receptors (Weber et al., *J. Leukoc. Biol.*, 72:752-61, 2002).

SUMMARY

Methods of treating a tumor that overexpresses osteopontin (OPN), such as a tumor that overexpresses OPN (for example OPN-c) and MMP-9, as well as diagnosing and prognosing such tumors, are provided. Examples of such tumors include but are not limited to cancers of the liver, breast, colon, and prostate. The disclosed treatment, diagnostic, and prognostic methods can be used in combination or individually.

The inventors have determined that MMP-9 mediates OPN proteolytic cleavage into several fragments including OPN-5kD (such as SEQ ID NO: 4), which is a ligand for CD44 receptor. The interaction of OPN-5kD and the CD44 receptor increases HCC tumor cell invasion. The inventors have identified several fragments of OPN-5kD that significantly reduce HCC tumor cell invasion, which may be achieved by disrupting the interaction between OPN-5kD and CD44 receptor. Based on this observation, new methods of treating such tumors are disclosed, for example by using short invasive-blocking peptides targeted to the effects of OPN-5kD. The inventors have also identified monoclonal antibodies that bind to OPN-5kD which can be used to significantly reduce HCC tumor cell invasion by disrupting the interaction between OPN-5kD and the CD44 receptor. Therefore, new methods of treating such tumors are disclosed, for example by administering therapeutically effective amounts of one or more peptides or antibodies that reduce or inhibit the effects of OPN-5kD.

Methods of treating a tumor in a subject are provided, such as a tumor that overexpresses OPN, MMP-9, or both. A particular example of such a tumor is HCC. In one example, the method includes administering to the subject a therapeutically effective amount of an agent that decreases cellular invasion of a tumor cell effected by the interaction of OPN-5kD and the CD44 receptor, such as a peptide fragment of OPN-5kD, or an antibody that binds to OPN-5kD, thereby treating the tumor. A particular example of OPN-5kD sequence is provided in SEQ ID NO: 4. However, one skilled in the art will appreciate that variants of this sequence (such as polymorphisms) can retain OPN-5kD activity (such as the ability to bind to CD44 receptor with high affinity). For example, a variant OPN-5kD sequence may include at least one amino acid deletion, substitution, addition, or combinations thereof, such as 1-5 conservative amino acid substitutions, while retaining the ability to stimulate cellular invasion upon interaction with the CD44 receptor.

Exemplary therapeutic peptides can include at least one peptide sequence, or a plurality of peptide sequences, wherein each peptide fragment of OPN-5kD includes at least 5 contiguous amino acids of OPN-5kD and in some examples is no more than 50 amino acids. For example, the peptide can be a composition that includes one or more peptides consisting of the amino acid sequence shown in SEQ ID NO: 5, 6, 7, or 8. Exemplary therapeutic antibodies can include a single monoclonal antibody or an equivalent specific binding agent the binds to one epitope (e.g., amino acids 30-36 of SEQ ID NO: 4) or multiple antibodies that bind to more than one epitope in OPN-5kD. If desired, therapeutically effective amounts of one or more additional therapeutic agents, such as an anti-neoplastic chemotherapeutic agent, can be administered to the subject. In particular examples, treatment includes reducing cellular invasion by a tumor, such as reducing or preventing metastasis of a tumor. In some examples, treating the tumor prolongs survival time of the subject (for example by at least 2 months, at least 6 months, or even at least 12 months).

Also provided by the present disclosure are therapeutic compositions that can be used to treat a tumor, such as a tumor that overexpresses OPN (such as overexpresses OPN and MMP-9), for example HCC. Such compositions can be used in the therapeutic methods provided herein. In one example, the composition includes one or more peptide fragments of OPN-5kD. In a specific example, the composition includes one or more peptides consisting of the amino acid sequence of SEQ ID NO: 5, 6, 7, or 8. In another example the therapeutic compositions include antibodies that specifically bind to OPN-5kD. The disclosed compositions can include one or more pharmaceutically acceptable carriers, as well as additional therapeutic agents (such as other anti-neoplastic agents). Such therapeutic compositions can also be part of a kit, such as a kit that includes one more other anti-neoplastic agents (such as IL-2, IL-12, GM-CSF, a chemotherapeutic agent, or combinations thereof).

Methods of diagnosing and prognosing a tumor (such as a tumor that overexpresses OPN, MMP-9, or both) are provided. In some examples, such methods are performed prior to the treatment methods described herein. However, such methods can also be used independently of the disclosed treatment methods. In particular examples, the method includes determining if the OPN-5kD fragment is present in the subject, for example by detecting OPN-5kD in the subject's serum. For example, a sample from the subject that includes peptides (such as serum) is contacted with an agent that specifically binds to OPN-5kD (such as an antibody that specifically binds to an epitope of OPN-5kD), then it is determined whether the agent specifically bound to proteins in the sample. If specific binding of the agent to OPN-5kD in the sample is detected, this indicates that the subject has a tumor (such as HCC), has a poor prognosis (for example because this indicates that the tumor has metastasized), or both. Such a method provides a non-invasive means for diagnosis and prognosis of a tumor, such as metastatic HCC. In another example, the method includes contacting a sample from the subject that includes nucleic acid molecules (such as a tumor sample) with an agent that permits detection of OPN-c nucleic acid molecules (such as cDNA or mRNA), then determining a relative amount of OPN-c nucleic acid molecules in the sample. For example, if increased OPN-c mRNA expression is detected in non-cancerous tissue adjacent to the tumor or in the tumor itself (or both), this indicates that the subject's tumor has increased metastatic potential. Similar methods can be used to measure OPN-c protein expression, as an alternative to OPN-c nucleic acid molecule expression.

Also provided are antibodies that specifically bind OPN-5kD, such as an antibody that binds to an epitope sequence within SEQ ID NO: 4, or a fragment thereof such as any of SEQ ID NOS: 5-8. A specific epitope is amino acids 30-36 of SEQ ID NO: 4. Such antibodies are useful for detection and treatment of tumors and can be part of a kit. Diagnostic kits can include other agents to permit detection of the antibody, such as a labeled secondary antibody. A specific example of such antibodies is the OPN-5kD monoclonal antibody 5kd106-13D. Thus, the 5kd106-13 D antibody, chimeric form or humanized form thereof or functional fragment thereof can be used to detect OPN-5kD and OPN-expressing tumors, as well as treat such tumors. Chimeric forms of 5kd106-13D, humanized forms of 5kd106-13D, and functional fragments of 5kd106-13D, are also disclosed. The 5kd106-13D antibody, chimeric form, humanized form or functional fragment of these antibodies can be conjugated to an effector molecule, such as a detectable marker, a therapeutic agent, or a toxin. Kits that contain the monoclonal antibody 5kd106-13D, a chimeric form, or a humanized form thereof or functional fragments thereof are also disclosed. Nucleic acid molecules encoding the monoclonal antibody 5kd106-13D, a chimeric form or humanized form thereof or functional fragments thereof are also disclosed. A hybridoma that produces 5kd106-13D is also provided.

The foregoing and other objects and features of the disclosure will become more apparent from the following detailed description, which proceeds with reference to the accompanying figures.

BRIEF DESCRIPTION OF THE DRAWINGS

FIGS. 7A and B are bar graphs showing that some 10-mer peptides can inhibit OPN-5kD induced HCC cellular invasion. Data were normalized to uncoated membrane chamber values and adjusted by media control values (=1). (A) Un-paired student's t-tests were used to compare mean and standard deviation values of OPN-5kD peptide versus each of the 10-mer peptides ($\alpha=0.05$). (B) Significance of the small peptide inhibition of the OPN-5kD peptide increased cellular invasion was tested using un-paired student's t-tests ($\alpha=0.05$). * denotes significance (A) $p<0.037$ and (B) $p<0.002$.

SEQUENCE LISTING

Figure 1A:
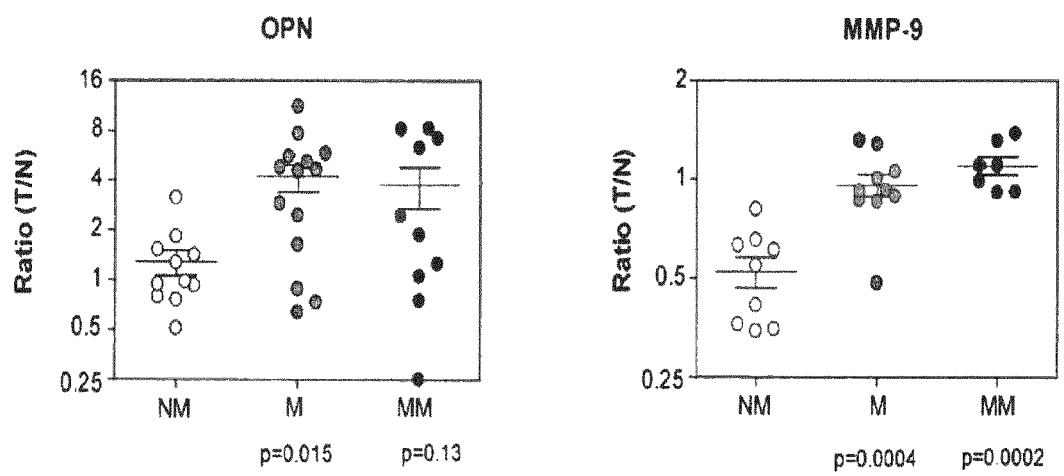
FIG. 1A are two plots showing that mRNA expression of OPN (left) and MMP-9 (right) correlate with HCC tumor metastasis. NM=non-metastatic (n=11), M=metastatic (n=14), MM=metastatic intra-hepatic lesion (n=10). All data were normalized to mRNA levels detected in the normal tissue immediately adjacent to the tumor samples (T/N). Statistical analysis was performed using Mann Whitney non-parametric t-tests ($\alpha=0.05$).

The nucleic and amino acid sequences listed in the accompanying sequence listing are shown using standard letter abbreviations for nucleotide bases, and one letter code for amino acids. Only one strand of each nucleic acid sequence is shown, but the complementary strand is understood as included by any reference to the displayed strand.

SEQ ID NO: 1 is a cDNA sequence for a human osteopontin-a.
SEQ ID NO: 2 is the protein encoded by SEQ ID NO: 1.
SEQ ID NO: 3 is a cDNA sequence for a human osteopontin-c.
SEQ ID NO: 4 is an amino acid sequence of OPN-5kD.
SEQ ID NO: 5 is the p3 fragment of OPN-5kD.
SEQ ID NO: 6 is the p6 fragment of OPN-5kD.
SEQ ID NO: 7 is the p7 fragment of OPN-5kD.
SEQ ID NO: 8 is a fragment of OPN-5kD.
SEQ ID NO: 9 is the protein encoded by SEQ ID NO: 3.
SEQ ID NO: 10 is a unique reporter sequence for OPN-a.
SEQ ID NO: 11 is a unique reporter sequence for OPN-c.
SEQ ID NOS: 12-15 show exemplary light chain frameworks of human MAb LEN.
SEQ ID NOS: 16-19 show exemplary heavy chain frameworks of human MAb 21/28 CL.

DETAILED DESCRIPTION OF SEVERAL EMBODIMENTS

Abbreviations and Terms

The following explanations of terms and methods are provided to better describe the present disclosure and to guide those of ordinary skill in the art in the practice of the present disclosure. The singular forms "a," "an," and "the" refer to one or more than one, unless the context clearly dictates otherwise. For example, the term "comprising a peptide" includes single or plural peptides and is considered equivalent to the phrase "comprising at least one peptide." The term "or" refers to a single element of stated alternative elements or a combination of two or more elements, unless the context clearly indicates otherwise. As used herein, "comprises" means "includes." Thus, "comprising A or B," means "including A, B, or A and B," without excluding additional elements. All Genbank Accession numbers are incorporated by reference (the sequence available on Dec. 15, 2008).

Unless explained otherwise, all technical and scientific terms used herein have the same meaning as commonly understood to one of ordinary skill in the art to which this disclosure belongs.

HCC: hepatocellular carcinoma
IL-2: interleukin-2
MMP-9: matrix metalloproteinase-9
OPN: osteopontin Administration: To provide or give a subject an agent, such as a composition that includes a peptide fragment of OPN-5kD, such as one or more of SEQ ID NOS: 5-8, or OPN-5kD specific antibodies, by any effective route. Exemplary routes of administration include, but are not limited to, oral, injection (such as subcutaneous, intramuscular, intradermal, intraperitoneal, and intravenous), sublingual, rectal, transdermal (e.g., topical), intranasal, vaginal and inhalation routes.

Antibody: A polypeptide ligand comprising at least a light chain or heavy chain immunoglobulin variable region which specifically recognizes and binds an epitope of an antigen. For example, OPN-5kD specific antibodies include those that specifically bind to the OPN-5kD fragment antigen or an epitope thereof (e.g., EELNGAY, amino acids 30 to 36 of SEQ ID NO: 4). Antibodies are composed of a heavy and a light chain, each of which has a variable region, termed the variable heavy ($V_H$) region and the variable light ($V_L$) region. Together, the $V_H$ region and the $V_L$ region are responsible for binding the antigen recognized by the antibody. Includes polyclonal antibodies, monoclonal antibodies, and fragments thereof.

This includes intact immunoglobulins and the variants and portions of them well known in the art, such as Fab' fragments, F(ab)'$_2$ fragments, single chain Fv proteins ("scFv"), and disulfide stabilized Fv proteins ("dsFv"). A scFv protein is a fusion protein in which a light chain variable region of an immunoglobulin and a heavy chain variable region of an immunoglobulin are bound by a linker, while in dsFvs, the chains have been mutated to introduce a disulfide bond to stabilize the association of the chains. The term also includes genetically engineered forms such as chimeric antibodies (for example, humanized murine antibodies), heteroconjugate antibodies (such as, bispecific antibodies). See also, *Pierce Catalog and Handbook*, 1994-1995 (Pierce Chemical Co., Rockford, Ill.); Kuby, J., *Immunology*, 3$^{rd}$ Ed., W.H. Freeman & Co., New York, 1997.

Typically, a naturally occurring immunoglobulin has heavy (H) chains and light (L) chains interconnected by disulfide bonds. There are two types of light chain, lambda (λ) and kappa (k). There are five main heavy chain classes (or isotypes) which determine the functional activity of an antibody molecule: IgM, IgD, IgG, IgA and IgE.

Each heavy and light chain contains a constant region and a variable region, (the regions are also known as "domains"). In combination, the heavy and the light chain variable regions specifically bind the antigen. Light and heavy chain variable regions contain a "framework" region interrupted by three hypervariable regions, also called "complementarity-determining regions" or "CDRs". The extent of the framework region and CDRs have been defined (see, Kabat et al., *Sequences of Proteins of Immunological Interest*, U.S. Department of Health and Human Services, 1991, which is hereby incorporated by reference). The Kabat database is now maintained online. The sequences of the framework regions of different light or heavy chains are relatively conserved within a species. The framework region of an antibody, that is the combined framework regions of the constituent light and heavy chains, serves to position and align the CDRs in three-dimensional space.

The CDRs are primarily responsible for binding to an epitope of an antigen. The CDRs of each chain are typically referred to as CDR1, CDR2, and CDR3, numbered sequentially starting from the N-terminus, and are also typically identified by the chain in which the particular CDR is located. Thus, a $V_H$ CDR3 is located in the variable domain of the heavy chain of the antibody in which it is found, whereas a $V_L$ CDR1 is the CDR1 from the variable domain of the light chain of the antibody in which it is found. An antibody that binds an antigen of interest has a specific $V_H$ region and the $V_L$ region sequence, and thus specific CDR sequences. Antibodies with different specificities (due to different combining sites for different antigens) have different CDRs. Although it is the CDRs that vary from antibody to antibody, only a limited number of amino acid positions within the CDRs are directly involved in antigen binding. These positions within the CDRs are called specificity determining residues (SDRs).

References to "$V_H$" or "VH" refer to the variable region of an immunoglobulin heavy chain, including that of an Fv, scFv, dsFv or Fab. References to "$V_L$" or "VL" refer to the variable region of an immunoglobulin light chain, including that of an Fv, scFv, dsFv or Fab.

A "monoclonal antibody" is an antibody produced by a single clone of B-lymphocytes or by a cell into which the light and heavy chain genes of a single antibody have been transfected, or a progeny thereof. Monoclonal antibodies are produced by methods known to those of skill in the art, for instance by making hybrid antibody-forming cells from a fusion of myeloma cells with immune spleen cells. Monoclonal antibodies include humanized monoclonal antibodies. In some example a monoclonal antibody is the monoclonal antibody 5kd106-13D, which is specific for the epitope EELNGAY (amino acids 30 to 36 of SEQ ID NO: 4).

A "chimeric antibody" has framework residues from one species, such as human, and CDRs or SDRs (which generally confer antigen binding) from another species, such as a murine antibody that specifically binds an epitope of the OPN-5kD fragment. Most typically, chimeric antibodies include human and murine antibody domains, generally human constant regions and murine variable regions, murine CDRs and/or murine SDRs. In some examples a chimeric antibody includes the SDRs or CDRs from the monoclonal antibody 5kd106-13D. In one example, a chimeric antibody is a hybrid protein composed of the variable or antigen-binding domain from a mouse antibody and the constant or effector domain from a human antibody (such as an antibody that recognizes an epitope of OPN-5kD), although other mammalian species can be used, or the variable region can be produced by molecular techniques. Methods of making chimeric antibodies are well known in the art, for example, see U.S. Pat. No. 5,807,715.

A "humanized antibody" is an immunoglobulin including a human framework region and one or more CDRs from a non-human or SDRs (for example a mouse, rat, or synthetic) immunoglobulin. The non-human immunoglobulin providing the CDRs is termed a "donor," and the human immunoglobulin providing the framework is termed an "acceptor." An exemplary donor is CDRs from monoclonal antibody 5kd106-13D. In one embodiment, all the CDRs are from the donor immunoglobulin in a humanized immunoglobulin. Constant regions need not be present, but if they are, they are substantially identical to human immunoglobulin constant regions, such as at least about 85-90%, such as about 95% or more identical. Hence, all parts of a humanized immunoglobulin, except possibly the CDRs, are substantially identical to corresponding parts of natural human immunoglobulin sequences. The acceptor framework of a humanized immunoglobulin or antibody can have a limited number of substitutions by amino acids taken from the donor framework. Humanized or other monoclonal antibodies can have additional amino acid substitutions which have substantially no effect on antigen binding or other immunoglobulin functions. Exemplary conservative substitutions are described above (see also U.S. Pat. No. 5,585,089). Humanized immunoglobulins can be constructed by means of genetic engineering, for example, see U.S. Pat. Nos. 5,225,539 and 5,585,089.

Binding affinity: Affinity of an antibody for an antigen, such as the affinity of an antibody (e.g., monoclonal antibody 5kd106-13D) for an OPN-5kD peptide fragment or epitope thereof. In one example, affinity is calculated by a modification of the Scatchard method described by Frankel et al., *Mol. Immunol.*, 16:101-106, 1979. In another example, binding affinity is measured by an antigen/antibody dissociation rate. In yet another example, a high binding affinity is measured by a competition radioimmunoassay. In several examples, a high binding affinity is at least about $1 \times 10^{-8}$ M. In other example, a high binding affinity is at least about $1.5 \times 10^{-8}$, at least about $2.0 \times 10^{-8}$, at least about $2.5 \times 10^{-8}$, at least about $3.0 \times 10^{-8}$, at least about $3.5 \times 10^{-8}$, at least about $4.0 \times 10^{-8}$, at least about $4.5 \times 10^{-8}$, or at least about $5.0 \times 10^{-8}$ M.

In a particular example, a functional variant of an OPN-5kD peptide retains a similar binding affinity for an antibody than the binding affinity of the native OPN-5kD peptide (such as SEQ ID NO: 4) for the same antibody.

Cancer: Malignant neoplasm that has undergone characteristic anaplasia with loss of differentiation, increased rate of growth, invasion of surrounding tissue, and is capable of metastasis.

CD44 receptors: A family of cell-surface adhesion molecules found on both normal and malignant cell types that can mediate cell-matrix and cell-cell interactions. CD44 receptors have been associated with increased inflammation and metastasis. Based on the results shown herein, it is proposed that OPN-5kD is a ligand for CD44 receptors, and this interaction enhances cellular invasion, for example of HCC cells.

Chemotherapeutic agent: In cancer treatment, refers to the administration of one or a combination of compounds to kill or slow the reproduction of rapidly multiplying cells. Chemotherapeutic agents include anti-neoplastics known by those skilled in the art, including, but not limited to: 5-fluorouracil (5-FU), azathioprine, cyclophosphamide, antimetabolites (such as Fludarabine), antineoplastics (such as Etoposide, Doxorubicin, methotrexate, and Vincristine), carboplatin, cis-platinum and the taxanes, such as taxol, monoclonal antibodies such as Avastin or Herceptin, and growth pathway inhibitors such as Gleevac. In particular examples, such chemotherapeutic agents are administered in combination with a therapy that reduces cellular invasion (for example before, during or after administration of a therapeutic amount of one or more fragments of OPN-5kD that include at least 5 contiguous amino acids of SEQ ID NO: 4, such as SEQ ID NOS: 5-8, or OPN-5kD specific antibodies).

Complementarity Determining Region (CDR): Amino acid sequences which together define the binding affinity and specificity of the natural Fv region of a native Ig binding site. The light and heavy chains of an immunoglobulin each have three CDRs, designated L-CDR1, L-CDR2, L-CDR3 and H-CDR1, H-CDR2, H-CDR3, respectively. By definition, the CDRs of the light chain are bounded by the residues at positions 24 and 34 (L-CDR1), 50 and 56 (L-CDR2), 89 and 97 (L-CDR3); the CDRs of the heavy chain are bounded by the residues at positions 31 and 35b (H-CDR1), 50 and 65 (H-CDR2), 95 and 102 (H-CDR3), using the numbering convention delineated by Kabat et al., ([99]) *Sequences of Proteins of Immunological Interest*, 5th Edition, U.S. Department of Health and Human Services, Public Health Service, National Institutes of Health, Bethesda, Md. (NIH Publication No. 91-3242). CDRs contain the specificity determining regions (SDRs) of the antibody. In some examples a CDR is a CDR from the monoclonal antibody 5kd106-13D.

Conservative substitution: One or more amino acid substitutions for amino acid residues having similar biochemical properties. Typically, conservative substitutions have little to no impact on the activity of a resulting polypeptide. For example, a conservative substitution in an OPN-5kD fragment (such as one or more conservative substitutions in any of SEQ ID NOS: 5-8) ideally does not substantially affect the ability of the peptide to reduce invasion of an HCC cell. Methods that can be used to determine the amount of invasion are disclosed herein (for example, see Examples 4-8). In another particular example, a conservative substitution in OPN-5kD (such as SEQ ID NO: 4) ideally does not significantly decrease the ability of OPN-5kD to specifically bind to CD44, and in some examples may not affect the ability of such an interaction to stimulate cellular invasion. The interaction between an OPN-5kD variant containing one or more conservative amino acid substitutions and CD44 can be measured using methods known in the art, such as incubating a labeled OPN-5kD antibody with CD44 receptor-expressing cells in the presence of OPN-5kD, wherein the presence of detectable label indicates the presence of bound OPN-5kD to the cells.

For example, an alanine scan can be used to identify which amino acid residues in SEQ ID NOS: 4-8 can tolerate an amino acid substitution. In one example, one or more conservative substitutions in SEQ ID NOS: 5-8 ideally do not decrease the observed reduction of invasion by more than 25%, for example not more than 20%, for example not more than 10%, when an alanine, or other conservative amino acid (such as those listed below), is substituted for one or more native amino acids. In one example, one or more conservative substitutions in SEQ ID NO: 4 ideally does not reduce the observed interaction of SEQ ID NO: 4 with CD44 receptor by more than 25%, for example not more than 20%, for example not more than 10%, when an alanine, or other conservative amino acid (such as those listed below), is substituted for one or more native amino acids.

In one example, one conservative substitution is included in the peptide, such as a single conservative amino acid substitution in any of SEQ ID NOS: 4-8. In another example, two conservative substitutions are included in the peptide (such as any of SEQ ID NOS: 4-8). In a further example, three conservative substitutions are included in the peptide (such as any of SEQ ID NOS: 4-8). A peptide can be produced to contain one or more conservative substitutions by manipulating the nucleotide sequence that encodes that polypeptide using, for example, standard procedures such as site-directed mutagenesis or PCR. Alternatively, a peptide can be produced to contain one or more conservative substitutions by using standard peptide synthesis methods.

Substitutional variants are those in which at least one residue in the amino acid sequence has been removed and a different residue inserted in its place. Examples of amino acids which may be substituted for an original amino acid in a protein and which are regarded as conservative substitutions include: Ser for Ala; Lys for Arg; Gln or His for Asn; Glu for Asp; Ser for Cys; Asn for Gln; Asp for Glu; Pro for Gly; Asn or Gln for His; Leu or Val for Ile; Ile or Val for Leu; Arg or Gln for Lys; Leu or Ile for Met; Met, Leu or Tyr for Phe; Thr for Ser; Ser for Thr; Tyr for Trp; Trp or Phe for Tyr; and Ile or Leu for Val.

Further information about conservative substitutions can be found in, among other locations in, Ben-Bassat et al., (*J. Bacteriol.* 169:751-7, 1987), O'Regan et al., (*Gene* 77:237-51, 1989), Sahin-Toth et al., (*Protein Sci.* 3:240-7, 1994), Hochuli et al., (*Bio/Technology* 6:1321-5, 1988) and in standard textbooks of genetics and molecular biology.

Decrease: To reduce the quality, amount, or strength of something.

In one example, a therapy decreases a tumor (such as the size or volume of a tumor, the number of tumors, the metastasis of a tumor, or combinations thereof), or one or more symptoms associated with a tumor, for example as compared to the response in the absence of the therapy. In a particular example, a therapy decreases the size or volume of a tumor, the number of tumors, the metastasis of a tumor, or combinations thereof, subsequent to the therapy, such as a decrease of at least 10%, at least 20%, at least 50%, or even at least 90%. Such decreases can be measured using the methods disclosed herein.

Deletion: The removal of a one or more nucleotides from a nucleic acid molecule or the removal of one or more amino acids from a protein, the regions on either side being joined together.

Effector molecule: The portion of a chimeric molecule, for example a chimeric molecule that includes an antibody (e.g., 5kd106-13D) or fragment thereof, that is intended to have a desired effect on a cell to which the chimeric molecule is targeted. Effector molecules are also known as an effector moieties (EM), therapeutic agents, or diagnostic agents, or similar terms.

Therapeutic agents include such compounds as nucleic acids, toxins, proteins, peptides, amino acids or derivatives, glycoproteins, radioisotopes, lipids, carbohydrates, or recombinant viruses. Nucleic acid therapeutic and diagnostic moieties include antisense nucleic acids, derivatized oligonucleotides for covalent cross-linking with single or duplex DNA, and triplex forming oligonucleotides. Alternatively, the molecule linked to a targeting moiety, such as an antibody, may be an encapsulation system, such as a liposome or micelle that contains a therapeutic composition such as a drug, a nucleic acid (such as an antisense nucleic acid), or another therapeutic moiety that can be shielded from direct exposure to the circulatory system. Means of preparing liposomes attached to antibodies are well known to those of skill in the art. See, for example, U.S. Pat. No. 4,957,735; and Connor et al., *Pharm. Ther.* 28:341-365, 1985. Diagnostic agents or moieties include radioisotopes and other detectable labels. Detectable labels useful for such purposes are also well known in the art, and include radioactive isotopes such as $^{32}P$, $^{125}I$, and $^{131}I$, fluorophores, chemiluminescent agents, magnetic resonance imaging agents and enzymes.

Epitope: An antigenic determinant. An epitope is the particular structure formed by chemical groups or peptide sequences in a molecule that is antigenic, meaning that elicits a specific immune response. An antibody specifically binds a particular antigenic epitope, for example on an OPN-5kD peptide fragment or portion thereof (e.g., EELNGAY, amino acids 30 to 36 of SEQ ID NO: 4). Epitopes can be formed both from contiguous amino acids or noncontiguous amino acids juxtaposed by tertiary folding of a protein. Epitopes formed from contiguous amino acids are typically retained on exposure to denaturing solvents whereas epitopes formed by tertiary folding are typically lost on treatment with denaturing solvents. An epitope typically includes at least 3, and more usually, at least 5, 6, 7, 8, 9 or 10 amino acids in a unique spatial conformation, such as this number of contiguous amino acids from OPN-5Kd (e.g., SEQ ID NO: 4). Methods of determining spatial conformation of epitopes include, for example, x-ray crystallography and 2-dimensional nuclear magnetic resonance. See, for example, "Epitope Mapping Protocols" in Methods in Molecular Biology, Vol. 66, Glenn E. Morris, Ed (1996).

Framework Region: Amino acid sequences interposed between CDRs, and includes variable light and variable heavy framework regions. The framework regions serve to hold the CDRs of an antibody or fragment thereof in an appropriate orientation for antigen binding.

Hepatocellular carcinoma (HCC): A malignant collection of abnormal and uncontrollably growing cells that derive from hepatocytes, the epithelial cells of the liver. Risk factors for development of liver cancer include chronic infection with the hepatitis B or C virus and cirrhosis (scarring of the liver). HCC can be a primary tumor, an HCC tumor that has metastasized to another part of the body, or can result from a metastasis to the liver from another part of the body (such as from colon, stomach, skin or ovarian cancer).

Immunoconjugate: A covalent linkage of an effector molecule to an antibody, such as 5kd106-13D antibody. The effector molecule can be a detectable label or a therapeutic molecule.

A "chimeric molecule" is a targeting moiety, such as a ligand or an antibody, conjugated (coupled) to an effector molecule. The term "conjugated" or "linked" refers to making two polypeptides into one contiguous polypeptide molecule. In one embodiment, an antibody is joined to an effector molecule (EM). In another embodiment, an antibody joined to an effector molecule is further joined to a lipid or other molecule to a protein or peptide to increase its half-life in the body. The linkage can be either by chemical or recombinant means. In one embodiment, the linkage is chemical, wherein a reaction between the antibody moiety and the effector molecule has produced a covalent bond formed between the two molecules to form one molecule. A peptide linker (short peptide sequence) can optionally be included between the antibody and the effector molecule. Because immunoconjugates were originally prepared from two molecules with separate functionalities, such as an antibody and an effector molecule, they are also sometimes referred to as "chimeric molecules."

Immunologically reactive conditions: Includes reference to conditions which allow an antibody raised against a particular epitope (e.g., EELNGAY, amino acids 30 to 36 of SEQ ID NO: 4) to bind to that epitope (or cell expressing the epitope) to a detectably greater degree than, and/or to the substantial exclusion of, binding to substantially all other epitopes (or cells not expressing the epitope). Immunologically reactive conditions are dependent upon the format of the antibody binding reaction and typically are those utilized in immunoassay protocols or those conditions encountered in vivo. See Harlow & Lane (*Antibodies: A Laboratory Manual.* 1988) for a description of immunoassay formats and conditions. The immunologically reactive conditions employed in the methods are "physiological conditions" which include reference to conditions (such as temperature, osmolarity, pH) that are typical inside a living mammal or a mammalian cell. While it is recognized that some organs are subject to extreme conditions, the intra-organismal and intracellular environment normally lies around pH 7 (e.g., from pH 6.0 to pH 8.0, more typically pH 6.5 to 7.5), contains water as the predominant solvent, and exists at a temperature above 0° C. and below 50° C. Osmolarity is within the range that is supportive of cell viability and proliferation.

Isolated: An "isolated" biological component (such as a nucleic acid molecule, protein, antibody, or cell) has been substantially separated or purified away from other components, such as other components in the cell of the organism, or the organism itself, in which the component occurs, such as other chromosomal and extra-chromosomal DNA and RNA, proteins and cells. Nucleic acid molecules and proteins that have been "isolated" include nucleic acid molecules (such as DNA or RNA) and proteins purified by standard purification methods. The term also embraces nucleic acid molecules and proteins prepared by recombinant expression in a host cell as well as chemically synthesized nucleic acid molecules and proteins. For example, an isolated antibody is one that is substantially separated from the animal or cells in which it was generated, or from cell culture medium.

Label: A detectable compound or composition that is conjugated directly or indirectly to another molecule, such as an antibody (e.g., 5kd106-13D) or a protein, to facilitate detection of that molecule. For example, the label can be capable of detection by ELISA, spectrophotometry, flow cytometry, or microscopy. Specific, non-limiting examples of labels include fluorophores, chemiluminescent agents, enzymatic linkages, electron-dense compounds, haptens and radioactive isotopes. Methods for labeling and guidance in the choice of labels appropriate for various purposes are discussed for example in Sambrook et al. (Molecular Cloning: A Laboratory Manual, Cold Spring Harbor, N.Y., 1989) and Ausubel et al. (In Current Protocols in Molecular Biology, John Wiley & Sons, New York, 1998).

Linker peptide: A peptide within an antibody binding fragment (such as an Fv fragment, for example a 5kd106-13D antibody fragment) which serves to indirectly bond the variable heavy chain to the variable light chain. "Linker" can also refer to a peptide serving to link a targeting moiety, such as a scFv, to an effector molecule, such as a cytotoxin or a detectable label.

The terms "conjugating," "joining," "bonding" or "linking" refer to making two polypeptides into one contiguous polypeptide molecule, or to covalently attaching a radionuclide or other molecule to a polypeptide, such as an scFv. In the specific context, the terms include reference to joining a ligand, such as an antibody moiety, to an effector molecule ("EM"). The linkage can be either by chemical or recombinant means. "Chemical means" refers to a reaction between the antibody moiety and the effector molecule such that there is a covalent bond formed between the two molecules to form one molecule.

Malignant: Cells which have the properties of anaplasia invasion and metastasis.

Matrix metalloproteinase-9 (MMP-9): A member of the metalloproteinase family, also referred to as gelatinase B. It is called a gelatinase because it has a high affinity for digestion of denatured collagen I. MMP-9 can also cleave a variety of proteins including many components of the extracellular matrix such as collagens I, III, IV, and V, entactin, and elastin. MMP-9 is frequently up-regulated in cancer cells and also in the adjacent host tissues, and its expression by tumor cells contributes to metastasis.

MMP-9 has a signal peptide that leads to its secretion, but the secreted molecule is not itself enzymatically active. MMP-9 has a proregion adjacent to the signal peptide. The proregion contains a signature sequence including an unpaired cysteine that interacts with the $Zn^{2+}$ that is complexed with three histidines to form the active site. This interaction allows the proregion to act as a competitive inhibitor of MMP-9. Hence, the proregion is cleaved and dissociated to allow enzymatic activity MMP-9 has been cloned from a variety of organisms, and nucleic acid and protein sequences are publicly available, for example from GenBank and EMBL (for example GenBank Accession Nos. CAC07541.1; NP_038627.1; P14780.2; and NM_004994.2). Human MMP-9 protein is Mr 92,000 although the murine form is Mr 105,000 because of an insert of an additional 24 amino acids.

Neoplasm: Abnormal growth of cells.

Normal cells: Non-tumor, non-malignant cells.

Osteopontin (OPN, SPP1): A secreted multi-functional phosphorylated glycoprotein expressed at high levels in tumors and the surrounding stroma of numerous cancers, including those of the liver. OPN proteins contain a functional Gly-Arg-Gly-Asp-Ser (GRGDS; amino acids 158-162 of SEQ ID NO: 2) cell-binding sequence.

Several splice variants of OPN have been identified, including OPN-a (native sequence) and OPN-c (truncated sequence). OPN-c lacks exon 4 (27 amino acids) in the $NH_2$-terminal region of the mature sequence. OPN-c includes a transglutaminase reactive domain (Gly-X-Gly) which can mediate covalent homodimer cross-linking as well as heterodimer formation to other matrix components (such as fibronectin).

The term osteopontin includes any osteopontin gene, cDNA, mRNA, or protein from any organism that retains OPN biological activity. OPN sequences are publicly available. For example, GenBank Accession Nos: D28759 (nucleic acid) and BAA05949 (protein) disclose human OPN-a sequences, and GenBank Accession Nos: D2876 (nucleic acid) and BAA05951 (protein) disclose human OPN-c sequences.

In certain examples, OPN has at least 80% sequence identity, for example at least 85%, at least 90%, at least 95%, or at least 98% sequence identity to a native OPN and retain OPN biological activity. In other examples, an OPN nucleic acid sequence has a sequence that hybridizes under very high stringency conditions to a sequence set forth in GenBank Accession No. D28759 or D2876 and retains OPN activity.

OPN-5kD or OPN-5kD fragment: One of three osteopontin peptide fragments generated when exposed to MMP-9 (when run on a SDS gel this peptide can migrate at approximately 10 kD, however, its predicted size based upon amino acid sequence is 5 kD). This peptide binds to the CD44 receptor, thereby enhancing cellular invasion of HCC cells. A particular example of an OPN-5kD sequence is provided in SEQ ID NO: 4. Methods of diagnosing a tumor (such as an OPN-c overexpressing tumor) by detecting OPN-5kD fragment, are provided herein. Peptide fragments of OPN-5kD are provided herein, and can be used for example to treat an OPN-overexpressing tumor or to generate antibodies. Peptide fragments of OPN-5kD include at least 5 contiguous amino acids of SEQ ID NO: 4). Specific examples of peptide fragments of OPN-5kD include peptides of 5 to 60 or 5 to 50 amino acids in length (such as 5 to 25, 5 to 20, 5 to 15, 6 to 12, 8 to 10, 10 to 44, 10 to 20, or 10 to 15 amino acids) and have least 5 contiguous amino acids of an OPN-5kD sequence (e.g., SEQ ID NO: 4), such as 5, 6, 7, 8, 9, 10, 11, 12, 13, 14, 115, 16, 17, 18, 19, or 20 contiguous amino acids, such as 5 to 15 or 10 to 15 contiguous amino acids. Particular examples of peptide fragments of OPN5-kD are shown in SEQ ID NOS: 5-8 and amino acids 30-36 of SEQ ID NO: 4.

Peptide: A chain of amino acids of which is at least 4 amino acids in length, regardless of post-translational modification (such as glycosylation or phosphorylation). In one example, a peptide is at least 6 amino acids in length, such as at least 8, at least 9, at least 10, at least 11, or at least 12 amino acids in length. In particular examples, a peptide is 4 to 30 amino acids in length, for example 5 to 25 amino acids in length, 5 to 20 amino acids in length, 9 to 15 amino acids in length, or 9 to 10 amino acids in length.

Pharmaceutically Acceptable Carriers: The pharmaceutically acceptable carriers (vehicles) useful in this disclosure are conventional. *Remington's Pharmaceutical Sciences*, by E. W. Martin, Mack Publishing Co., Easton, Pa., 15th Edition (1975), describes compositions and formulations suitable for pharmaceutical delivery of one or more therapeutic agents, such as one or more compositions that include (1) a peptide fragment of OPN-5kD or (2) an OPN-5kD specific antibody (e.g., 5kd106-13D).

In general, the nature of the carrier will depend on the particular mode of administration being employed. For instance, parenteral formulations can include injectable fluids that include pharmaceutically and physiologically acceptable fluids such as water, physiological saline, balanced salt solutions, aqueous dextrose, glycerol or the like as a vehicle. In addition to biologically-neutral carriers, pharmaceutical compositions to be administered can contain minor amounts of nontoxic auxiliary substances, such as wetting or emulsifying agents, preservatives, and pH buffering agents and the like, for example sodium acetate or sorbitan monolaurate, sodium lactate, potassium chloride, calcium chloride, and triethanolamine oleate.

Promoter: An array of nucleic acid control sequences which direct transcription of a nucleic acid. A promoter includes necessary nucleic acid sequences near the start site of transcription, such as, in the case of a polymerase II type promoter, a TATA element. A promoter also optionally includes distal enhancer or repressor elements which can be located as much as several thousand base pairs from the start site of transcription. Promoters may be constitutive or inducible.

Purified: The term "purified" does not require absolute purity; rather, it is intended as a relative term. Thus, for example, a purified peptide is one in which the peptide is more pure than the peptide in its natural environment, such as within a cell.

In particular examples, purified OPN peptides or fragments thereof (such as SEQ ID NOS: 4-8) refers to peptides that are at least 75% pure, at least 80% pure, at least 90% pure, at least 95% pure, at least 97% pure, at least 98% pure, or at least 99% pure. The purity of a peptide can be measured using methods known in the art, such as by a Western blot.

Radiological agent: In cancer treatment, refers to the administration of one or a combination of radioactive compounds to damage the DNA of cells, thereby killing or slowing the reproduction of rapidly multiplying cells. Exemplary methods of administering radiological agents to a subject include external beam radiotherapy (XBRT) or teletherapy, brachytherapy or sealed source radiotherapy, and unsealed source radiotherapy. The radiological agents that can be administered to a subject in combination with the disclosed therapies that include a peptide of 5 to 50 amino acids in length that includes at least 5 contiguous amino acids of OPN-5kD (such as at least 9 contiguous amino acids of SEQ ID NO: 4) or OPN-5kD antibodies. Exemplary radiological agents include those known by those skilled in the art, such as ionizing radiation (for example x-rays and gamma rays).

Recombinant: A recombinant nucleic acid is one that has a sequence that is not naturally occurring or has a sequence that is made by an artificial combination of two otherwise separated segments of sequence. This artificial combination can for example, be accomplished by chemical synthesis or by the artificial manipulation of isolated segments of nucleic acids, such as by genetic engineering techniques. Similarly, a recombinant protein is one encoded for by a recombinant nucleic acid molecule.

Sample: Includes biological samples that contain cells, genomic DNA, RNA, or proteins (or combinations thereof) obtained from a subject, such as those present in peripheral blood (or a fraction thereof such as plasma or serum), urine, saliva, tissue biopsy, surgical specimen, fine needle aspirate, and autopsy material. In a particular example, a sample is obtained from a subject having or suspected of having a metastatic HCC.

Sequence identity: The identity between two or more nucleic acid sequences, or two or more amino acid sequences, is expressed in terms of the identity or similarity between the sequences. Sequence identity can be measured in terms of percentage identity; the higher the percentage, the more identical the sequences are. Sequence similarity can be measured in terms of percentage similarity (which takes into account conservative amino acid substitutions); the higher the percentage, the more similar the sequences are. Homologs or orthologs of nucleic acid or amino acid sequences possess a relatively high degree of sequence identity/similarity when aligned using standard methods.

Methods of alignment of sequences for comparison are well known in the art. Various programs and alignment algorithms are described in: Smith & Waterman, *Adv. Appl. Math.* 2:482, 1981; Needleman & Wunsch, *J. Mol. Biol.* 48:443, 1970; Pearson & Lipman, *Proc. Natl. Acad. Sci. USA* 85:2444, 1988; Higgins & Sharp, *Gene*, 73:237-44, 1988; Higgins & Sharp, CABIOS 5:151-3, 1989; Corpet et al., *Nuc. Acids Res.* 16:10881-90, 1988; Huang et al. *Computer Appls. in the Biosciences* 8, 155-65, 1992; and Pearson et al., *Meth. Mol. Bio.* 24:307-31, 1994. Altschul et al., *J. Mol. Biol.* 215: 403-10, 1990, presents a detailed consideration of sequence alignment methods and homology calculations.

The NCBI Basic Local Alignment Search Tool (BLAST) (Altschul et al., *J. Mol. Biol.* 215:403-10, 1990) is available from several sources, including the National Center for Biological Information (NCBI, National Library of Medicine, Building 38A, Room 8N805, Bethesda, Md. 20894) and on the Internet, for use in connection with the sequence analysis programs blastp, blastn, blastx, tblastn and tblastx. Additional information can be found at the NCBI web site.

BLASTN is used to compare nucleic acid sequences, while BLASTP is used to compare amino acid sequences. To compare two nucleic acid sequences, the options can be set as follows: -i is set to a file containing the first nucleic acid sequence to be compared (such as C:\seq1.txt); -j is set to a file containing the second nucleic acid sequence to be compared (such as C:\seq2.txt); -p is set to blastn; -o is set to any desired file name (such as C:\output.txt); -q is set to -1; -r is set to 2; and all other options are left at their default setting. For example, the following command can be used to generate an output file containing a comparison between two sequences: C:\Bl2seq-i c:\seq1.txt-j c:\seq2.txt-p blastn-o c:\output.txt-q-1-r 2.

To compare two amino acid sequences, the options of Bl2seq can be set as follows: -i is set to a file containing the first amino acid sequence to be compared (such as C:\seq1.txt); -j is set to a file containing the second amino acid sequence to be compared (such as C:\seq2.txt); -p is set to blastp; -o is set to any desired file name (such as C:\output.txt); and all other options are left at their default setting. For example, the following command can be used to generate an output file containing a comparison between two amino acid sequences: C:\Bl2seq-i c:\seq1.txt-j c:\seq2.txt-p blastp-o c:\output.txt. If the two compared sequences share homology, then the designated output file will present those regions of homology as aligned sequences. If the two compared sequences do not share homology, then the designated output file will not present aligned sequences.

Once aligned, the number of matches is determined by counting the number of positions where an identical nucleotide or amino acid residue is presented in both sequences. The percent sequence identity is determined by dividing the number of matches either by the length of the sequence set forth in the identified sequence, or by an articulated length (such as 100 consecutive nucleotides or amino acid residues from a sequence set forth in an identified sequence), followed by multiplying the resulting value by 100. For example, a nucleic acid sequence that has 1166 matches when aligned with a test sequence having 1154 nucleotides is 75.0 percent identical to the test sequence (1166÷1554*100=75.0). The percent sequence identity value is rounded to the nearest tenth. For example, 75.11, 75.12, 75.13, and 75.14 are rounded down to 75.1, while 75.15, 75.16, 75.17, 75.18, and 75.19 are rounded up to 75.2. The length value will always be an integer. In another example, a target sequence containing a 20-nucleotide region that aligns with 20 consecutive nucleotides from an identified sequence as follows contains a region that shares 75 percent sequence identity to that identified sequence (that is, 15÷20*100=75).

For comparisons of amino acid sequences of greater than about 30 amino acids, the Blast 2 sequences function is employed using the default BLOSUM62 matrix set to default parameters, (gap existence cost of 11, and a per residue gap cost of 1). Homologs are typically characterized by possession of at least 70% sequence identity counted over the full-length alignment with an amino acid sequence using the NCBI Basic Blast 2.0, gapped blastp with databases such as the nr or swissprot database. Queries searched with the blastn program are filtered with DUST (Hancock and Armstrong, 1994, *Comput. Appl. Biosci.* 10:67-70). Other programs use SEG. In addition, a manual alignment can be performed. Proteins with even greater similarity will show increasing percentage identities when assessed by this method, such as at least 75%, at least 80%, at least 85%, at least 90%, at least 95%, at least 98%, or at least 99% sequence identity. For example, a peptide having substantial sequence identity to an OPN-5kD sequence can share at least 80% sequence identity to SEQ ID NO: 4, such as at least 90% or at least 95% sequence identity to SEQ ID NO: 4.

When aligning short peptides (fewer than around 30 amino acids), the alignment can be performed using the Blast 2 sequences function, employing the PAM30 matrix set to default parameters (open gap 9, extension gap 1 penalties). For example, when less than the entire sequence is being compared for sequence identity, homologs will typically possess at least 75% sequence identity over short windows of 10-20 amino acids, and can possess sequence identities of at least 85%, at least 90%, at least 95% or at least 98% depending on their identity to the reference sequence. For example, a peptide having substantial sequence identity to an OPN-5kD fragment can share at least 80% sequence identity to any of SEQ ID NOS: 5-8, such as at least 90%, at least 95%, at least 98%, or at least 99% sequence identity to SEQ ID NOS: 5-8. Methods for determining sequence identity over such short windows are described at the NCBI web site.

One indication that two nucleic acid molecules are closely related is that the two molecules hybridize to each other under stringent conditions, as described above. Nucleic acid sequences that do not show a high degree of identity may nevertheless encode identical or similar (conserved) amino acid sequences, due to the degeneracy of the genetic code. Changes in a nucleic acid sequence can be made using this degeneracy to produce multiple nucleic acid molecules that all encode substantially the same protein. Such homologous nucleic acid sequences can, for example, possess at least 60%, at least 70%, at least 80%, at least 90%, at least 95%, at least 98%, or at least 99% sequence identity determined by this method. For example, a nucleic acid encoding an OPN-5kD sequence can have substantial sequence identity to a native sequence if it shares at least 80% sequence identity to nucleotides 566-697 of SEQ ID NO: 1, such as at least 90% or at least 95% sequence identity to nucleotides 566-697 of SEQ ID NO: 1. An alternative (and not necessarily cumulative) indication that two nucleic acid sequences are substantially identical is that the peptide which the first nucleic acid sequence encodes is immunologically cross reactive with the peptide encoded by the second nucleic acid sequence.

One of skill in the art will appreciate that the particular sequence identity ranges are provided for guidance only; it is possible that strongly significant homologs could be obtained that fall outside the ranges provided.

Specific binding agent: An agent that binds substantially only to a defined target. Thus an OPN-5kD specific binding agent is an agent that binds substantially to a OPN-5kD peptide or epitope thereof. In one example, the specific binding agent is an antibody that specifically binds the OPN-5kD peptide.

The term "specifically binds" refers, with respect to an antigen such as OPN-5kD, to the preferential association of an antibody or other specific binding agent, in whole or part, to the antigen and not to other antigens. A certain degree of non-specific interaction can occur between a specific binding agent and a non-target antigen. Nevertheless, specific binding can be distinguished as mediated through specific recognition of the antigen. Specific binding results in a significant association between the antibody (or other specific binding agent) and the antigen than between the antibody and a non-antigen. Specific binding typically results in greater than 2-fold, such as greater than 5-fold, greater than T0-fold, or greater than 100-fold increase in amount of bound antibody or other specific binding agent to the antigen as compared to binding to a non-specific antigen.

The determination that a particular agent binds substantially only to OPN-5kD can be made using or adapting routine procedures. For example, western blotting can be used to determine that a specific binding agent, such as an antibody, binds substantially only to the protein (such as substantially only binds OPN-5kD but not to other proteins, such as those found in blood) (for example see Harlow and Lane, *Antibodies: A Laboratory Manual.* 1988). A variety of immunoassay formats are appropriate for selecting antibodies or other specific binding agent specifically immunoreactive with a particular protein (such as OPN-5kD). For example, solid-phase ELISA immunoassays are routinely used to select monoclonal antibodies specifically immunoreactive with a protein.

Subject: Living multi-cellular vertebrate organisms, a category that includes human and non-human mammals (such as laboratory or veterinary subjects).

Therapeutically effective amount: An amount of a therapeutic agent (such as an OPN-5kD specific antibody, or an OPN-5kD peptide fragment (such as a peptide of 5 to 50 amino acids in length that includes at least 5 contiguous amino acids of OPN-5kD), that alone, or together with one or more additional therapeutic agents, induces the desired response, such as treatment of a tumor that overexpresses OPN, such as a metastatic HCC tumor. In one example, it is an amount of an OPN-5kD specific antibody, or one or more peptide fragments of OPN-5kD needed to prevent or delay the development of a tumor, prevent or delay the metastasis of a tumor, cause regression of an existing tumor, or treat one or more signs or symptoms associated with a tumor, in a subject, such as a subject having HCC. Ideally, a therapeutically effective amount provides a therapeutic effect without causing a substantial cytotoxic effect in the subject. The preparations disclosed herein are administered in therapeutically effective amounts.

In one example, a desired response is to decrease the size, volume, or number (such as metastases) of a tumor that overexpresses OPN, such as HCC. For example, the therapeutic compositions can decrease the size, volume, or number of tumors (such as HCC) by a desired amount, for example by at least 5%, at least 10%, at least 15%, at least 20%, at least 25%, at least 30%, at least 50%, at least 75%, or even at least 90%, as compared to a response in the absence of the composition.

The effective amount of a composition that includes an OPN-5kD specific antibody, or one or more peptide fragments of OPN-5kD, that is administered to a human or veterinary subject will vary depending upon a number of factors associated with that subject, for example the overall health of the subject. An effective amount of a composition can be determined by varying the dosage of the product and measuring the resulting therapeutic response, such as the regression of a tumor. Effective amounts also can be determined through various in vitro, in vivo or in situ immunoassays. The disclosed therapeutic agents can be administered in a single dose, or in several doses, as needed to obtain the desired response. However, the effective amount of can be dependent on the source applied, the subject being treated, the severity and type of the condition being treated, and the manner of administration.

In particular examples, a therapeutically effective dose of one or more peptide fragments of OPN-5kD or an OPN-5kD antibody includes at least 1 µg daily (such as 1-100 µg or 5-50 µg) if administered via injection, or at least 1 mg daily if administered topically (such as 1-100 mg or 5-50 mg) of one or more peptides fragments of OPN-5kD or an OPN-5kD antibody. In particular examples, such daily dosages are administered in one or more divided doses (such as 2, 3, or 4 doses) or in a single formulation.

The disclosed compositions that include one or more peptide fragments of OPN-5kD or an OPN-5kD antibody can be administered alone, in the presence of a pharmaceutically acceptable carrier, in the presence of other therapeutic agents (such as other anti-neoplastic agents), or both.

Transgene: An exogenous gene introduced into a cell.

Treating or treatment: Refers to a therapeutic intervention that ameliorates a sign or symptom of a disease or pathological condition related to a disease (such as a tumor, for example HCC). Treatment can also induce remission or cure of a condition, such as a tumor. In particular examples, treatment includes preventing a tumor, for example by inhibiting the full development of a tumor, such as preventing development of a metastasis or the development of a primary tumor. Prevention does not require a total absence of a tumor.

Reducing a sign or symptom associated with a tumor (such as a tumor that overexpresses OPN, for example HCC) can be evidenced, for example, by a delayed onset of clinical symptoms of the disease in a susceptible subject (such as a subject having HCC which has not yet metastasized), a reduction in severity of some or all clinical symptoms of the disease, a slower progression of the disease (for example by prolonging the life of a subject having tumor), a reduction in the number of relapses of the disease, an improvement in the overall health or well-being of the subject, or by other parameters well known in the art that are specific to the particular tumor.

Tumor: A neoplasm.

Under conditions sufficient for: A phrase that is used to describe any environment that permits the desired activity.

In one example, includes administering a therapeutically effective amount of a composition that includes an OPN-5kD specific antibody or one or more peptides fragments of OPN-5kD sufficient to allow the desired activity. In particular examples the desired activity is treatment of a tumor, such as a tumor that expresses OPN, for example HCC.

Unit dose: A physically discrete unit containing a predetermined quantity of an active material calculated to individually or collectively produce a desired effect, such as a therapeutic effect. A single unit dose or a plurality of unit doses can be used to provide the desired effect, such as treatment of a tumor, for example a metastatic HCC. In one example, a unit dose includes a desired amount of an agent that decreases cellular invasion induced by OPN-5kD binding to CD44.

Vector: A nucleic acid molecule as introduced into a host cell, thereby producing a transformed host cell. A vector can include nucleic acid sequences that permit it to replicate in the host cell, such as an origin of replication. A vector may also include one or more therapeutic genes and/or selectable marker genes and other genetic elements known in the art. A vector can transduce, transform or infect a cell, thereby causing the cell to express nucleic acids and/or proteins other than those native to the cell. A vector optionally includes materials to aid in achieving entry of the nucleic acid into the cell, such as a viral particle, liposome, protein coating or the like. In a particular example, a vector includes a nucleic acid molecule encoding one or more of SEQ ID NOS: 4-8 or a fragment of SEQ ID NO: 4.

Methods of Treating a Tumor

It is shown herein that MMP-9 liberates an OPN-5kD fragment, and that OPN-induced cellular invasion proceeds via binding of the OPN-5kD ligand to CD44 cell surface receptors. Without being bound to a particular theory, it is proposed that exposure of a non-RGD cryptic binding site region of OPN by extracellular proteolytic cleavage increases binding to cell surface CD44 receptors and mediates an invasive response, which is distinct and independent from integrin $\alpha V\beta 3$ function. It is also demonstrated herein that small peptide fragments of OPN-5kD (for example any of SEQ ID NOS: 5-8) effectively decrease or inhibit cellular invasion induced by OPN-5kD. Without being bound to a particular theory, it is proposed that these peptides structurally compete with OPN-5kD for available cell-surface CD44 docking sites, thereby decreasing cellular invasion. This observation also supports the use of antibodies directed to epitopes within the OPN-5kD peptide (such as amino acids 30-36 of SEQ ID NO: 4) as therapeutics. Based on these observations, methods of treating a tumor that overexpresses OPN, MMP-9, or both, are disclosed. These methods include administering peptides, antibodies, or combinations thereof, which effectively decrease or inhibit cellular invasion.

A particular example of an OPN-5kD sequence is provided in SEQ ID NO: 4. However, one skilled in the art will appreciate that variants of SEQ ID NO: 4 (such as allelic variations that may be present between individuals or organisms, which may include one or more substitutions, deletions, or insertions, or combinations thereof) can also be an OPN-5kD peptide, as long as such peptide retains the ability to bind CD44 receptor an stimulate cellular invasion of HCC cells (for example using the methods described in Examples 4-7). In a particular example, an OPN-5kD sequence is 40 to 50 amino acids in length (such as 40-48, 42-46, or 44 amino acids), and has at least 90% sequence identity to SEQ ID NO: 4, such as at least 92%, at least 95%, or at least 98% sequence identity to SEQ ID NO: 4. In one example, an OPN-5kD peptide is 40 to 50 amino acids in length and includes 1-8 conservative amino acid substitutions in SEQ ID NO: 4, such as 1, 2, 3, 4, 5, 6, 7 or 8 conservative amino acid substitutions in SEQ ID NO: 4.

Methods are disclosed herein for treating tumors, such as those that overexpress OPN, for example in combination with overexpression of MMP-9. In one example, increased expression of OPN or MMP-9 can be detected in serum or plasma obtained from a subject having such a tumor. For example, detection of OPN-5kD in the serum of a subject (for example at a level of at least twice that found in a subject not having a tumor), detection of increased levels of OPN-c in the tumor (for example relative to expression of OPN-c in adjacent non-tumor cells, or relative to expression of OPN-a in the tumor), or both, indicates that the subject can benefit from the disclosed therapies. In some examples, subjects are initially screened to determine if they have increased levels of OPN-5kD in their serum, whether they have a tumor that has increased expression of OPN-c (for example relative to adjacent non-tumor cells, or relative to expression of OPN-a), or combinations thereof. For example, the diagnostic methods provided herein can be used to screen subjects to determine if they are candidates for the disclosed therapies.

In some examples, the tumor is treated in vivo, for example in a mammalian subject, such as a human or veterinary subject. A tumor is an abnormal growth of tissue that results from excessive cell division. A particular example of a tumor is cancer. For example, the current application is useful for the treatment (such as the prevention or reduction of metastasis) of tumors (such as cancers). Exemplary tumors that can be treated using the disclosed methods include, but are not limited to: cancers of the liver, breast, colon, and prostate, including metastases of such tumors. For example, the tumor can be a tumor that overexpresses OPN (such as OPN-c), for example HCC, metastatic HCC, such as an intra-hepatic metastasis or an extra-hepatic metastasis.

Treatment of a tumor, such as HCC or metastatic HCC, can include preventing or delaying the development of the tumor in a subject (such as preventing metastasis of a tumor), and also includes reducing signs or symptoms associated with the presence of such a tumor (for example by reducing the size or volume of the tumor or a metastasis thereof). In a specific example, treatment includes reducing the growth of cells of the tumor, or even killing the tumor cells (for example by causing the cells to undergo apoptosis). Such reduced growth can in some examples decrease or slow metastasis of the tumor, or reduce the size or volume of the tumor. In one example, treatment of a tumor includes reducing the invasive activity of the tumor in the subject, for example by reducing the ability of the tumor to metastasize. In some examples, treatment using the methods disclosed herein prolongs the time of survival of the subject (e.g., increases survival time by at least 6 months, at least 9 months, at least 12 months, at least 2 years, at least 3 years, or even at least 5 years relative to the absence of the therapy).

In particular examples, the method includes administering to the subject a therapeutically effective amount of one or more agents that reduce cellular invasion resulting from the interaction between OPN-5kD and CD44 receptor, thereby treating the tumor. In particular examples, cellular invasion is reduced by at least 10% (such as at least 20%, at least 50%, or at least 90%), for example as compared to an amount of cellular invasion in the absence of the therapeutic agent. Examples of such agents include peptide fragments of OPN-5kD or antibodies specific to OPN-5kD (e.g., 5kd106-13D) that reduce the interaction between OPN-5kD and CD44 receptor and reduce cellular invasion. Further detail on the OPN-5kD antibodies that can be used therapeutically is provided below.

Particular examples of agents that can be used in the methods disclosed herein include therapeutic amounts of peptide fragments of OPN-5kD. Such fragments include peptides of 5 to 50 amino acids (such as 5 to 25, 10 to 44, 10 to 20, or 10 to 15 amino acids) that include at least 5 contiguous amino acids of an OPN-5kD sequence (e.g., SEQ ID NO: 4), such as at least 6, at least 7, at least 8, at least 8, at least 9, at least 10 or at least 15 contiguous amino acids of SEQ ID NO: 4, for example 5-20, 10-15, or 8-10 contiguous amino acids of SEQ ID NO: 4. For example, the therapeutic peptide can include or consist of 5, 6, 7, 8, 9, 10, 12, 15, 20, or 30 contiguous amino acids of SEQ ID NO: 4. In one example, the peptide fragment of OPN-5kD include or consists of the amino acid sequence of SEQ ID NO: 5, 6, 7, or 8 or amino acids 30-36 of SEQ ID NO: 4. One skilled in the art will appreciate that more than one peptide fragment of OPN-5kD can be used, such as one or more peptides consisting of SEQ ID NO: 5, 6, 7, or 8. In some examples the therapeutic peptide is a fusion peptide, such as a fusion peptide that includes any of SEQ ID NOS: 5-8.

Screening Subjects

Subjects that can benefit from the disclosed therapies include human and veterinary subjects. Subjects can be screened prior to initiating the disclosed therapies, for example to determine whether the subject has a tumor that overexpresses OPN, MMP-9, or both. The presence of a tumor that overexpresses OPN, MMP-9, or both indicates that the tumor can be treated using the methods provided herein.

In one example, the tumor (or a portion thereof, such as a fine needle aspirate or other biopsy sample) is analyzed using immunodetection methods. For example, the biological sample can be incubated with an antibody that specifically binds to OPN or to MMP-9, or both antibodies. The primary antibody can include a detectable label. For example, the primary antibody can be directly labeled, or the sample can be subsequently incubated with a secondary antibody that is labeled (for example with a fluorescent label). The label can then be detected, for example by microscopy, ELISA, flow cytometery, or spectrophotometry. In another example, the biological sample is analyzed by Western blotting for the presence of OPN or to MMP-9. In one example, a subject is screened by determining whether increased levels of the OPN-5kD fragment is present in their serum (for example relative to a level present in a serum sample from a subject not having a tumor), for example using an antibody that specifically binds OPN-5kD (such as those described in Example 9).

As an alternative to analyzing the sample for the presence of proteins, the presence of nucleic acids can be determined. For example, the biological sample can be incubated with primers that permit the amplification of OPN or to MMP-9, under conditions sufficient to permit amplification of OPN or to MMP-9. Exemplary methods include PCR and RT-PCR. In another example, the biological sample is incubated with probes that can bind to OPN or to MMP-9 nucleic acid (such as cDNA, genomic DNA, or RNA (such as mRNA)) under high stringency conditions. The resulting hybridization can then be detected using methods known in the art. In one example, a subject is screened by determining whether increased levels of OPN-c are present in the tumor (for example relative to a level present in adjacent non-tumor cells from the same subject, or relative to a level of OPN-a in the same tumor sample), for example detecting OPN-c (and in some examples also OPN-a) mRNA expression.

The presence of increased expression of OPN or MMP-9 indicates that the tumor overexpresses OPN or MMP-9 or both, and that the tumor is one that can be treated using the disclosed therapies. In one example, the presence of increased OPN-5kD in the serum, the presence of increased OPN-c in the tumor, or both, indicates that the subject has a tumor that can be treated using the disclosed therapies.

Administration

Methods of administration of the disclosed therapeutic agents are routine, and can be determined by a skilled clinician. For example, the disclosed therapies (such as peptide fragments of OPN-5kD and antibodies directed to an epitope of OPN-5kD) can be administered via injection (for example via embolization), orally, topically, transdermally, parenterally, or via inhalation or spray. In a particular example, a peptide consisting of 5 to 20 contiguous amino acids of OPN-5kD or an antibody specific for OPN-5kD (such as 5kd106-13D) is administered intravenously to a mammalian subject, such as a human.

The therapeutic compositions, such as those that include peptide fragments of OPN-5kD or antibodies specific for OPN-5kD, can further include one or more biologically active or inactive compounds (or both), such as anti-neoplastic agents and conventional non-toxic pharmaceutically acceptable carriers, respectively.

In a particular example, a therapeutic composition that includes a therapeutically effective amount of one or more agents that reduce cellular invasion due to the interaction of OPN-5kD with CD44 (such as peptide fragments of OPN-5kD or antibodies specific for OPN-5kD) further includes one or more biologically inactive compounds. Examples of such biologically inactive compounds include, but are not limited to: carriers, thickeners, diluents, buffers, preservatives, and carriers. The pharmaceutically acceptable carriers useful for these formulations are conventional (see Remington's Pharmaceutical Sciences, by E. W. Martin, Mack Publishing Co., Easton, Pa., 19th Edition (1995)). In general, the nature of the carrier will depend on the particular mode of administration being employed. For instance, parenteral formulations can include injectable fluids that include pharmaceutically and physiologically acceptable fluids such as water, physiological saline, balanced salt solutions, aqueous dextrose, glycerol or the like as a vehicle. For solid compositions (for example, powder, pill, tablet, or capsule forms), conventional non-toxic solid carriers can include, for example, pharmaceutical grades of mannitol, lactose, starch, or magnesium stearate. In addition to biologically-neutral carriers, pharmaceutical compositions to be administered can include minor amounts of non-toxic auxiliary substances, such as wetting or emulsifying agents, preservatives, and pH buffering agents and the like, for example sodium acetate or sorbitan monolaurate.

In a particular example, a therapeutic composition that includes a therapeutically effective amount of one or more agents that reduce cellular invasion due to the interaction of OPN-5kD with CD44 (such as peptide fragments of OPN-5kD or antibodies specific for OPN-5kD) further includes therapeutically effective amounts of one or more other biologically active compounds. Examples of biologically active compounds include, but are not limited to: anti-neoplastic agents (such as chemotherapeutics), antibiotics, alkylating agents, antioxidants, adjuvants, and so forth (such as those listed below under "additional treatments"). However, one skilled in the art will appreciate that peptide fragments of OPN-5kD or antibodies specific for OPN-5kD and the other biologically active compounds can also be administered separately (instead of in a single composition).

The therapeutically effective amount of the agents administered can vary depending upon the desired effects and the subject to be treated. In one example, the method includes daily administration of at least 1 µg of one or more peptide fragments of OPN-5kD to the subject (such as a human subject). In one example, a human is administered at least 1 µg of peptide daily or at least 1 mg peptide daily of one or more OPN-5kD fragments (such as one or more of SEQ ID NOS: 5-8), such as 10 µg to 100 µg daily, 100 µg to 1000 µg daily, for example 10 µg daily, 100 µg daily, or 1000 µg daily. For example the subject can receive at least 1 µg (such as 1 µg to 100 µg, 5 µg to 50 µg, or 1 µg to 1000 µg) intravenously of each of one or more OPN-5kD fragments (such as one or more of SEQ ID NOS: 5-8). In one example, the subject is administered at least 1 mg intramuscularly (for example in an extremity) or topically of each of one or more OPN-5kD fragments (such as one or more of SEQ ID NOS: 5-8). For example, a human can be administered at least 1 µg daily or at least 1 mg daily of one or more OPN-5kD fragments (such as one or more of SEQ ID NOS: 5-8), such as 10 µg to 100 µg daily, 100 µg to 1000 µg daily, for example 10 µg daily, 100 µg daily, or 1000 µg daily. In one example, the subject is administered at least 1 µg (such as 1 µg to 100 µg, 5 µg to 50 µg, or 1 µg to 1000 µg) intravenously of each of one or more OPN-5kD fragments (such as one or more of SEQ ID NOS: 5-8). In one example, the subject is administered at least 1 mg intramuscularly (for example in an extremity) or topically of each of one or more OPN-5kD fragments (such as one or more of SEQ ID NOS: 5-8). The dosage can be administered in divided doses (such as 2, 3, or 4 divided doses per day), or in a single dosage daily.

Therapeutic amounts of OPN-5kD specific antibodies disclosed herein (e.g., 5kd106-13D or a humanized form thereof, a chimeric form thereof, or a fragment thereof) can also be administered. In some examples, therapeutic amounts are amounts which eliminate or reduce the patient's tumor burden, or which prevent or reduce the proliferation of metastatic cells. The dosage will depend on many parameters, including the nature of the tumor, patient history, patient condition, the possible co-use of other oncolytic agents, and methods of administration. Methods of administration include injection (e.g., parenteral, subcutaneous, intravenous, intraperitoneal, etc.) for which the antibodies are provided in a nontoxic pharmaceutically acceptable carrier such as water, saline, Ringer's solution, dextrose solution, 5% human serum albumin, fixed oils, ethyl oleate, or liposomes. Typical dosages may range from about 0.01 to about 20 mg/kg, such as from about 0.1 to about 10 mg/kg. Other methods of administration include oral and transdermal (such as at least 1 mg, for example 1-1000 mg). Acceptable carriers for oral ingestion include pharmaceutically acceptable liquid carriers or pharmaceutically acceptable solid carriers in the form of tablets, capsules, caplets, or gel-seals. Other effective methods of administration and dosages may be determined by routine experimentation and are within the scope of this invention.

Therapeutic methods employing OPN-5kD specific antibodies or peptide fragments of OPN-5kD can be combined with chemotherapy, surgery, and radiation therapy, depending on type of the tumor, patient condition, other health issues, and a variety of factors. The methods can also include immunoconjugates for targeted immunotoxin-mediated therapy, wherein OPN-5kD antibodies are covalently or non-covalently conjugated to various cytotoxic agents, further enhancing toxicity to targeted cells. See, for example, U.S. Pat. No. 5,872,223. Such agents, including various bacterial toxins (e.g., *Pseudomonas* exotoxin), ricin A-chain, daunorubicin, methotrexate, and ribosome inhibitors (e.g., trichosantin). Also, OPN-5kD antibodies can be labeled with alpha, beta, or Auger electron emitters, resulting in immunoconjugates for targeted radiotherapy.

Thus, OPN-5kD specific antibodies can be used in a variety of methods and compositions for detecting and treating metastatic disease.

In particular examples, the subject is administered the therapeutic composition that includes OPN-5kD specific antibodies, or one or more peptide fragments of OPN-5kD, on a multiple daily dosing schedule, such as at least two consecutive days, 10 consecutive days, and so forth, for example for a period of weeks, months, or years. In one example, the subject is administered the therapeutic composition for a period of at least 30 days, such as at least 2 months, at least 4 months, at least 6 months, at least 12 months, at least 24 months, or at least 36 months.

Additional Treatments

In particular examples, prior to, during, or following administration of a therapeutic amount of an agent that reduces cellular invasion due to the interaction of OPN-5kD with CD44 (such as one or more peptide fragments of OPN-5kD or OPN-5kD antibodies), the subject can receive one or more other therapies. In one example, the subject receives one or more treatments to remove or reduce the tumor prior to administration of a therapeutic amount of one or more agents that reduce cellular invasion due to the interaction of OPN-5kD with CD44.

Examples of such therapies include, but are not limited to, surgical treatment for removal or reduction of the tumor (such as surgical resection, cryotherapy, or chemoembolization), as well as anti-tumor pharmaceutical treatments which can include radiotherapeutic agents, anti-neoplastic chemotherapeutic agents, antibiotics, alkylating agents and antioxidants, kinase inhibitors, and other agents. In one example, at least part of the tumor is surgically or otherwise excised or reduced in size or volume prior to administering the therapeutically effective amount of the antibody or peptide. Particular examples of additional therapeutic agents can that can be used include microtubule binding agents, DNA intercalators or cross-linkers, DNA synthesis inhibitors, DNA and/or RNA transcription inhibitors, antibodies, enzymes, enzyme inhibitors, gene regulators, and angiogenesis inhibitors. These agents (which are administered at a therapeutically effective amount) and treatments can be used alone or in combination. Methods and therapeutic dosages of such agents are known to those skilled in the art, and can be determined by a skilled clinician.

"Microtubule binding agent" refers to an agent that interacts with tubulin to stabilize or destabilize microtubule formation thereby inhibiting cell division. Examples of microtubule binding agents that can be used in conjunction with the disclosed therapy include, without limitation, paclitaxel, docetaxel, vinblastine, vindesine, vinorelbine (navelbine), the epothilones, colchicine, dolastatin 15, nocodazole, podophyllotoxin and rhizoxin. Analogs and derivatives of such compounds also can be used and are known to those of ordinary skill in the art. For example, suitable epothilones and epothilone analogs are described in International Publication No. WO 2004/018478. Taxoids, such as paclitaxel and docetaxel, as well as the analogs of paclitaxel taught by U.S. Pat. Nos. 6,610,860; 5,530,020; and 5,912,264 can be used.

Suitable DNA and/or RNA transcription regulators, including, without limitation, actinomycin D, daunorubicin, doxorubicin and derivatives and analogs thereof also are suitable for use in combination with the disclosed therapies.

DNA intercalators and cross-linking agents that can be administered to a subject include, without limitation, cisplatin, carboplatin, oxaliplatin, mitomycins, such as mitomycin C, bleomycin, chlorambucil, cyclophosphamide and derivatives and analogs thereof.

DNA synthesis inhibitors suitable for use as therapeutic agents include, without limitation, methotrexate, 5-fluoro-5'-deoxyuridine, 5-fluorouracil and analogs thereof.

Examples of suitable enzyme inhibitors include, without limitation, camptothecin, etoposide, formestane, trichostatin and derivatives and analogs thereof.

Suitable compounds that affect gene regulation include agents that result in increased or decreased expression of one or more genes, such as raloxifene, 5-azacytidine, 5-aza-2'-deoxycytidine, tamoxifen, 4-hydroxytamoxifen, mifepristone and derivatives and analogs thereof.

"Angiogenesis inhibitors" include molecules, such as proteins, enzymes, polysaccharides, oligonucleotides, DNA, RNA, and recombinant vectors, and small molecules that function to reduce or even inhibit blood vessel growth. Angiogenesis is implicated in most types of human solid tumors. Angiogenesis inhibitors are known in the art and examples of suitable angiogenesis inhibitors include, without limitation, angiostatin K1-3, staurosporine, genistein, fumagillin, medroxyprogesterone, suramin, interferon-alpha, metalloproteinase inhibitors, platelet factor 4, somatostatin, thrombospondin, endostatin, thalidomide, and derivatives and analogs thereof.

Exemplary kinase inhibitors include Gleevac, Iressa, and Tarceva that prevent phosphorylation and activation of growth factors.

Antibodies that can be used include Herceptin and Avastin that block growth factors and the angiogenic pathway.

Other therapeutic agents, for example anti-tumor agents, that may or may not fall under one or more of the classifications above, also are suitable for administration in combination with the disclosed therapies (such as those that include one or more peptide fragments of OPN-5kD or an OPN-5kD specific antibody). By way of example, such agents include adriamycin, apigenin, rapamycin, zebularine, cimetidine, and derivatives and analogs thereof.

In one example, the therapeutic peptide composition (such as OPN-5kD or peptide fragments thereof) or is injected into the subject in the presence of an adjuvant, thus generating an immune response to OPN-5kD wherein such immune response decreases OPN-5kD binding to CD44. An adjuvant is an agent that when used in combination with an immunogenic agent augments or otherwise alters or modifies a resultant immune response. In some examples, an adjuvant increases the titer of antibodies induced in a subject by the immunogenic agent. In one example, the one or more peptides are administered to the subject as an emulsion with IFA and sterile water for injection (for example an intravenous or intramuscular injection). Incomplete Freund's Adjuvant (Seppic, Inc.) can be used as the Freund's Incomplete Adjuvant (IFA) (Fairfield, N.J.). In some examples, IFA is provided in 3 ml of a mineral oil solution based on mannide oleate (Montanide ISA-51). At the time of injection, the peptide(s) is mixed with the Montanide ISA.51 and then administered to the subject. Other adjuvants can be used, for example, Freund's complete adjuvant, B30-MDP, LA-15-PH, montanide, saponin, aluminum hydroxide, alum, lipids, keyhole lympet protein, hemocyanin, a mycobacterial antigen, and combinations thereof.

In some examples, the subject receiving a therapeutic composition (such as one or more peptide fragments of OPN-5kD or OPN-5kD antibodies) is also administered interleukin-2

(IL-2), for example via intravenous administration. In particular examples, IL-2 (Chiron Corp., Emeryville, Calif.) is administered at a dose of at least 500,000 IU/kg as an intravenous bolus over a 15 minute period every eight hours beginning on the day after administration of the peptides and continuing for up to 5 days. Doses can be skipped depending on subject tolerance.

In some examples, the therapeutic compositions can be co-administered with a fully human antibody to cytotoxic T-lymphocyte antigen-4 (anti-CTLA-4). In some examples subjects receive at least 1 mg/kg anti-CTLA-4 (such as 3 mg/kg every 3 weeks or 3 mg/kg as the initial dose with subsequent doses reduced to 1 mg/kg every 3 weeks).

In one example, at least a portion of the tumor (such as a metastatic HCC) is surgically removed (for example via cryotherapy), irradiated, chemically treated (for example via chemoembolization) or combinations thereof, prior to administration of the disclosed therapies. For example, a subject having HCC can have all or part of the tumor surgically excised prior to administration of the disclosed therapies. In another particular example, the subject has HCC and is administered radiation therapy, chemoembolization therapy, or both, prior to administration of the disclosed therapies.

Therapeutic Compositions

Another aspect of the disclosure includes pharmaceutical compositions prepared for administration to a subject and which include a therapeutically effective amount of one or more of the currently disclosed compounds. Such compositions can also be part of a kit. For example, compositions that include a therapeutic amount of an agent that decreases or inhibits cellular invasion that results from the interaction of OPN-5kD with CD44 receptor can be formulated for use in treating a tumor that overexpresses OPN, such as HCC. Particular examples of such agents include OPN-5kD specific antibodies and peptide fragments of OPN-5kD, such as the peptide sequences shown in SEQ ID NOS: 5-8.

In one example, compositions include a therapeutic amount of one or more agents that decrease or inhibit tumor cellular invasion (for example a reduction of at least 10%, at least 20%, at least 50%, or even at least 90%) such as by decreasing the binding of OPN-5kD to the CD44 receptor. Such compositions can include one or more additional biologically active agents, one or more biologically inactive compounds, or combinations thereof. Examples of such biologically active agents are described above, and can include anti-neoplastic agents. Examples of biologically inactive agents are described above, and can include pharmaceutically acceptable carriers. In a specific example, the therapeutic composition includes an antibody to cytotoxic T-lymphocyte antigen-4 (anti-CTLA-4).

Particular examples of agents that can be used in the disclosed compositions include peptide fragments of OPN-5kD that decrease tumor cellular invasion resulting from the interaction of OPN-5kD with CD44 receptor. One example of OPN-5kD peptide fragments includes peptides of 5 to 60 amino acids that have at least 5 contiguous amino acids of OPN-5kD (such as at least 5 contiguous amino acids of SEQ ID NO: 4), such as at least 6, at least 7, at least 8, at least 9, at least 10, at least 12, at least 15, or even at least 20 contiguous amino acids of OPN-5kD, for example 5-30, 5-25, 6-20, 6-12, or 8-10 contiguous amino acids of OPN-5kD (such as this number of contiguous amino acids of SEQ ID NO: 4). Exemplary examples of such peptides are shown in SEQ ID NOS: 5-8.

In a particular example, the composition includes at least two peptide fragments of OPN-5kD. For example, the composition can include a mixture of at least 2 of the peptides shown in SEQ ID NOS: 5-8, such as a composition that includes 2, 3, or 4 of these peptides. Exemplary combinations include the peptides shown in SEQ ID NOS: 5 and 6, SEQ ID NOS: 5 and 7, SEQ ID NOS: 5 and 8, SEQ ID NOS: 6 and 7, SEQ ID NOS: 6 and 8, SEQ ID NOS: 7 and 8, SEQ ID NOS: 5, 6, and 7, SEQ ID NOS: 5, 6, and 8, SEQ ID NOS: 5, 7, and 8, SEQ ID NOS: 6, 7, and 8, or SEQ ID NOS: 5, 6, 7, and 8. In one example, the composition includes one or more peptides consisting of the amino acid sequence shown in SEQ ID NO: 5, 6, 7, or 8.

In particular examples, the composition includes 1-1000 µg of one or more peptide fragments of OPN-5kD that decrease tumor cellular invasion resulting from the interaction of OPN-5kD with CD44 receptor, such as 1-1000 µg of one or more of SEQ ID NOS: 5-8. In some examples, the composition includes 1-1000 mg of one or more peptide fragments of OPN-5kD that decrease tumor cellular invasion resulting from the interaction of OPN-5kD with CD44 receptor, such as 1-1000 mg of one or more of SEQ ID NOS: 5-8.

In another particular example, the composition includes one or more OPN-5kD specific antibodies, such as 5kd106-13D (or other monoclonal antibody or humanized form thereof that recognizes the epitope shown in amino acids 30-36 of SEQ ID NO: 4). Such antibodies bind to OPN-5kD or fragments thereof and inhibit or decrease binding to CD44 receptors. In particular examples, the composition includes 1-1000 µg or 1-1000 mg of one or more OPN-5kD specific antibodies that decrease tumor cellular invasion resulting from the interaction of OPN-5kD with CD44 receptor. Details on such antibodies are provided below.

Methods of Diagnosing and Prognosing a Tumor

Metastasis is a major complication in the pathogenesis of tumors, such as HCC, and is typically indicative of poor prognosis. It is shown herein that OPN-5kD abundance in HCC cell lines correlates with degree of metastatic potential. Without wishing to be bound to a particular theory, it is proposed that the interaction of OPN and MMP-9 is related to enhanced HCC tumor cell metastasis. The abundance of the OPN-5kD fragment in HCC cells correlates to degree of metastatic potential. It is also shown herein that OPN-c mRNA expression correlates with metastatic HCC but not non-metastatic HCC in non-cancerous tissue adjacent to primary HCC lesions. Based on these observations, methods of diagnosing or prognosing a tumor that overexpresses OPN, MMP-9, or both, based on detecting OPN-5kD, OPN-c, or both, are disclosed. In some examples, such methods can be used to identify those subjects that will benefit from the disclosed treatment methods. For example, such diagnostic methods can be performed prior to the subject undergoing the treatments described herein.

In some examples the method is performed in vitro, for example when the biological sample is removed from the subject. In some examples the method is carried out in vivo for example by administering the disclosed antibodies, humanized form thereof or fragment thereof to a subject, such as a subject that has or is suspected of having an OPN-expressing tumor, such as HCC.

In one example, detection of the OPN-5kD fragment (such as SEQ ID NO: 4 or a variant thereof, such as a polymorphism thereof) in a biological sample from the subject is used to diagnose or prognose a tumor that overexpresses OPN, MMP-9, or both (such as HCC). Methods of detecting a peptide in a sample, such as OPN-5kD, are known in the art and are routine. In some examples, the relative amount of OPN-5kD present is determined, for example by quantitating the amount of OPN-5kD present. For example, the relative or absolute quantity of OPN-5kD in a sample can be determined.

In another example, detection of OPN-c mRNA (such as an mRNA corresponding to SEQ ID NO: 3 or 9, or a variant thereof, such as a polymorphism thereof) in a biological sample from the subject is used to diagnose or prognose a tumor that overexpresses OPN, MMP-9, or both (such as metastatic HCC). Methods of detecting a nucleic acid molecule in a sample, such as OPN-c, are known in the art and are routine. In some examples, the relative amount of OPN-c mRNA present is determined, for example by quantitating the amount of OPN-c mRNA present. For example, the relative or absolute quantity of OPN-c mRNA in a sample can be determined. However, one skilled in the art will recognize that OPN-c protein can be detected as an alternative to detecting OPN-c nucleic acid molecules. In some examples, OPN-c expression is measured in a tumor sample and an adjacent non-tumor sample, wherein an increase in OPN-c expression (such as an increase of at least 2-fold, at least 3-fold, or at least 5-fold) in the tumor sample relative to OPN-c expression in the non-tumor sample indicates that the subject has a tumor with increased metastatic potential. In other examples, OPN-c and OPN-a expression are measured in the tumor sample, wherein an increase in OPN-c expression (such as an increase of at least 2-fold, at least 3-fold, or at least 5-fold) relative to OPN-a expression in the tumor sample indicates that the subject has an OPN-overexpressing tumor.

In some examples, detection of both OPN-5kD protein and OPN-c mRNA (an in some examples also OPN-a mRNA) in one or more biological samples obtained from the subject (such as serum or a tumor sample or adjacent non-tumor sample) are used to diagnose or prognose a tumor that overexpresses OPN, MMP-9, or both (such as metastatic HCC).

Biological Samples

A biological sample is typically obtained from a mammal, such as a rat, mouse, cow, dog, guinea pig, rabbit, or primate, such as a human. Thus is some examples a subject, such as a human subject, is selected and a biological sample from that subject is tested for the presence of an OPN-expressing tumor (for example by detecting OPN-5kD, OPN-c, and/or OPN-a). Methods of obtaining a biological sample from a subject are known in the art. For example, methods of obtaining a blood sample or a fraction thereof (such as serum) are routine. Similarly, a sample from a tumor (or adjacent non-tumor tissue) that contains cellular material can be obtained by surgical excision of all or part of the tumor, by collecting a fine needle aspirate from the tumor, as well as other methods known in the art. If desired, the sample can be concentrated or purified before use. For example, proteins or nucleic acids can be isolated from the sample. In some examples, the sample is filtered before use, for example to remove undesired proteins (e.g., fractionating serum to remove full-length OPN while retaining OPN-5kD). Alternatively, the sample can be used directly. In particular examples, a serum sample obtained from the subject is analyzed to determine if it contains detectable levels of OPN-5kD. In particular examples, a tumor sample obtained from the subject is analyzed to determine if it contains detectable levels of OPN-c (and in some examples also OPN-a) mRNA or protein.

Detection of OPN-5kD Peptide In Vitro

In particular examples, a sample obtained from the subject is analyzed to determine if it contains detectable levels of the OPN-5kD fragment, such as a serum sample.

Methods of detecting proteins are routine. In some examples, immunoassays are used to detect the presence of the OPN-5kD protein fragment in the sample. Generally, immunoassays include the use of one or more specific binding agents (such as antibodies) that can substantially only bind to OPN-5kD. Such binding agents can include a detectable label (such as a radiolabel, fluorophore or enzyme), that permits detection of the binding to the protein. Exemplary immunoassays that can be used include, but are not limited to: Western blotting, ELISA, fluorescence microscopy, and flow cytometry.

In one example, the specific binding agent is an antibody, such as a polyclonal or monoclonal antibody, or fragment thereof. In some examples, the antibody is a humanized antibody. In some examples, the antibody is a chimeric antibody. If desired, the antibody can include a detectable label to permit detection and in some cases quantitation of the OPN-5kD/antibody complex.

In a particular example, the antibody used is 5kd106-13D. For example, the method can include contacting the biological sample (e.g., serum) with the monoclonal 5kd106-13D antibody, a chimeric form thereof, a humanized form thereof, or a functional fragment thereof under conditions in which an immune complex will form between the 5kd106-13D antibody, chimeric form thereof, humanized form thereof, or functional fragment thereof and the OPN-5kD fragment. In some examples, the presence (or absence) of the immune complex is then detected. The presence of the immune complex indicates the presence of the OPN-5kD fragment, and thus an OPN-expressing or -overexpressing tumor such as HCC. In some embodiments a second antibody (such as an antibody that recognizes a mouse IgG) (which can be detectably labeled) that specifically binds the 5kd106-13 D antibody, a chimeric form thereof, or a humanized form thereof or a functional fragment thereof is used to detect OPN-5kD.

The presence of detectable signal above background or control levels indicates that the presence of OPN-5kD peptide in the sample. For example, the level of OPN-5kD detected can be compared to a control or reference value, such as a value that represents a level of OPN-5kD expected if a tumor that overexpresses OPN is present in the subject (such as metastatic HCC), a level of OPN-5kD expected if a tumor that overexpresses OPN is absent in the subject (such as HCC or a normal subject), a level of OPN-5kD expected if a tumor that overexpresses OPN is has metastasized in the subject (such as metastatic HCC), or combinations thereof.

In some examples, full-length OPN is also measured in the sample, and the expression levels of OPN and OPN-5kD compared, for example to ratios expected for healthy individuals, subjects with a metastatic OPN-overexpressing tumor, or subjects with an non-metastatic OPN-expressing tumor, wherein the tested ratio is compared to the control ratio, and the control ratio that is most similar to the test ratio indicates the diagnosis of the subject.

In some examples, detection of OPN-5kD at a level of at least twice (such as at least three or at least five times) that observed in a subject not having a tumor, indicates that that subject has a tumor that overexpresses OPN, has a tumor with metastatic potential, has a tumor that has metastasized, has a poor prognosis, or combinations thereof. For example, if serum levels of OPN-5kD from a subject are twice that observed for a subject not having a tumor, such as an increase of at least 100%, at least 200%, or at least 500%, this indicates that the subject has a tumor that overexpresses OPN, has a tumor with metastatic potential, has a tumor that has metastasized, has a poor prognosis, or combinations thereof.

For example, if the level of OPN-5kD detected in the subject's sample is significantly less than the level of OPN-5kD expected if a tumor that overexpresses OPN is present in the subject, is similar to or less than the level of OPN-5kD expected if a tumor that overexpresses OPN is not present in the subject, or both, this indicates that the subject does not have a tumor that overexpresses OPN. In another example, if the level of OPN-5kD detected in the subject's sample is similar or greater than the level of OPN-5kD expected if a tumor that overexpresses OPN is present in the subject, is significantly greater than the level of OPN-5kD expected if a tumor that overexpresses OPN is not present in the subject, or both, this indicates that the subject has a tumor that overexpresses OPN, such as HCC. In another example, if the level of OPN-5kD detected in the subject's sample is similar or greater than the level of OPN-5kD expected if a tumor that overexpresses OPN is present in the subject, is significantly greater than the level of OPN-5kD expected if a tumor that overexpresses OPN is not present in the subject, is similar to or greater than the level of a level of OPN-5kD expected if a tumor that overexpresses OPN is has metastasized in the subject, or combinations thereof, this indicates that the subject has a metastatic tumor that overexpresses OPN, such as metastatic HCC.

Detection of OPN-5kD In Vivo

OPN-5kD specific antibodies can also be used in vivo for diagnosis. For example, the 5kd106-13D antibody, a chimeric form thereof, or a humanized form thereof or a fragment thereof disclosed herein can also be used to detect OPN-expressing or over-expressing tumors (e.g., HCC), in vivo. The antibodies disclosed herein can also be used to detect HCC and metastatic HCC in vivo. In one embodiment, a 5kd106-13D antibody, a chimeric form thereof, or a humanized form thereof or a fragment thereof is administered to the subject for a sufficient amount of time for the antibody to localize to the tumor in the subject and to form an immune complex with the tumor. The immune complex can then be detected for example radiolocalization, radioimaging, MRI, PET scan, or fluorescence imaging, for example by using a detectibly labeled antibody, humanized form thereof or functional fragment thereof. Once detected, in an ectopic location (as in a tumor) the test results can be used to assist in or guide surgical or other excision of a tumor.

In vivo imaging methods can also be utilized with the OPN-5kD antibodies disclosed herein. These technologies include magnetic resonance imaging (for example using a biotinylated antibody and avidin-iron oxide), positron emission tomography (for example using an $^{111}$indium-labeled monoclonal antibody), and optical imaging (for example using luciferase or green fluorescent protein labeled antibodies). In one example, magnetic resonance imaging is utilized. In the setting of magnetic resonance imaging, contrast agent detection can be greatly impacted by magnetic resonance scanner field strength. Increased field strengths provide improvements by orders of magnitude in the ability to detect contrast agents (Hu et al., Annu Rev Biomed Eng. 6:157-184, 2004; Wedeking et al., Magn. Reson. Imaging. 17:569-575, 1999). For example, the limit of detection of gadolinium at 2 tesla (T) is ~30 µM. At 4 T the limit of detection is reduced to ~1 µM. With newly available 7 to 12 T scanners one would expect to detect low (10-100) nM concentrations of this contrast agent. Similar sensitivity can also be identified using contrast agents such as iron oxide.

Detection of OPN-c and OPN-a

In particular examples, a sample obtained from the subject is analyzed to determine if it contains detectable levels of OPN-c and in some examples also OPN-a, such as a tumor sample, a sample adjacent to the tumor, or both. In particular examples, OPN-a and OPN-c nucleic acid molecules (such as mRNA) are measured. However, one skilled in the art will appreciate that OPN-c protein could also be measured, for example using routine immunoassays known in the art (such as those described above).

Methods of detecting nucleic acid molecules are routine. In particular examples, a tumor sample and a sample adjacent to the tumor obtained from the subject are analyzed to determine if each contains detectable levels of OPN-c nucleic acid molecules, such as cDNA or mRNA. For example, assays that permit detection of nucleic acids can be used. Exemplary assays that can be used include, but are not limited to: Northern blotting, Southern blotting, PCR (such as RT-PCR), and DNA arrays. For example, OPN-c can be amplified from a sample using PCR, and the amplicons detected and in some examples quantitated, wherein the presence of detectable amplicons above background or control levels indicates that the tumor (or adjacent tissue) expresses OPN-c nucleic acid molecules. In one example, a nucleic acid probe that hybridizes to an OPN-c nucleic acid is contacted with the sample. For example, the probe can be incubated with the sample under high stringency conditions (such as when the hybridization is performed at about 42° C. in a hybridization solution containing 25 mM KPO$_4$ (pH 7.4), 5×SSC, 5× Denhart's solution, 50 µg/mL denatured, sonicated salmon sperm DNA, 50% formamide, 10% Dextran sulfate, and 1-15 ng/mL probe (about 5×10$^7$ cpm/µg), while the washes are performed at about 65° C. with a wash solution containing 0.2×SSC and 0.1% sodium dodecyl sulfate), wherein the presence of detectable signal from the probe above background or control levels indicates that the tumor (or adjacent tissue) expresses OPN-c nucleic acid molecules.

The presence of detectable signal above background or control levels indicates that the presence of OPN-c nucleic acid molecules in the sample. For example, the level of OPN-c detected can be compared to a control or reference value, such as a value that represents a level of OPN-c expected if a tumor is or is not metastatic (such as metastatic HCC). In one example, the level of OPN-c detected in a tumor sample is compared to the level of OPN-c detected in an adjacent non-tumor sample.

In some examples, detection of at least twice (such as at least 3-times or at least 5-times) the relative amount of OPN-c mRNA observed in a tumor sample, as compared to the relative amount of OPN-c mRNA in an adjacent non-tumor sample from the same subject, indicates that that subject has a tumor with metastatic potential, has a tumor that has metastasized, has a poor prognosis, or combinations thereof. For example, if tumor levels of OPN-c mRNA are twice that observed for an adjacent non-tumor sample, such as an increase of at least 100%, at least 200%, or at least 500%, this indicates that the subject has a tumor with metastatic potential, has a tumor that has metastasized, has a poor prognosis, or combinations thereof.

In some examples, detection of statistically similar relative amounts of OPN-c mRNA observed in a tumor sample, as compared to the relative amount of OPN-c mRNA in an adjacent non-tumor sample from the same subject, indicates that that subject does not have a tumor with metastatic potential, does not have a tumor that has metastasized, has a good prognosis, or combinations thereof.

In some examples, the ratio of OPN-a to OPN-c in tumor cells is determined. It is shown herein that the ratio for OPN-a versus OPN-c in metastatic tumors is slightly lower than for non-metastatic tumors, indicating higher levels of OPN-c in metastasis (for example a ratio of 2.27 versus 2.85). Thus methods are provided for measuring OPN-a and OPN-c expression in a tumor sample. OPN-a can be detected using methods similar to that described above for OPN-c. Expression levels of OPN-c expression and OPN-a expression in the tumor sample are compared, wherein a statistically significant increase in OPN-c expression (such as an increase of at least 20%, at least 50%, or at least 80%) in the tumor sample compared to the amount of OPN-a expression in the tumor sample indicates that the subject has an OPN-expressing tumor.

Monitoring Response to Therapy

The disclosed OPN-5kD antibodies and fragments thereof can be used to monitor response to therapy. The number and or mass of OPN-expressing tumor cells (e.g., HCC cells), such as the cells present in a subject, can be determined using the methods disclosed herein. In one embodiment, an increase in the number or mass of OPN-expressing tumor cells (e.g., HCC cells), as compared to a control, such as the number or mass of OPN-expressing tumor cells (e.g., HCC cells) at an earlier time point, indicates that the tumor is progressing and that the therapy as not effective in reducing tumor burden. Conversely, a decrease in the number or mass of OPN-expressing tumor cells (e.g., HCC cells), as compared to a control, such as the number or mass of OPN-expressing tumor cells (e.g., HCC cells) at an earlier time point, indicates that the tumor is regressing and that the therapy is effective. A control can be a standard value, or the number or mass of OPN-expressing tumor cells (e.g., HCC cells) in a sample from a subject not afflicted with a tumor or the number or mass of OPN-expressing tumor cells (e.g., HCC cells) in a sample from the subject at an earlier time point, for example prior to therapy.

Kits

Provided by this disclosure are kits that can be used to diagnose, prognose, or treat a tumor that overexpresses OPN (or combinations thereof). The disclosed kits can include instructional materials disclosing means of use of the compositions in the kit. The instructional materials can be written, in an electronic form (such as a computer diskette or compact disk) or can be visual (such as video files).

Kits are provided that can be used in the therapies and diagnostic assays disclosed herein. For example, kits can include one or more of the disclosed therapeutic compositions (such as a composition including one or more peptide fragments of OPN-5kD or OPN-5kD specific antibodies), one or more of the disclosed diagnostic compositions (such as an antibody that specifically binds OPN-5kD), or combinations thereof. Such agents can be present in separate vials.

One skilled in the art will appreciate that the kits can include other agents to facilitate the particular application for which the kit is designed. Thus, for example, the kit may additionally contain means of detecting a label (such as enzyme substrates for enzymatic labels, filter sets to detect fluorescent labels, appropriate secondary labels such as a secondary antibody, or the like). The kits may additionally include buffers and other reagents routinely used for the practice of a particular method. Such kits and appropriate contents are well known to those of skill in the art.

In one example, a kit is provided that includes reagents for detecting OPN-5kD in a biological sample, such as serum. Kits for detecting OPN-5kD can include one or more antibodies that specifically bind OPN-5kD, such as any of the antibodies disclosed herein. For example, an OPN-5kD-specific antibody disclosed herein (e.g., 5kd106-13D), a chimeric form thereof, a humanized form thereof, or a fragment thereof can be part of the disclosed kits. In some embodiments, an OPN-5kD antibody fragment, such as an Fv fragment is included in the kit. In one example, such as for in vivo uses, the antibody can be a scFv fragment. In a further embodiment, the antibody is labeled (for example, with a fluorescent, radioactive, or an enzymatic label). Such a diagnostic kit can additionally contain means of detecting a label (such as enzyme substrates for enzymatic labels, filter sets to detect fluorescent labels, appropriate secondary labels such as a secondary antibody, or the like), as well as buffers and other reagents routinely used for the practice of a particular diagnostic method.

In one example, the diagnostic kit comprises an immunoassay. Although the details of the immunoassays may vary with the particular format employed, the method of detecting the OPN-5kD fragment in a biological sample generally includes the steps of contacting the sample with an antibody which specifically reacts with OPN-5kD (e.g., 5kd106-13D) under immunologically reactive conditions. The antibody is allowed to specifically bind under immunologically reactive conditions to form an immune complex, and the presence of the immune complex (bound antibody) is detected directly or indirectly.

In one example, a kit is provided for treating a tumor that overexpresses OPN, such as HCC. For example, such kits can include one or more of the disclosed therapeutic compositions (such as a composition including an OPN-5kD specific antibody or including one or more peptide fragments of OPN-5kD). Such a diagnostic kit can additionally contain other therapeutic molecules, such as therapeutic doses of IL-2, anti-CTLA-4, an adjuvant, or combinations thereof.

OPN-5kD Antibodies

The present disclosure provides antibodies that specifically bind OPN-5kD, such as bind to the epitope EELNGAY (amino acids 30-36 of SEQ ID NO: 4). One exemplary anti-OPN-5kD monoclonal antibody is 5kD 106-13D. The disclosed OPN-5kd antibodies are useful for both therapeutic and diagnostic purposes. In some examples OPN-5kD specific antibodies have an equilibrium constant ($K_d$) of 1 nM or less. For example, antibodies are provided that bind human OPN-5kD with a binding affinity of $0.1 \times 10^{-8}$ M, at least about $0.3 \times 10^{-8}$ M, at least about $0.5 \times 10^{-8}$ M, at least about $0.75 \times 10^{-8}$ M, at least about $1.0 \times 10^{-8}$ M, at least about $1.3 \times 10^{-8}$ M at least about $1.5 \times 10^{-8}$ M, or at least about $2.0 \times 10^{-8}$ M. In additional examples, the antibody (such as a human monoclonal) binds an epitope of OPN-5kD with an equilibrium disassociation constant ($K_d$) of 1 nM or less. In particular examples, the antibody can be used to diagnose a tumor, or be used to predict the metastatic potential of the tumor. In other examples, the antibodies can be used in therapeutic compositions to treat a subject. The disclosed antibodies can be part of a kit, such as a kit used to diagnose a tumor, such as HCC (such as metastatic HCC).

In one example, the antibody is a monoclonal antibody. The monoclonal antibody can be of any isotype, such as an IgM or an IgG antibody, for example $IgG_1$ or an $IgG_2$. The class of an antibody that specifically binds OPN-5kD can be switched with another. In one aspect, a nucleic acid molecule encoding $V_L$ or $V_H$ is isolated using methods well-known in the art, such that it does not include any nucleic acid sequences encoding the constant region of the light or heavy chain, respectively. The nucleic acid molecule encoding $V_L$ or $V_H$ is then operatively linked to a nucleic acid sequence encoding a $C_L$ or $C_H$ from a different class of immunoglobulin molecule. This can be achieved using a vector or nucleic acid molecule that includes a $C_L$ or $C_H$ chain, as known in the art. For example, an antibody that specifically binds OPN-5kD that was originally IgM can be class switched to an IgG. Class switching can be used to convert one IgG subclass to another, such as from $IgG_1$ to $IgG_2$.

Isolated monoclonal antibodies specific for the OPN-5kD fragment are provided that are produced by the hybridoma 5kd106-13D, as are humanized forms of the 5kd106-13D antibody, chimeras of the 5kd106-13D antibody, and functional fragments of 5kd106-13D. The 5kd106-13D antibody specifically binds the OPN-5kD fragment produced by HCC cells. Generally, the monoclonal antibodies produced by the 5kd106-13D hybridoma include a variable heavy ($V_H$) and a variable light ($V_L$) chain and specifically bind the OPN-5kD fragment. For example, the 5kd106-13D antibody can specifically bind the OPN-5kD fragment, such as an epitope thereof (e.g., amino acids 30-36 of SEQ ID NO: 4) with an affinity constant of at least $10^6$ $M^{-1}$, such as at least $10^7$ $M^{-1}$, at least $10^8$ $M^{-1}$, at least $5 \times 10^8$ $M^{-1}$, or at least $10^9$ $M^{-1}$. Hybridoma cells and their progeny that secrete the monoclonal antibody 5kd106-13D are also encompassed by this disclosure.

Antibody fragments are encompassed by the present disclosure, such as Fab, F(ab')$_2$, and Fv which include a heavy chain and light chain variable region and are capable of binding the epitopic determinant on OPN-5kD (e.g., EELNGAY, amino acids 30-36 of SEQ ID NO: 4). These antibody fragments retain the ability to selectively bind with the antigen. Methods of making these fragments are known in the art (see for example, Harlow and Lane, *Antibodies: A Laboratory Manual*, Cold Spring Harbor Laboratory, New York, 1988). In a specific example, the antibody is an Fv antibody. In other specific examples, the functional fragment of the monoclonal antibody (e.g., 5kd106-13D) is a scFV fragment, an scFV$_2$ fragment, an Fv fragment, an Fab fragment, or an F(ab')$_2$ fragment.

The production of chimeric antibodies, which include a framework region from one antibody and the CDRs or SDRs from a different antibody, is well known in the art. Thus chimeric and humanized forms of anti-OPN-5kD antibodies (e.g., the 5kd106-13D antibody) are provided herein. These antibodies include the CDRs (or SDRs) of an antibody specific for an epitope of the OPN-5kD fragment (e.g., the 5kd106-13D antibody) and framework regions from a different antibody. In one example, the framework regions are human. In some embodiments, a humanized antibody that specifically binds the OPN-5kD fragment is a humanized form of the 5kd106-13D monoclonal antibody (or other antibody specific for an epitope of the OPN-5kD fragment) or a functional fragment thereof. In one example the sequence of the specificity determining regions (SDRs) of each CDR from the 5kd106-13D monoclonal antibody (or other antibody specific for an epitope of the OPN-5kD fragment) is determined. Residues outside the SDRs (non-ligand contacting sites) can be substituted and the monoclonal antibody retains its ability to bind the OPN-5kD fragment. The antibody or antibody fragment can be a humanized immunoglobulin having complementarity determining regions (CDRs) from the 5kd106-13D monoclonal antibody (or other antibody specific for an epitope of the OPN-5kD fragment) produced by the above-described hybridoma and immunoglobulin and heavy and light chain variable region frameworks from human acceptor immunoglobulin heavy and light chain frameworks. Generally, the humanized immunoglobulin specifically binds to the OPN-5kD fragment or an epitope thereof (such as EELNGAY, amino acids 30-36 of SEQ ID NO: 4) with an affinity constant of at least $10^7$ $M^{-1}$, such as at least $10^8$ $M^{-1}$ at least $5 \times 10^8$ $M^{-1}$ or at least $10^9$ $M^{-1}$.

Humanized monoclonal antibodies can be produced by transferring donor CDRs from heavy and light variable chains of the donor mouse immunoglobulin (such as the 5kd106-13D monoclonal antibody) into a human variable domain, and then substituting human residues in the framework regions when required to retain affinity. The use of antibody components derived from humanized monoclonal antibodies obviates potential problems associated with the immunogenicity of the constant regions of the donor antibody. Techniques for producing humanized monoclonal antibodies are described, for example, by Jones et al., *Nature* 321:522, 1986; Riechmann et al., *Nature* 332:323, 1988; Verhoeyen et al., *Science* 239:1534, 1988; Carter et al., *Proc. Nat'l Acad. Sci. U.S.A.* 89:4285, 1992; Sandhu, *Crit. Rev. Biotech.* 12:437, 1992; and Singer et al., *J. Immunol.* 150:2844, 1993. The antibody may be of any isotype, but in several embodiments the antibody is an IgG, including but not limited to, $IgG_1$, $IgG_2$, $IgG_3$ and $IgG_4$.

In one embodiment, the sequence of the humanized immunoglobulin heavy chain variable region framework can be at least about 65% identical to the sequence of the donor immunoglobulin heavy chain variable region framework. Thus, the sequence of the humanized immunoglobulin heavy chain variable region framework can be at least about 75%, at least about 85%, at least about 95%, or at least about 99% identical to the sequence of the donor immunoglobulin heavy chain variable region framework. The sequences of the heavy and light chain frameworks are known in the art. Human framework regions, and mutations that can be made in a humanized antibody framework regions, are known in the art (see, for example, in U.S. Pat. No. 5,585,089).

Exemplary human antibodies LEN and 21/28 CL are of use in providing framework regions. Exemplary light chain frameworks of human MAb LEN have the following sequences:

```
FR1:
DIVMTQS PDSLAVSLGERATINC          (SEQ ID NO: 12)

FR2:
WYQQKPGQPPLLIY                    (SEQ ID NO: 13)

FR3:
GVPDRPFGSGSGTDFTLTISSLQAEDVAVYYC  (SEQ ID NO: 14)

FR4:
FGQGQTKLEIK                       (SEQ ID NO: 15)
```

Exemplary heavy chain frameworks of human MAb 21/28' CL have the following sequences:

```
FR1:
QVQLVQSGAEVKKPQASVKVSCKASQYTFT    (SEQ ID NO: 16)

FR2:
WVRQAPGQRLEWMG                    (SEQ ID NO: 17)

FR3:
RVTITRDTSASTAYMELSSLRSEDTAVYYCAR  (SEQ ID NO: 18)

FR4:
WGQGTLVTVSS.                      (SEQ ID NO: 19)
```

These framework sequences are provided for example only; a humanized antibody can include the human framework region from any human monoclonal antibody of interest.

Fragments of the 5kd106-13D antibody (or other antibody specific for an epitope of the OPN-5kD fragment), a chimeric form thereof, or a humanized form thereof are also encompassed by the present disclosure. Antibodies, such as murine monoclonal antibodies, chimeric antibodies, and humanized antibodies, include full length molecules as well as fragments thereof, such as Fab, F(ab')$_2$, and Fv which include a heavy chain and light chain variable region and are capable of binding the epitope determinant (e.g., amino acids 30-36 of SEQ ID NO:4). In some embodiments, the antibodies fragments have the sequences for $V_L$ and $V_H$ regions for the 5kd106-13D antibody. Fv antibodies are typically about 25 kDa and contain a complete antigen-binding site with three CDRs per each heavy chain and each light chain. To produce these antibodies, the $V_H$ and the $V_L$ can be expressed from two individual nucleic acid constructs in a host cell. If the $V_H$ and the $V_L$ are expressed non-contiguously, the chains of the Fv antibody are typically held together by noncovalent interactions. However, these chains tend to dissociate upon dilution, so methods have been developed to crosslink the chains through glutaraldehyde, intermolecular disulfides, or a peptide linker. Thus, in one example, the Fv can be a disulfide stabilized Fv (dsFv), wherein the heavy chain variable region and the light chain variable region are chemically linked by disulfide bonds.

In an additional example, the Fv fragments include $V_H$ and $V_L$ chains connected by a peptide linker. These single-chain antigen binding proteins (sFv) are prepared by constructing a structural gene comprising DNA sequences encoding the $V_H$ and $V_L$ domains connected by an oligonucleotide. The structural gene is inserted into an expression vector, which can be subsequently introduced into a host cell such as *E. coli* to recombinantly express the antibody fragment. The recombinant host cells synthesize a single polypeptide chain with a linker peptide bridging the two V domains. Methods for producing sFvs are known in the art (see Whitlow et al., *Methods: a Companion to Methods in Enzymology*, Vol. 2, page 97, 1991; Bird et al., *Science* 242:423, 1988; U.S. Pat. No. 4,946, 778; and Pack et al., *Bio/Technology* 11:1271, 1993).

Antibody fragments can be prepared by proteolytic hydrolysis of the antibody or by expression in *E. coli* of DNA encoding the fragment. Antibody fragments can be obtained by pepsin or papain digestion of whole antibodies by conventional methods. For example, antibody fragments can be produced by enzymatic cleavage of antibodies with pepsin to provide a 5S fragment denoted F(ab')$_2$. This fragment can be further cleaved using a thiol reducing agent, and optionally a blocking group for the sulfhydryl groups resulting from cleavage of disulfide linkages, to produce 3.5S Fab' monovalent fragments. Alternatively, an enzymatic cleavage using pepsin produces two monovalent Fab' fragments and an Fc fragment directly (see U.S. Pat. No. 4,036,945 and U.S. Pat. No. 4,331,647, and references contained therein; Nisonhoff et al., *Arch. Biochem. Biophys.* 89:230, 1960; Porter, *Biochem. J.* 73:119, 1959; Edelman et al., *Methods in Enzymology*, Vol. 1, page 422, Academic Press, 1967; and Coligan et al. at sections 2.8.1-2.8.10 and 2.10.1-2.10.4). Other methods of cleaving antibodies, such as separation of heavy chains to form monovalent light-heavy chain fragments, further cleavage of fragments, or other enzymatic, chemical, or genetic techniques may also be used, so long as the fragments bind to the antigen that is recognized by the intact antibody.

One of skill will realize that conservative variants of the antibodies can be produced. Such conservative variants employed in antibody fragments, such as dsFv fragments or in scFv fragments, will retain critical amino acid residues necessary for correct folding and stabilizing between the $V_H$ and the $V_L$ regions, and will retain the charge characteristics of the residues in order to preserve the low pI and low toxicity of the molecules. Amino acid substitutions (such as at most one, at most two, at most three, at most four, or at most five amino acid substitutions) can be made in the $V_H$ and the $V_L$ regions to increase yield. Conservative amino acid substitution tables providing functionally similar amino acids are well known to one of ordinary skill in the art. The following six groups are examples of amino acids that are considered to be conservative substitutions for one another:

1) Alanine (A), Serine (S), Threonine (T);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V); and
6) Phenylalanine (F), Tyrosine (Y), Tryptophan (W).

Thus, one of skill in the art can readily review the sequences of an anti-OPN-5kD monoclonal antibody (such as 5kd106-13D), locate one or more of the amino acids listed above, identify a conservative substitution, and produce the conservative variant using well-known molecular biology techniques. Generally, conservative variants will bind the target antigen with an equal to or greater efficiency than the parent monoclonal antibody.

Effector molecules, such as therapeutic, diagnostic, or detection moieties can be linked to an antibody of interest, such as an antibody that specifically binds OPN-5kD (e.g., 5kd106-13D) using any number of means known to those of skill in the art. In view of the large number of methods that have been reported for attaching a variety of radiodiagnostic compounds, radiotherapeutic compounds, labels (such as enzymes or fluorescent molecules), drugs, toxins, and other agents to antibodies, one skilled in the art will be able to determine a suitable method for attaching a given agent to an antibody or fragment thereof. For example, covalent and non-covalent attachment means can be used. The procedure for attaching an effector molecule to an antibody varies according to the chemical structure of the effector. Polypeptides typically contain a variety of functional groups; such as carboxylic acid (COOH), free amine (—NH$_2$) or sulfhydryl (—SH) groups, which are available for reaction with a suitable functional group on an antibody to result in the binding of the effector molecule. Alternatively, the antibody is derivatized to expose or attach additional reactive functional groups. The derivatization can involve attachment of any of a number of linker molecules such as those available from Pierce Chemical Company, Rockford, Ill. The linker can be any molecule used to join the antibody to the effector molecule. The linker is capable of forming covalent bonds to both the antibody and to the effector molecule. Suitable linkers are well known to those of skill in the art and include, but are not limited to, straight or branched-chain carbon linkers, heterocyclic carbon linkers, or peptide linkers. Where the antibody and the effector molecule are polypeptides, the linkers may be joined to the constituent amino acids through their side groups (such as through a disulfide linkage to cysteine) or to the alpha carbon amino and carboxyl groups of the terminal amino acids.

In some circumstances, it is desirable to free the effector molecule from the antibody when the immunoconjugate has reached its target site. Therefore, in these circumstances, immunoconjugates will include linkages that are cleavable in the vicinity of the target site. Cleavage of the linker to release the effector molecule from the antibody may be prompted by enzymatic activity or conditions to which the immunoconjugate is subjected either inside the target cell or in the vicinity of the target site. When the target site is a tumor, a linker which is cleavable under conditions present at the tumor site (for example when exposed to tumor-associated enzymes or acidic pH) may be used.

An antibody that specifically binds to the OPN-5kD fragment (e.g., 5kd106-13 D or a humanized or chimeric form thereof or a fragment thereof) can be labeled with one or more detectable agents or labels. In some embodiments, labels are attached by spacer arms of various lengths to reduce steric hindrance. Useful detectable agents include electron-dense compounds, enzymes, fluorochromes, haptens, and radioisotopes. Anti-OPN-5kD antibodies (e.g., 5kd106-13D) can also be detected using secondary reagents with specificity for mouse IgG. Useful detection agents include fluorescent compounds, including fluorescein, fluorescein isothiocyanate, rhodamine, 5-dimethylamine-1-napthalenesulfonyl chloride, phycoerythrin, lanthanide phosphors, and the cyanine family of dyes (such as Cy-3 or Cy-5) and the like. Bioluminescent markers are also of use, such as luciferase, Green fluorescent protein (GFP), Yellow fluorescent protein (YFP). An OPN-5KD antibody can also be labeled with enzymes that are useful for detection, such as horseradish peroxidase, β-galactosidase, luciferase, alkaline phosphatase, glucose oxidase and the like. When an antibody is labeled with a detectable enzyme, it can be detected by adding additional reagents that the enzyme uses to produce a reaction product that can be discerned. For example, when the agent horseradish peroxidase is present the addition of hydrogen peroxide and diaminobenzidine leads to a colored reaction product, which is visually detectable. An antibody may also be labeled with biotin, and detected through indirect measurement of avidin or streptavidin binding. The avidin itself can also be labeled with an enzyme or a fluorescent label. In one example, an OPN-5kD-specific antibody is labeled with electrodense particles, such as a nanoparticle (for example a gold particle or a semiconductor nanocrystal, such as a quantum dot (QDOT®)).

An antibody that specifically binds to the OPN-5kD fragment (e.g., 5kd106-13 D or a humanized or chimeric form thereof or a fragment thereof) can be labeled with a paramagnetic agent, such as gadolinium. Antibodies can also be labeled with lanthanides (such as europium and dysprosium), and manganese. Paramagnetic particles such as superparamagnetic iron oxide are also of use as labels. An antibody may also be labeled with a predetermined polypeptide epitopes recognized by a secondary reporter (such as leucine zipper pair sequences, binding sites for secondary antibodies, metal binding domains, epitope tags).

Antibodies can also be labeled with a radiolabeled amino acid, such as $^3$H, $^{14}$C, $^{15}$N, $^{35}$S, $^{90}$Y, $^{99}$Tc, $^{111}$In, $^{125}$I, or $^{131}$I. The radiolabel may be used for diagnostic and/or therapeutic purposes. For instance, the radiolabel may be used to detect OPN-5kD expressing cells (such as HCC cells) for example by x-ray or other diagnostic techniques, such as positron emission tomography (PET) or magnetic resonance imaging (MRI). Further, the radiolabel may be used therapeutically as a toxin for tumors that express OPN (such as HCC).

In some examples a therapeutic agent is linked to an antibody that specifically binds to the OPN-5kD fragment (e.g., 5kd106-13D or a humanized or chimeric form thereof or a fragment thereof). Therapeutic agents include various drugs such as vinblastine, daunomycin and the like, and effector molecules such as cytotoxins for example native or modified *Pseudomonas* exotoxin (e.g., see U.S. Pat. Nos. 4,892,827, 5,602,095, 5,608,039 and 5,512,658), ricin, abrin (e.g., see Funatsu et al., *Agr. Biol. Chem.* 52:1095, 1988; and Olsnes, *Methods Enzymol.* 50:330-335, 1978), botulinum toxins A through F, or Diphtheria toxin (e.g., see U.S. Pat. No. 5,792,458 and U.S. Pat. No. 5,208,021), ribonucleases (e.g., see Suzuki et al., *Nat. Biotech.* 17:265-70, 1999), encapsulating agents, (such as, liposomes) which themselves contain pharmacological compositions, target moieties and ligands. Exemplary toxins are well known in the art and many are readily available from commercial sources (for example, Sigma Chemical Company, St. Louis, Mo.). The choice of a particular therapeutic agent depends on the particular target molecule or cell and the biological effect desired to be evoked. Thus, for example, the therapeutic agent may be an effector molecule that is cytotoxic which is used to bring about the death of a particular target cell. Conversely, where it is merely desired to invoke a non-lethal biological response, a therapeutic agent can be conjugated to a non-lethal pharmacological agent or a liposome containing a non-lethal pharmacological agent.

The OPN-5kD antibodies or antibody fragments disclosed herein (e.g., 5kd106-13D) can be derivatized or linked to another molecule (such as another peptide or protein). In general, the antibodies or portion thereof is derivatized such that the binding to the OPN-5kD fragment is not affected adversely by the derivatization or labeling. For example, the antibody can be functionally linked (by chemical coupling, genetic fusion, noncovalent association or otherwise) to one or more other molecular entities, such as another antibody (for example, a bispecific antibody), a detection agent, a pharmaceutical agent, a chemical group (such as polyethylene glycol (PEG), a methyl or ethyl group, or a carbohydrate group for example to increase serum half-life or to increase tissue binding of the antibody) and/or a protein or peptide that can mediate association of the antibody or antibody portion with another molecule (such as a streptavidin core region or a polyhistidine tag).

One type of derivatized antibody is produced by crosslinking two or more antibodies (of the same type or of different types, such as to create bispecific antibodies). Suitable crosslinkers include those that are heterobifunctional, having two distinctly reactive groups separated by an appropriate spacer (such as m-maleimidobenzoyl-N-hydroxysuccinimide ester) or homobifunctional (such as disuccinimidyl suberate). Such linkers are available from Pierce Chemical Company, Rockford, Ill.

Nucleic Acid Molecules Encoding Antibodies

Nucleic acid molecules encoding the disclosed OPN-5kD antibodies (e.g., 5kd106-13D) or a chimeric or humanized form of any of these antibodies or a fragment thereof can readily be produced by one of skill in the art. Upon generation of a monoclonal antibody, such as 5kd106-13D (see Example 9), the amino acid sequence can be determined and a nucleic acid sequence encoding the amino acid sequence can be engineered. In addition, one of skill can readily construct a variety of clones containing functionally equivalent nucleic acid molecules, such as nucleic acid molecules which differ in sequence but which encode the same effect or molecule ("EM") or antibody sequence. Thus, nucleic acids encoding OPN-5kD-specific antibodies (such as those specific for the epitope EELNGAY, amino acids 30 to 36 of SEQ ID NO: 4), conjugates and fusion proteins are provided herein.

Nucleic acid molecules encoding OPN-5kD-specific antibodies can readily be produced by one of skill in the art, using the amino acid sequences provided herein, and the genetic code. In addition, one of skill can readily construct a variety of clones containing functionally equivalent nucleic acids, such as nucleic acids which differ in sequence but which encode the same effector molecule or antibody sequence.

Thus, nucleic acids encoding OPN-5kD-specific antibodies, conjugates and fusion proteins are provided herein.

Nucleic acid sequences encoding the antibodies that specifically bind OPN-5kD (for example that are specific for the EELNGAY epitope, amino acids 30 to 36 of SEQ ID NO: 4) can be prepared by any suitable method including, for example, cloning of appropriate sequences or by direct chemical synthesis by methods such as the phosphotriester method of Narang et al., *Meth. Enzymol.* 68:90-99, 1979; the phosphodiester method of Brown et al., *Meth. Enzymol.* 68: 109-151, 1979; the diethylphosphoramidite method of Beaucage et al., *Tetra. Lett.* 22:1859-1862, 1981; the solid phase phosphoramidite triester method described by Beaucage & Caruthers, *Tetra. Letts.* 22(20):1859-1862, 1981, for example, using an automated synthesizer as described in, for example, Needham-VanDevanter et al., *Nucl. Acids Res.* 12:6159-6168, 1984; and, the solid support method of U.S. Pat. No. 4,458,066. Chemical synthesis produces a single stranded oligonucleotide. This can be converted into double stranded DNA by hybridization with a complementary sequence, or by polymerization with a DNA polymerase using the single strand as a template. One of skill would recognize that while chemical synthesis of DNA is generally limited to sequences of about 100 bases, longer sequences may be obtained by the ligation of shorter sequences.

Exemplary nucleic acid molecules encoding sequences encoding an antibody that specifically binds OPN-5kD (e.g., 5kd106-13D) can be prepared by cloning techniques. Examples of appropriate cloning and sequencing techniques, and instructions sufficient to direct persons of skill through many cloning exercises are found in Sambrook et al., supra, Berger and Kimmel (eds.), supra, and Ausubel, supra. Product information from manufacturers of biological reagents and experimental equipment also provide useful information. Such manufacturers include the SIGMA Chemical Company (Saint Louis, Mo.), R&D Systems (Minneapolis, Minn.), Pharmacia Amersham (Piscataway, N.J.), CLONTECH Laboratories, Inc. (Palo Alto, Calif.), Chem Genes Corp., Aldrich Chemical Company (Milwaukee, Wis.), Glen Research, Inc., GIBCO BRL Life Technologies, Inc. (Gaithersburg, Md.), Fluka Chemica-Biochemika Analytika (Fluka Chemie AG, Buchs, Switzerland), Invitrogen (San Diego, Calif.), and Applied Biosystems (Foster City, Calif.), as well as many other commercial sources known to one of skill in the art.

Nucleic acid molecules can also be prepared by amplification methods. Amplification methods include polymerase chain reaction (PCR), the ligase chain reaction (LCR), the transcription-based amplification system (TAS), the self-sustained sequence replication system (3SR). A wide variety of cloning methods, host cells, and in vitro amplification methodologies are well-known to persons skilled in the art.

In one example, an antibody that specifically binds OPN-5kD (e.g., 5kd106-13 D) is prepared by inserting the cDNA which encodes a variable region from an antibody into a vector which includes the cDNA encoding an EM, such as an enzyme or label. The insertion is made so that the variable region and the EM are read in frame so that one continuous polypeptide is produced. Thus, the encoded polypeptide contains a functional Fv region and a functional EM region. In one example, cDNA encoding an enzyme is ligated to a scFv so that the enzyme is located at the carboxyl terminus of the scFv. For example, a cDNA encoding horseradish peroxidase or alkaline phosphatase, or a polypeptide marker of interest can be ligated to a scFv so that the enzyme (or polypeptide marker) is located at the amino terminus of the scFv. In another example, the label is located at the amino terminus of the scFv. In a further example, cDNA encoding the protein or polypeptide marker is ligated to a heavy chain variable region of an antibody, so that the enzyme or polypeptide marker is located at the carboxyl terminus of the heavy chain variable region. The heavy chain-variable region can subsequently be ligated to a light chain variable region of the antibody using disulfide bonds. In a yet another example, cDNA encoding an enzyme or a polypeptide marker is ligated to a light chain variable region of an antibody, so that the enzyme or polypeptide marker is located at the carboxyl terminus of the light chain variable region. The light chain-variable region can subsequently be ligated to a heavy chain variable region of the antibody using disulfide bonds.

Once the nucleic acids encoding the anti-OPN-5kD antibody (e.g., 5kd106-13 D), labeled antibody, or fragment thereof are isolated and cloned, the protein can be expressed in a recombinantly engineered cell such as bacteria, plant, yeast, insect and mammalian cells using a suitable expression vector. One or more DNA sequences encoding the antibody or fragment thereof can be expressed in vitro by DNA transfer into a suitable host cell. The cell may be prokaryotic or eukaryotic. The term also includes any progeny of the subject host cell. It is understood that all progeny may not be identical to the parental cell since there may be mutations that occur during replication. Methods of stable transfer, meaning that the foreign DNA is continuously maintained in the host, are known in the art. Hybridomas expressing the antibodies of interest (e.g., a hybridoma that produces 5kd106-13D) are also encompassed by this disclosure.

Polynucleotide sequences encoding the anti-OPN-5kD antibody (e.g., 5kd106-13D), labeled antibody, or functional fragment thereof, can be operatively linked to expression control sequences. An expression control sequence operatively linked to a coding sequence is ligated such that expression of the coding sequence is achieved under conditions compatible with the expression control sequences. The expression control sequences include, but are not limited to appropriate promoters, enhancers, transcription terminators, a start codon (ATG) in front of a protein-encoding gene, splicing signal for introns, maintenance of the correct reading frame of that gene to permit proper translation of mRNA, and stop codons.

The polynucleotide sequences encoding the OPN-5kD-specific antibody (e.g., 5kd106-13D), labeled antibody, or functional fragment thereof can be inserted into an expression vector including, but not limited to a plasmid, virus or other vehicle that can be manipulated to allow insertion or incorporation of sequences and can be expressed in either prokaryotes or eukaryotes. Hosts can include microbial, yeast, insect and mammalian organisms. Methods of expressing DNA sequences having eukaryotic or viral sequences in prokaryotes are well known in the art. Biologically functional viral and plasmid DNA vectors capable of expression and replication in a host are known in the art.

Transformation of a host cell with recombinant DNA can be carried out by conventional techniques as are well known to those skilled in the art. Where the host is prokaryotic, such as *E. coli*, competent cells which are capable of DNA uptake can be prepared from cells harvested after exponential growth phase and subsequently treated by the $CaCl_2$ method using procedures well known in the art. Alternatively, $MgCl_2$ or RbCl can be used. Transformation can also be performed after forming a protoplast of the host cell if desired, or by electroporation.

When the host is a eukaryote, such methods of transfection of DNA as calcium phosphate coprecipitates, conventional mechanical procedures such as microinjection, electroporation, insertion of a plasmid encased in liposomes, or virus vectors may be used. Eukaryotic cells can also be cotransformed with polynucleotide sequences encoding the antibody, labeled antibody, or functional fragment thereof, and a second foreign DNA molecule encoding a selectable phenotype, such as the herpes simplex thymidine kinase gene. Another method is to use a eukaryotic viral vector, such as simian virus 40 (SV40) or bovine papilloma virus, to transiently infect or transform eukaryotic cells and express the protein (see for example, *Eukaryotic Viral Vectors*, Cold Spring Harbor Laboratory, Gluzman ed., 1982). One of skill in the art can readily use an expression systems such as plasmids and vectors of use in producing proteins in cells including higher eukaryotic cells such as the COS, CHO, HeLa and myeloma cell lines.

Isolation and purification of recombinantly expressed polypeptide can be carried out by conventional means including preparative chromatography and immunological separations. Once expressed, the OPN-5kD-specific antibody (e.g., 5kd106-13D), labeled antibody or functional fragment thereof can be purified according to standard procedures of the art, including ammonium sulfate precipitation, affinity columns, column chromatography, and the like (see, generally, R. Scopes, *Protein Purification*, Springer-Verlag, N.Y., 1982). Substantially pure compositions of at least about 90 to 95% homogeneity are disclosed herein, and 98 to 99% or more homogeneity can be used for pharmaceutical purposes. Once purified, partially or to homogeneity as desired, if to be used therapeutically, the polypeptides should be substantially free of endotoxin.

Methods for expression of single chain antibodies and/or refolding to an appropriate active form, including single chain antibodies, from bacteria such as *E. coli* have been described and are well-known and are applicable to the antibodies disclosed herein. See, Buchner et al., *Anal. Biochem.* 205:263-270, 1992; Pluckthun, *Biotechnology* 9:545, 1991; Huse et al., *Science* 246:1275, 1989 and Ward et al., *Nature* 341:544, 1989.

Often, functional heterologous proteins from *E. coli* or other bacteria are isolated from inclusion bodies and require solubilization using strong denaturants, and subsequent refolding. During the solubilization step, as is well known in the art, a reducing agent must be present to separate disulfide bonds. An exemplary buffer with a reducing agent is: 0.1 M Tris pH 8, 6 M guanidine, 2 mM EDTA, 0.3 M DTE (dithioerythritol). Reoxidation of the disulfide bonds can occur in the presence of low molecular weight thiol reagents in reduced and oxidized form, as described in Saxena et al., *Biochemistry* 9: 5015-5021, 1970, and especially as described by Buchner et al., supra.

Renaturation is typically accomplished by dilution (for example, 100-fold) of the denatured and reduced protein into refolding buffer. An exemplary buffer is 0.1 M Tris, pH 8.0, 0.5 M L-arginine, 8 mM oxidized glutathione (GSSG), and 2 mM EDTA.

As a modification to the two chain antibody purification protocol, the heavy and light chain regions are separately solubilized and reduced and then combined in the refolding solution. An exemplary yield is obtained when these two proteins are mixed in a molar ratio such that a 5-fold molar excess of one protein over the other is not exceeded. Excess oxidized glutathione or other oxidizing low molecular weight compounds can be added to the refolding solution after the redox-shuffling is completed.

In addition to recombinant methods, the antibodies, labeled antibodies and functional fragments thereof that are disclosed herein can also be constructed in whole or in part using standard peptide synthesis. Solid phase synthesis of the polypeptides of less than about 50 amino acids in length can be accomplished by attaching the C-terminal amino acid of the sequence to an insoluble support followed by sequential addition of the remaining amino acids in the sequence. Techniques for solid phase synthesis are described by Barany & Merrifield, *The Peptides: Analysis, Synthesis, Biology. Vol. 2: Special Methods in Peptide Synthesis, Part A.* pp. 3-284; Merrifield et al., *J. Am. Chem. Soc.* 85:2149-2156, 1963, and Stewart et al., *Solid Phase Peptide Synthesis*, 2nd ed., Pierce Chem. Co., Rockford, Ill., 1984. Proteins of greater length may be synthesized by condensation of the amino and carboxyl termini of shorter fragments. Methods of forming peptide bonds by activation of a carboxyl terminal end (such as by the use of the coupling reagent N,N'-dicylohexylcarbodimide) are well known in the art.

Use of OPN-5kD Antibodies

The disclosure provides a method for detecting the OPN-5kD fragment in a biological sample, wherein the method includes contacting a biological sample with an antibody that binds an OPN-5kD epitope under conditions conductive to the formation of an immune complex, and detecting the immune complex, to detect the OPN-5kD in the biological sample. The disclosure also provides a method for treating a subject suspected of having an OPN expressing tumor with OPN-5kD specific antibodies, wherein the method includes contacting a biological sample (in vitro or in vivo) with an antibody that binds an OPN-5kD epitope and inhibits or reduces the binding of OPN to CD44 receptors (such methods are described herein and more specifically in the section describing methods of treatment and therapeutic compositions).

In one example, the detection of the OPN-5kD fragment in the sample indicates that the subject has a malignancy. In another example, the detection of OPN-5kD in the sample indicates that a tumor in the subject is prone to metastasis.

In one example, the antibody that specifically binds OPN-5kD is directly labeled with a detectable label. In another example, the antibody that specifically binds OPN-5kD (the first antibody) is unlabeled and a second antibody or other molecule that can bind the antibody that specifically binds OPN-5kD is labeled. As is well known to one of skill in the art, a second antibody is chosen that is able to specifically bind the specific species and class of the first antibody. For example, if the first antibody is a human IgG, then the secondary antibody can be an anti-human-IgG. Other molecules that can bind to antibodies include, without limitation, Protein A and Protein G, which are available commercially.

Suitable labels for the antibody or secondary antibody are described above, and include various enzymes, prosthetic groups, fluorescent materials, luminescent materials, magnetic agents and radioactive materials. Non-limiting examples of suitable enzymes include horseradish peroxidase, alkaline phosphatase, beta-galactosidase, or acetylcholinesterase. Non-limiting examples of suitable prosthetic group complexes include streptavidin/biotin and avidin/biotin. Non-limiting examples of suitable fluorescent materials include umbelliferone, fluorescein, fluorescein isothiocyanate, rhodamine, dichlorotriazinylamine fluorescein, dansyl chloride or phycoerythrin. A non-limiting exemplary luminescent material is luminol; a non-limiting exemplary a magnetic agent is gadolinium, and non-limiting exemplary radioactive labels include $^{125}I$, $^{131}I$, $^{35}S$ or $^{3}H$.

In an alternative example, the presence of the OPN-5kD fragment can be assayed in a biological sample by a competition immunoassay utilizing OPN-5kD standards labeled with a detectable substance and an unlabeled antibody that specifically binds an OPN-5kD epitope. In this assay, the biological sample (such as serum), the labeled OPN-5kD standards and the antibody that specifically binds OPN-5kD are combined and the amount of labeled OPN-5kD standard bound to the unlabeled antibody is determined. The amount of OPN-5kD in the biological sample is inversely proportional to the amount of labeled OPN-5kD standard bound to the antibody that specifically binds OPN-5kD.

The immunoassays and methods disclosed herein can be used for a number of purposes. In one example, the antibodies that specifically bind OPN-5kD are used to detect the OPN-5kD in serum obtained from a subject known to have or suspected of having a tumor, such as HCC. Increased expression of OPN-5kD is associated with a tumor that expresses OPN, such as HCC, as well as increased likelihood of metastasis of the tumor. Thus, the level of OPN-5kD can be used to diagnose, or determine the prognosis of, HCC in a subject.

Example 1

OPN and MMP-9 are Co-Upregulated in HCC

This example describes methods used to demonstrate that OPN and MMP-9 are co-upregulated in HCC.

Figure 1B:
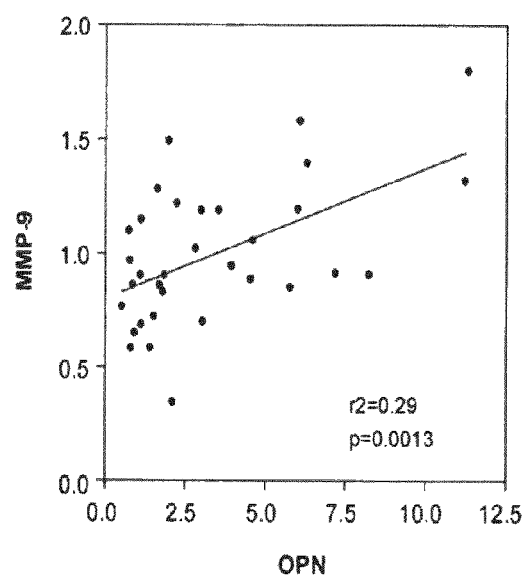
FIG. 1B is a graph showing OPN and MMP-9 expression level correlation as determined using linear regression analysis after plotting values within each patient case.

Messenger RNA (mRNA) levels of OPN and MMP-9 were quantified in normal and HCC tissue (obtained from human subjects) by microarray analysis. As shown in FIG. 1A, expression of both OPN and MMP-9 was significantly increased in primary HCC tumors and their corresponding metastatic lesions as compared to non-metastatic tumors (Ye et al., *Nat. Med.* 9:416-23, 2003). As shown in FIG. 1B, up-regulated expression was significantly correlated within each patient case (p=0.0013).

Example 2

OPN is a Substrate for MMP-9 Activity

This example describes methods used to demonstrate that MMP-9 cleaves OPN into several fragments.

OPN cleavage assays were performed as follows. Human MMP-9 (Calbiochem, CA) was incubated at 37° C. for 3 hours with recombinant human OPN (R&D systems, MN) at an optimized ratio (5:1 substrate:enzyme) in a buffered solution (200 mM NaCl, 5 mM CaCl, 50 mM Tris-Cl, pH 7.5). Digested OPN was analyzed by 16% tris-glycine SDS-PAGE followed by colloidal coomassie blue staining (SimplyBlue™, Invitrogen, CA). Separate cleavage reactions (2 μg OPN) were transferred to PDVF membranes for amino-end terminal microsequencing.

For western blot analysis, MMP-9-digested OPN samples and whole cell lysates (50 μg) were transferred to 0.22 um PVDF membranes and probed with a polyclonal antibody generated to a 14-residue peptide just downstream of the residue 169 thrombin cleavage site (KSKKFRRPDIQYPD; amino acids 169-183 of SEQ ID NO: 2) (Abcam, MA). HEK-293 cell lysates were probed with an anti-FLAG antibody (Sigma, Mo.). Immuno-reactive proteins were detected by chemilluminescence (ECL, GE Healthcare Life Sciences, NJ).

Figure 2A:
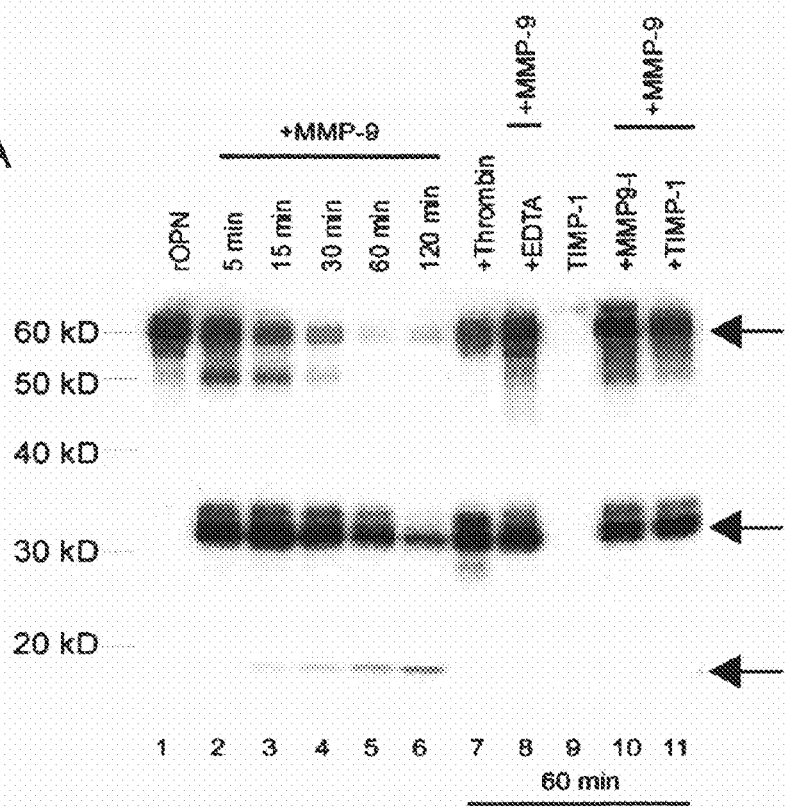
FIG. 2A is a digital image of a Western blot showing a time-dependent MMP-9-cleavage of recombinant human OPN (~65 kD) (lanes 2-6). MMP inhibitors were added to separate reactions and analyzed after a 1-hour digestion at 37° C.: EDTA (10 mM), MMP-9 inhibitor I (2 µM) and TIMP-1 (0.1 µM) (lanes 8, 10, 11 respectively). Undigested OPN (lane 1), OPN exposed to thrombin cleavage (0.05 U) (lane 7) and TIMP-1 alone lanes (9) were included as controls.
Figure 2B:
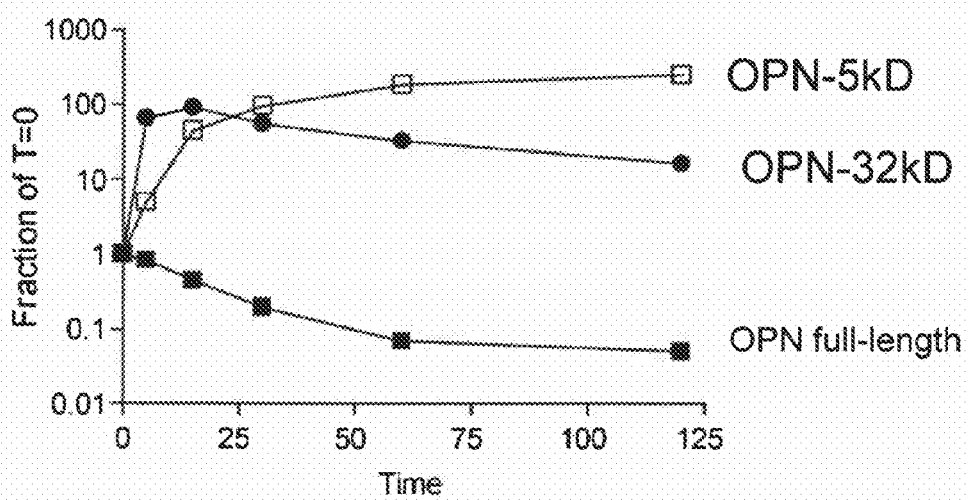
FIG. 2B is a graph showing the kinetics of the MMP-9 specific OPN cleavage quantified by densitometric analysis of the three bands marked by arrows in FIG. 2A and presented as a fraction of starting values at Time=0.

Recombinant MMP-9 cleaved OPN at two predominant sites in vitro, residues 166 and 210, resulting in 4 identified fragments: OPN-34kD (residues 1-166), OPN-32kD (residues 167-314), OPN-5kD (residues 167-210), and OPN-24kD (residues 211-314). Residue numbering is based on the sequence shown in SEQ ID NO: 2. Two of the fragments, OPN-32kD and OPN-5kD, were detected using an antibody that recognizes residues 169-183 (FIG. 2A). The OPN-5kD fragment was distinct from the products of thrombin digestion and could not be detected in cleavage reactions partially inhibited by the concomitant addition of EDTA, a naturally-occurring inhibitor of MMP-9 (tissue inhibitor of matrix metalloproteinase-1, or TIMP-1), or the hydroxamate MMP-9 inhibitor I. Cleavage was similarly inhibited by a monoclonal antibody to MMP-9. OPN-5kD formation appeared dependent on further cleavage of OPN-32kD over time (FIG. 2B).

Figure 3A:
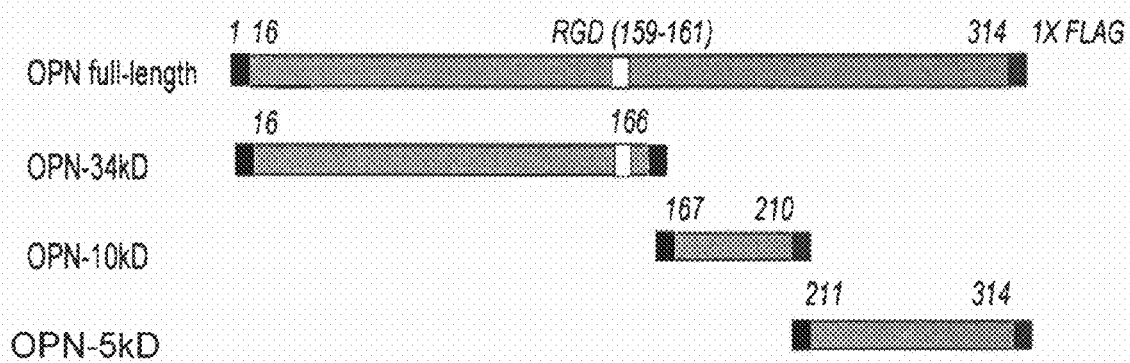
FIG. 3A is a schematic drawing showing the expression vectors generated to determine the activity level of OPN fragments.

Expression vectors were generated that included an OPN fragment with its C-termini fused to a FLAG-tag and its N-termini following the native OPN putative secretory leading 16 amino acid peptide. Complementary DNA sequences encoding the wild-type OPN protein (OPN-a) and three identified truncated protein sequences described above (OPN-34kD, OPN-5kD, and OPN-24kD) were cloned into a CMV-promoter mammalian expression vector with a C-terminal 1× FLAG tag (pDest-490) (Gateway cloning system, Invitrogen, CA). The 16-residue predicted signal peptide sequence (MRIAVICFCLLGITCA, amino acids 1-16 of SEQ ID NO: 2) was fused to the N-terminus of each construct following a Kozak translation initiation sequence to ensure similar secretion. Entry clones were verified by sequencing and gel electrophoresis. As shown in FIG. 3A, the native 16 amino acid signal sequence (indicated in black) was included at the N-terminus of each of the 4 sequences. The RGD domain was present in 2 of the 4 constructs (indicated in white).

Figure 3B:
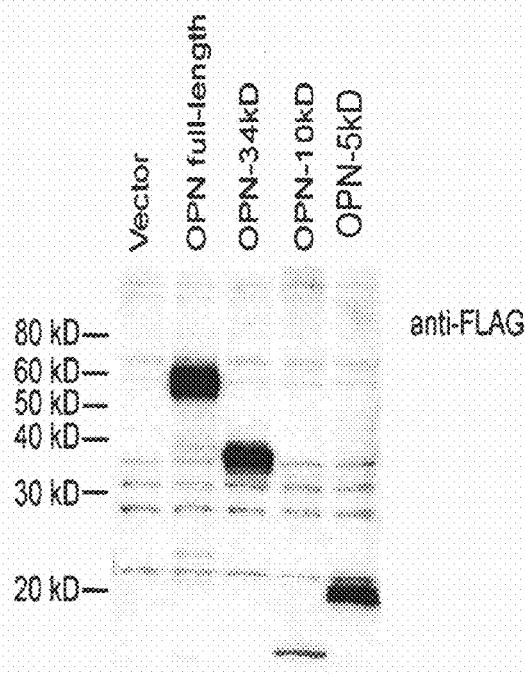
FIG. 3B is a digital image of a Western blot showing expression of the four constructs in FIG. 3A in HEK 293 cells.

Effective expression was demonstrated in HEK 293 cells by immunoblotting for the C-terminal FLAG tagged sequences as follows. Secreted levels were also detected in conditioned media samples. HEK 293 cells were transiently transfected (Lipofectamine 2000, Invitrogen, CA) with 5 μg plasmid DNA and harvested after 24 hours. Total protein cell lysates (50 μg) were run on a 4-20% SDS-PAGE gel, transferred to a nitrocellulose membrane and probed with an anti-FLAG polyclonal antibody. As shown in FIG. 3B, all of the constructs were expressed in HEK 293 cells.

Example 3

OPN-5kD and MMP-9 Expression Correlate with Metastatic Activity

This example describes methods used to demonstrate that expression of the OPN-5kD fragment (as well as full-length OPN) and expression of MMP-9 correlated with metastatic potential.

Three human HCC cell lines (Hep3B, SMMC-7721, and MHCC-97) of established inherent differences in invasiveness were comparatively screened for OPN protein expression.

Single-cell clones of the low-metastatic HCC cell line SMMC-7721 were produced by a limiting dilution cloning technique (Morley et al., *Exp. Hematol.*, 11:418-24, 1983). Briefly, early passage parental cells were plated in 96-well plates (0.5 cell/well) in supplemented media (20% conditioned media) for two weeks with bi-weekly media changes. Cells were propagated by sequential splitting to generate large cell cultures for frozen storage. The subclone most closely resembling the parental cell line by morphology, growth, and a preliminary evaluation of adhesion (see assay methods below), SMMC-7721-SC2, was used for subsequent assays at early passage numbers (<10).

Figure 4A:
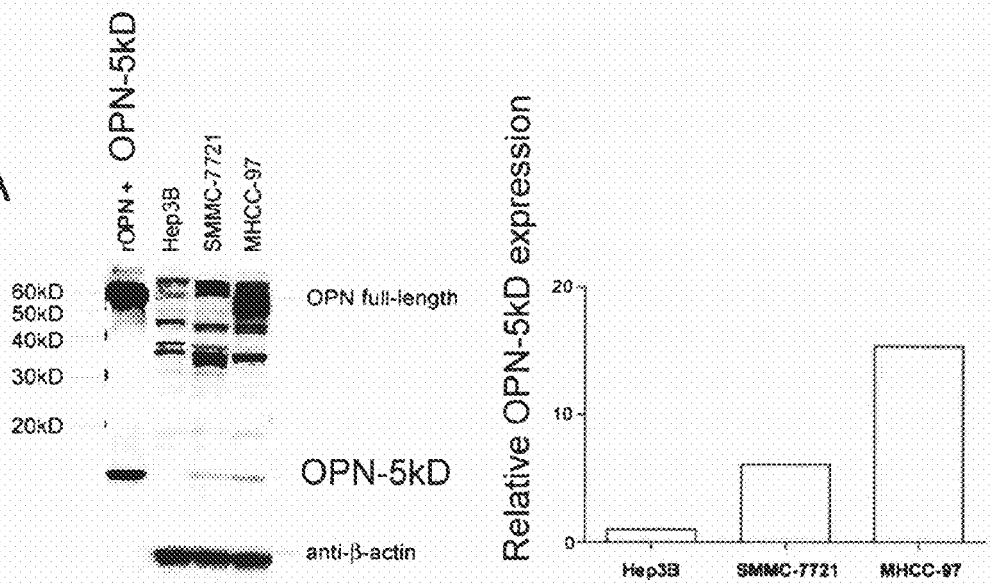
FIG. 4A is a digital image of a Western blot (left) and a bar graph showing densitometric analysis of OPN-5kD expression in FIG. 4A (right), demonstrating that endogenous OPN protein levels correlate with HCC cell line metastatic potential. Data were adjusted relative to Hep3B levels (=1) following normalization to beta-actin levels.

Total protein cell lysates (50 μg) were run by 16% SDS-PAGE, transferred to a nitrocellulose membrane, and probed with a polyclonal OPN antibody (pAb8448) and a monoclonal actin antibody (mAb1501). Recombinant human OPN and OPN-5kD peptide samples were run as controls (50 ng). As shown in FIG. 4A, endogenous OPN expression corresponds to degree of metastatic potential, with the highly-invasive cell line MHCC-97 expressing the most prominent levels. Similarly, relative levels of the OPN-5kD cleavage fragment correlated with metastatic potential (FIG. 4A, left panel and FIG. 4C). These results were reproduced using the OPN-5kD specific polyclonal antibody described in Example 8.

To determine the level of MMP-9 activity in the three human HCC cell lines (Hep3B, SMMC-7721, and MHCC-97), gelatinase activities in the cell lines were analyzed by zymography of conditioned media samples. Gelatin zymography was performed as follows. Cells were cultured for 48 hours in serum-free media. Cell number-adjusted serum-free conditioned media harvested from the HCC cell lines cultured to near-confluence were run on 10% tris-glycine gels containing 0.1% gelatin (NOVEX, Invitrogen, CA). The separated proteins were allowed to renature at 25° C. for 1 hour (2.5% Triton X-100) and develop at 37° C. for 16 hours (50 mM Tris, 0.2 M NaCl, 5 mM CaCl2, 0.02% Brij 35) followed by staining (0.1% amido black). Pro-MMP-9, active MMP-9, and active MMP-2 standards were included as controls (0.5 ug).

Figure 4B:
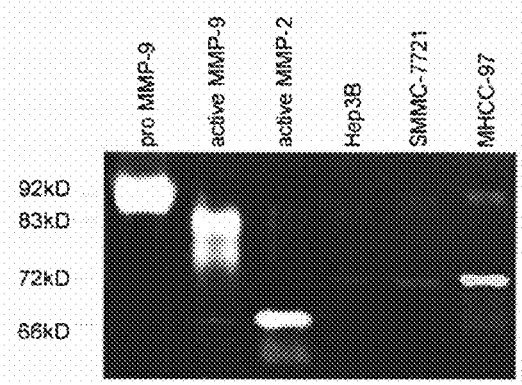
FIG. 4B is a digital image of a protein gel showing gelatinase activity relative to pro-MMP-9, active MMP-9, and active MMP-2 standards.
Figure 4C:
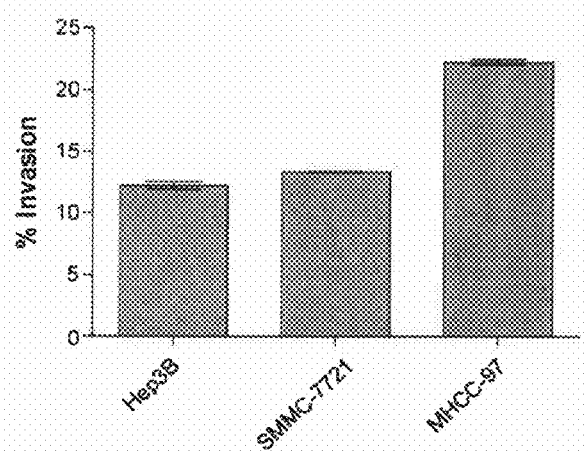
FIG. 4C is a bar graph showing the percent cell invasion for three HCC cell lines. Data are presented as the mean percent cell invasion and standard deviation following normalization to fluorescence readings corresponding to cells migrating through uncoated control membranes.

As shown in FIG. 4B, the highest levels of gelatinases (pro-MMP-9 and pro-MMP-2) were observed in MHCC-97 cell media. Conversely, the two low-metastatic cell lines, Hep3B and SMCC-7721, secreted nearly undetectable MMP-9 levels. These combined findings implicate a correlated MMP-9/OPN abundance which may confer differential levels of OPN-5kD.

To measure the invasion of HCC cell lines, the following methods were used. An equal number of cells ($5 \times 10^4$) was seeded into the upper chambers of Matrigel-coated 8-um pore membranes (HTSTM Fluoroblok tumor invasion system, BD Biosciences). After 36 hours, the invaded cells were labeled with calcein (37° C., 1 hour) and fluorescence was measured (EX485, EM530). As shown in FIG. 4C, the highest levels of invasion were observed in MHCC-97 cells, while the two low-metastatic cell lines, Hep3B and SMCC-7721, had lower levels of invasion.

Example 4

OPN Regions Differentially Modulate Cellular Adhesion and Migration

This example describes methods used to demonstrate the effects of OPN fragments on cellular adhesion and migration of HCC cells.

Cellular adhesion was measured using the following methods. SMMC-7721-SC2 cells were seeded into the wells of a 96-well fluorescent-read plate in serum-free media ($6 \times 10^4$ cells/well) with human OPN (0-250 nM) with or without prior digestion by MMP-9. Media and MMP-9 alone treated cells were included as controls. A GRGDS blocking peptide (400 μM) was added to separate media control, intact OPN, and MMP-9 cleaved OPN (250 nM) conditions. Non-adherent cells were removed with a PBS wash (100 μl) after one hour and adherent cells were quantified by CyQuant GR dye incorporation (Molecular Probes, OR) and detection at EX485, EM530.

Figure 5A:
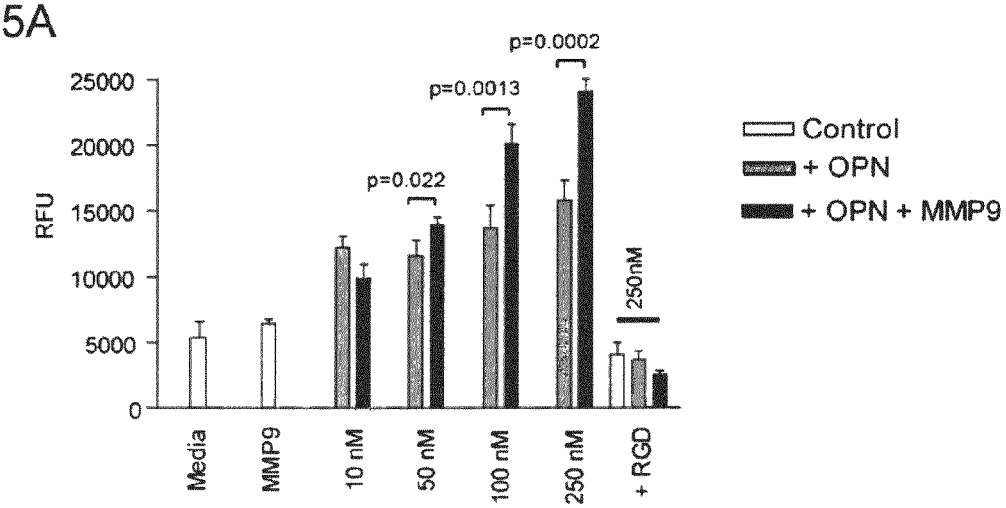
FIG. 5A is a bar graph showing that MMP-9-cleaved OPN increased HCC cell adhesion relative to uncleaved OPN. Student un-paired t-tests were used to compare cleaved versus un-cleaved OPN adhesion ($\alpha=0.05$).

As shown in FIG. 5A, increased SMMC-7721-SC2 adhesion was observed in the presence of an exogenous MMP-9 cleaved OPN pool versus intact OPN at >50 nM concentrations; addition of an integrin-binding GRGDS peptide blocked both intact and cleaved OPN-mediated adhesion.

To determine the affect of OPN fragments on adhesion, the following methods were used. SMMC-7721-SC2 cells ($1 \times 10^6$) were trypsinized (E-PET, Biosource, CA) and transfected with the four OPN expression constructs shown in FIG. 3A and empty vector DNA (5 μg) (50-60% efficiency) using optimized conditions (Nucleofection, AMAXA, MD) and plated to 6-well plates. After a 24-hour recovery period, the cells were trypsinized and seeded by equal numbers ($6 \times 10^4$) into fluorescent-read 96-well plates in serum-free media. Non-adherent cells were removed with a PBS wash after 2-60 minutes and fluorescence was quantified at EX485, EM530.

Figure 5B:
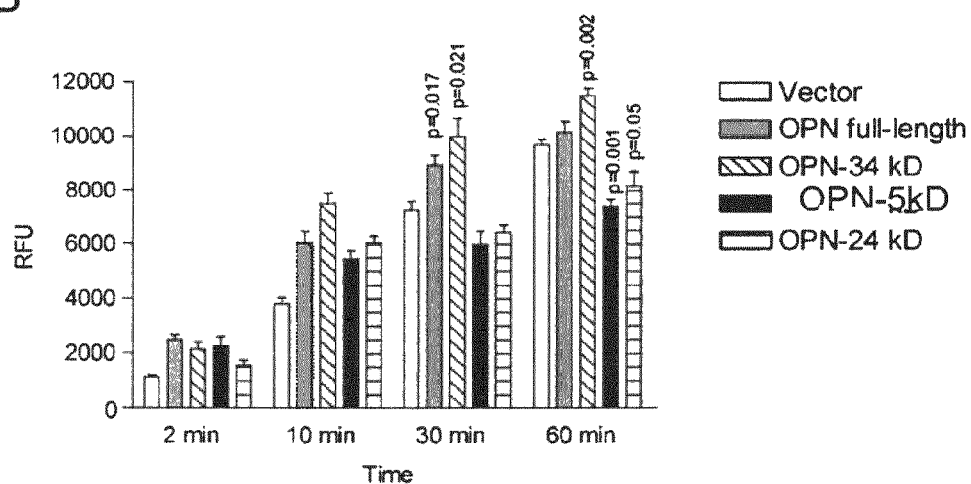
FIG. 5B is a bar graph showing adhesion of HCC cells in response to four OPN constructs. Student un-paired t-tests were used to compare media versus OPN adhesion at each time point ($\alpha=0.05$).

As shown in FIG. 5B, increased adhesion was observed in response to all four of the OPN constructs at early time points following transient over-expression (2-10 minutes). However, at later time points (30-60 minutes), the OPN fragments containing the RGD integrin binding motif (OPN-full-length and OPN-34kD) increased adhesion, whereas the non-RGD containing regions (OPN-5kD and OPN-24kD) decreased adhesion relative to controls (FIG. 5B).

Migration and invasion assays were performed as follows. Transfected SMMC-7721-SC2 cells (transfected with 5 μg plasmid DNA) were allowed to recover in 5% serum containing media and were re-counted prior to dilution in serum-free media. Cells were seeded ($5 \times 10^4$) into the upper chambers of Matrigel coated 8 um pore membranes (HTSTM Fluoroblok tumor invasion system, BD Biosciences, MA) or uncoated 0.8 um pore membranes (HTSTM Fluoroblok insert system, BD Biosciences, MA). Media containing serum (5%) was added to the lower chambers as a chemotactic agent. Blocking antibodies to either the integrin aV133 receptor (clone LM609, Chemicon, CA) or a common determinant of the CD44 receptors (clone A020, Calbiochem, CA) were added to the upper chambers (4 μg/ml) at the time of cell seeding. Migrated cells were labeled with calcein AM (Molecular Probes, OR) at 37° C. for 1 hour, and fluorescence was measured at 24, 36, and 48 hours (EX 490 nm, EM 530 nm).

Figure 5C:
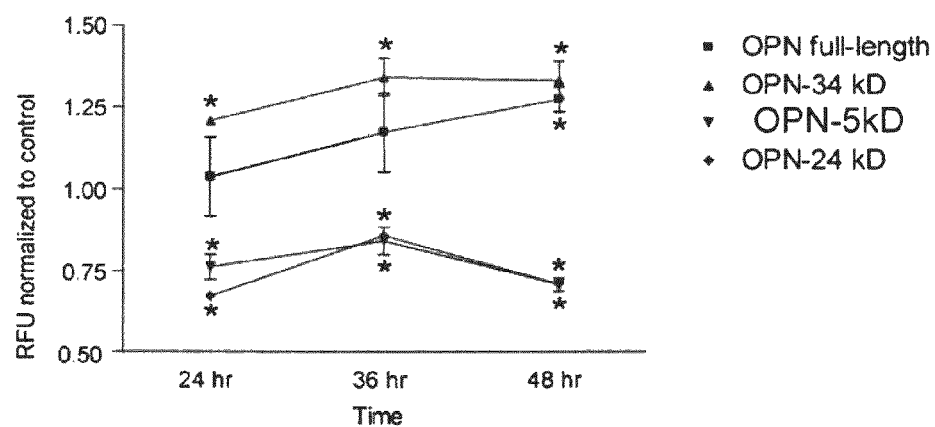
FIG. 5C is a graph showing the effect of different length OPN molecules on migration of SMMC-7721. Data are presented relative to vector-transfected cell controls at each of the time points. * denotes significance $p<0.017$.

As shown in FIG. 5C, full-length OPN and OPN-34kD induced SMMC-7721-SC2 migration whereas OPN-5kD and OPN-24kD expression decreased migration relative to controls.

Example 5

OPN-5kD Induces Cellular Invasion Via CD44, but not Integrin αVβ3, Receptors

This example describes methods used to determine the effect of OPN fragments on invasion of HCC cells.

Cell invasion was measured as described in Example 4. Briefly, each of the OPN vectors shown in FIG. 3A (5 μg) were separately transfected into SMMC-7721 cells ($1 \times 10^6$) using optimized conditions (Nucleofection, AMAXA). An equal number of cells ($5 \times 10^4$) was seeded into the upper chambers of Matrigel-coated 8 um pore membranes (HTSTM Fluoroblok tumor invasion system, BD Biosciences). After 36 hours, the invaded cells were labeled with calcein at 37° C. for 1 hour and fluorescence was measured (EX485, EM530).

Figure 6A:
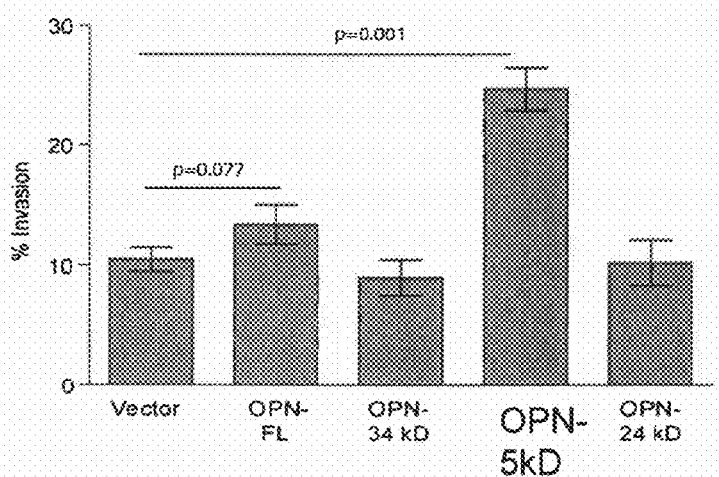
FIG. 6A is a bar graph showing that the OPN-5kD fragment induced reproducible increases in cellular invasion. Data are presented as the mean percent cell invasion and standard deviation following normalization to fluorescence readings corresponding to cells migrating through uncoated control membranes. Un-paired student's t-tests were used to compare mean and standard deviation values ($\alpha=0.05$).

As shown in FIG. 6A, only the internal OPN-5kD region of OPN induced reproducible >2-fold increases in cellular invasion in SMMC-7721-SC2 cells (p=0.001). Full-length OPN slightly increased invasion, but not to the extent observed by OPN-5kD. Conversely, over-expression of the RGD-containing OPN-34kD fragment slightly decreased invasiveness compared to vector transfected cells at 36 hours which was more noticeable at a longer 48 hour time point (p=0.005). No significant difference was observed with OPN-34kD or OPN-24kD.

To determine the effect of blocking antibodies to the integrin αVβ3 and CD44 receptors on the affect of invasion of HCC cells expression OPN full-length or OPN-5kD, integrin αVβ3 (Chemicon, CA) or CD44 (Calbiochem, CA) blocking antibodies were added (4 µg/ml) to cells transiently expressing OPN full-length and OPN-5kD. Invading cells were measured at 36 hours following calcein incorporation as described above.

To determine the effect of varying concentrations of the OPN-5kD peptide on invasion of HCC cells, SMMC-7721 cells were exposed to increasing concentrations of the OPN-5kD peptide (0.4 µM, 1 µM and 2 µM) and invading cells were measured after 36 hours following calcein incorporation as described above. A 44 residue peptide corresponding to the OPN-5kD fragment: LRSKSKKFRRPDIQYPDATDEDIT-SHMESEELNGAYKAIPVAQD (SEQ ID NO: 4), was synthesized and purified >97% by HPLC (EZBiolabs, IN). A GRADSP peptide of no known biological function was tested in parallel as a control. Cells transiently transfected with the OPN-5kD plasmid were included for comparison.

Figure 6B:
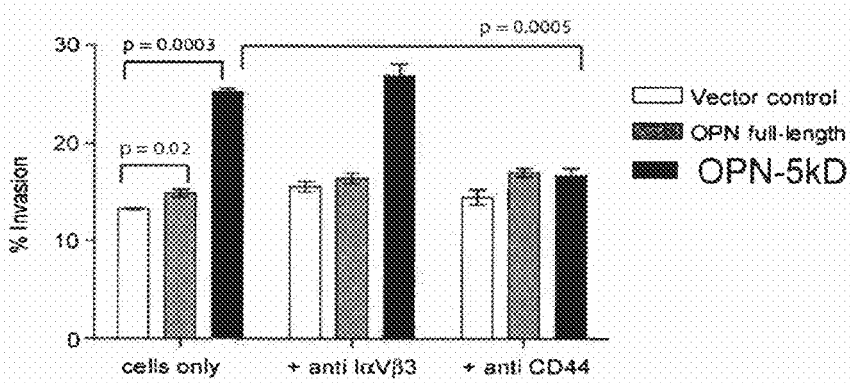
FIG. 6B is a bar graph showing the effect of the presence of blocking antibodies to the integrin $\alpha V\beta 3$ and CD44 receptors on the invasion of HCC cells transiently expressing OPN full-length or OPN-5kD. Un-paired student's t-tests were used to compare mean and standard deviation values ($\alpha=0.05$).
Figure 6C:
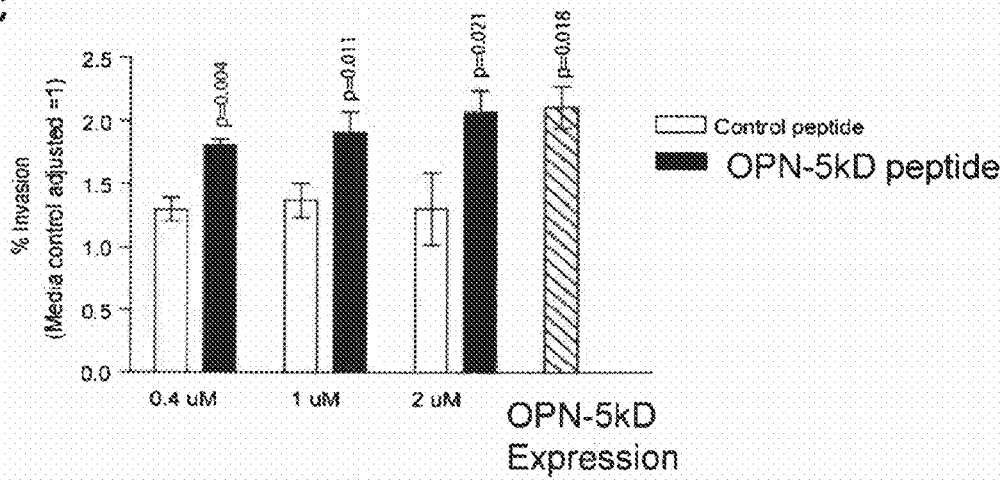
FIG. 6C is a bar graph showing the effect of varying concentrations of the OPN-5kD peptide on the invasion of HCC cells. Un-paired student's t-tests were used to compare mean and standard deviation values of media versus treated cells ($\alpha=0.05$).

As shown in FIG. 6B, addition of a blocking antibody that recognizes a common determinant of CD44 receptors significantly reduced OPN-5kD induced invasion (p=0.0005), whereas a blocking antibody to the integrin aV133 receptor had no significant effect. Similar results were observed when a synthetic peptide corresponding to OPN-5kD was used in a concentration-dependent manner (FIG. 6C).

These results indicate the OPN-5kD peptide induced cellular invasion is contingent upon CD44 receptor interaction. Similar patterns in adhesive, migratory, and invasive responses were reproduced in the other low-metastatic HCC cell line Hep3B.

Example 6

Fragments of OPN-5kD) Reduce OPN-5kD)-Induced Cellular Invasion

This example describes methods used to identify a minimum region responsible for the observed OPN-5kD-mediated cellular invasion and the identification of fragments that reduce OPN induced cellular invasion.

A 44 residue peptide corresponding to the OPN-5kD fragment (SEQ ID NO: 4), was synthesized and purified >97% by HPLC (EZBiolabs, IN). A series of short peptides spanning the region of residues 167-210 of OPN (SEQ ID NO: 2) were generated as follows. Eight small overlapping peptides spanning the OPN-5kD peptide were similarly synthesized to >75% purity (p1=LRSKSKKFRR, amino acids 167-176 of SEQ ID NO: 2; p2=KKFRRPDIQY, amino acids 172-181 of SEQ ID NO: 2; p3=PDIQYPDATD, amino acids 177-186 of SEQ ID NO: 2; p4=PDATDEDITS, amino acids 182-191 of SEQ ID NO: 2; p5=EDITSHMESE, amino acids 187-196 of SEQ ID NO: 2; p6=HMESEELNGA, amino acids 192-201 of SEQ ID NO: 2; p7=ELNGAYKAIP, amino acids 197-206 of SEQ ID NO: 2; and p8=YKAIPVAQD amino acids 202-210 of SEQ ID NO: 2) (EZBiolabs, IN). The lyophilized peptides were resuspended in PBS and applied with cells to the upper wells of Matrigel invasion chambers at equal molar concentrations (2 µM). Invading cells were measured after 36 hours following calcein incorporation as described in the examples above.

Exogenous treatment of these short peptides to SMMC-7721 SC2 cells at equal molar concentrations did not increase cellular invasion as compared to OPN-5kD or a control peptide of no known ability to bind cell surface receptors (GRADSP). However, three peptides (p3=PDIQYPDATD, SEQ ID NO: 5; p6=HMESEELNGA, SEQ ID NO: 6; and p7=ELNGAYKAIP, SEQ ID NO: 7) had a suppressive effect relative to media alone treated cells (p<0.05) (FIG. 7A).

Upon separate addition of p3, p6, and p7 in conjunction with OPN-5kD (1:1 molar concentrations, 2 µM each), a partial reduction in invasion was observed (p<0.002) which contrasted the insignificant effect of another peptide, p2 (FIG. 7B). The combined addition of p3, p6, and p7 completely abolished the OPN-5kD-mediated invasion down to the levels of media controls (p=2×10$^{-5}$).

Example 7

OPN-c is Highly Expressed in Metastatic HCC

This example describes methods used to identify the OPN splice variants expressed in HCC.

Quantitative RT-PCR was performed as follows. RNA was isolated from HCC primary metastatic tumors (n=17), primary non-metastatic tumors (n=T 5), and paired non-cancerous tissues collected >2 cm from the lesions, using Trizol (Invitrogen, CA). Normal liver tissue was used as a reference pool (n=8). Total RNA was quality assessed prior to reverse-transcription (cDNA archive kit, Applied Biosystems, CA). Primers were designed upstream and downstream from unique reporter sequences for OPN-a (TCTCCTAGCCCCA-CAGAATGCTGTG (25-mer, SEQ ID NO: 10), 66-bp final amplicon) and OPN-c (AGGAAAAGCAGAATGCTGT-GTCCTC (25-mer, SEQ ID NO: 11), 92-bp final amplicon) (TaqMan gene expression assays, Applied Biosystems, CA). CT threshold values were normalized to 18S rRNA (Applied Biosystems, CA) and data were presented as fold changes relative to the pooled normal liver samples.

Figure 8A:
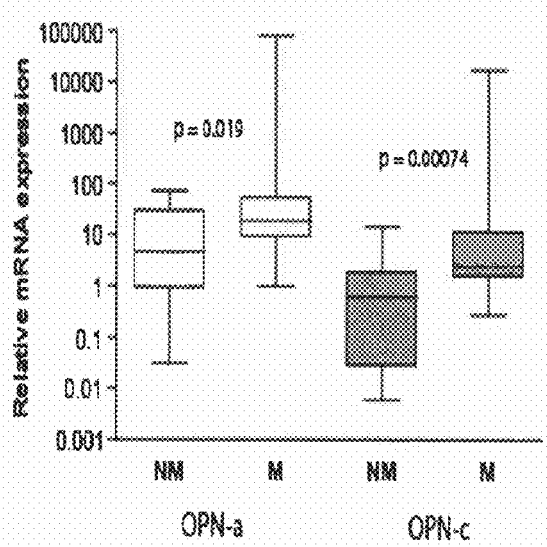
FIGS. 8A and 8B are plots showing the OPN splice variants expressed in (A) tumor or (B) non-cancerous tissue. Data are shown following normalization to 18S rRNA (Applied Biosystems, CA) and relative to a normal liver tissue reference pool (n=8).
Figure 8B:
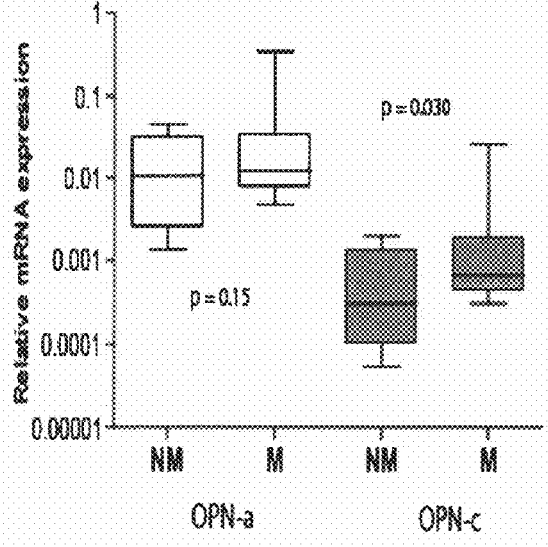

Increased mRNA levels corresponding to both the wild-type OPN-a and the variant OPN-c were detected in metastatic HCC tumor samples compared with non-metastatic HCC (FIG. 8A). This effect was notably greater for OPN-c (p=0.00074 vs. p=0.019 for OPN-a). Further, increased OPN-c levels were detected in non-cancerous tissue surrounding metastatic lesions but were not observed for OPN-a, indicating the involvement of the surrounding stroma in a differential expression of this OPN variant and conditions favoring metastasis (FIG. 8B). A similar difference in OPN-c transcript levels was reflected in the degree of metastatic potential in three highly metastatic HCC cell lines evaluated relative to two low-metastatic cell lines following normalization to primary hepatocytes.

These results indicate greater mRNA level expression of OPN-c than the wild-type OPN-a in metastatic HCC. The adjacent non-cancerous tissues of the metastatic tumor samples are also higher in OPN-c but not OPN-a levels. Histological analysis of this surrounding tissue indicates a predominance of Kupffer-like cells, likely indicating the contribution of macrophages in the tumor cell environment to this observed transcript level response. Thus, these results indicate a macrophage contribution to MMP-9 levels in the tumor cell microenvironment. Such tumor-stromal cell interactions

Example 8

Polyclonal Antibody Generation

This example describes methods used to generate polyclonal antibodies to the OPN-5kD peptide.

Un-conjugated OPN-5kD synthetic peptide (synthesized as described in Example 6) was injected into 2 rabbits (3×500 ug doses), followed by a boost injection (100 µg) at 84 days following initial immunization (Animal Pharm Services, CA). Post-boost bleedings were conducted every 2 weeks for 6 months and immuno-specific antibodies were affinity purified using an OPN-5kD peptide column (Affigel 15, Biorad, CA). The resulting IgG antibody was characterized using standard immunoblotting and immunoprecipitation methods.

Example 9

Monoclonal Antibody Generation

This example describes methods used to generate monoclonal antibodies to the OPN-5kD peptide.

Standard methods were used to produce monoclonal antibodies that were specific for OPN-5kD (for example see Harlow and Lane, *Antibodies: A Laboratory Manual*, Cold Spring Harbor Laboratory, New York, 1988). SEQ ID NO: 4 was injected into mice, followed by boost injections, to produce monoclonal antibodies. Murine hybridomas were produced. Antibody-producing clones were identified by detection of antibody in the supernatant fluid by Western blotting. One selected positive clone (5kd106-13D) was expanded and the monoclonal antibody product harvested.

Figure 9:
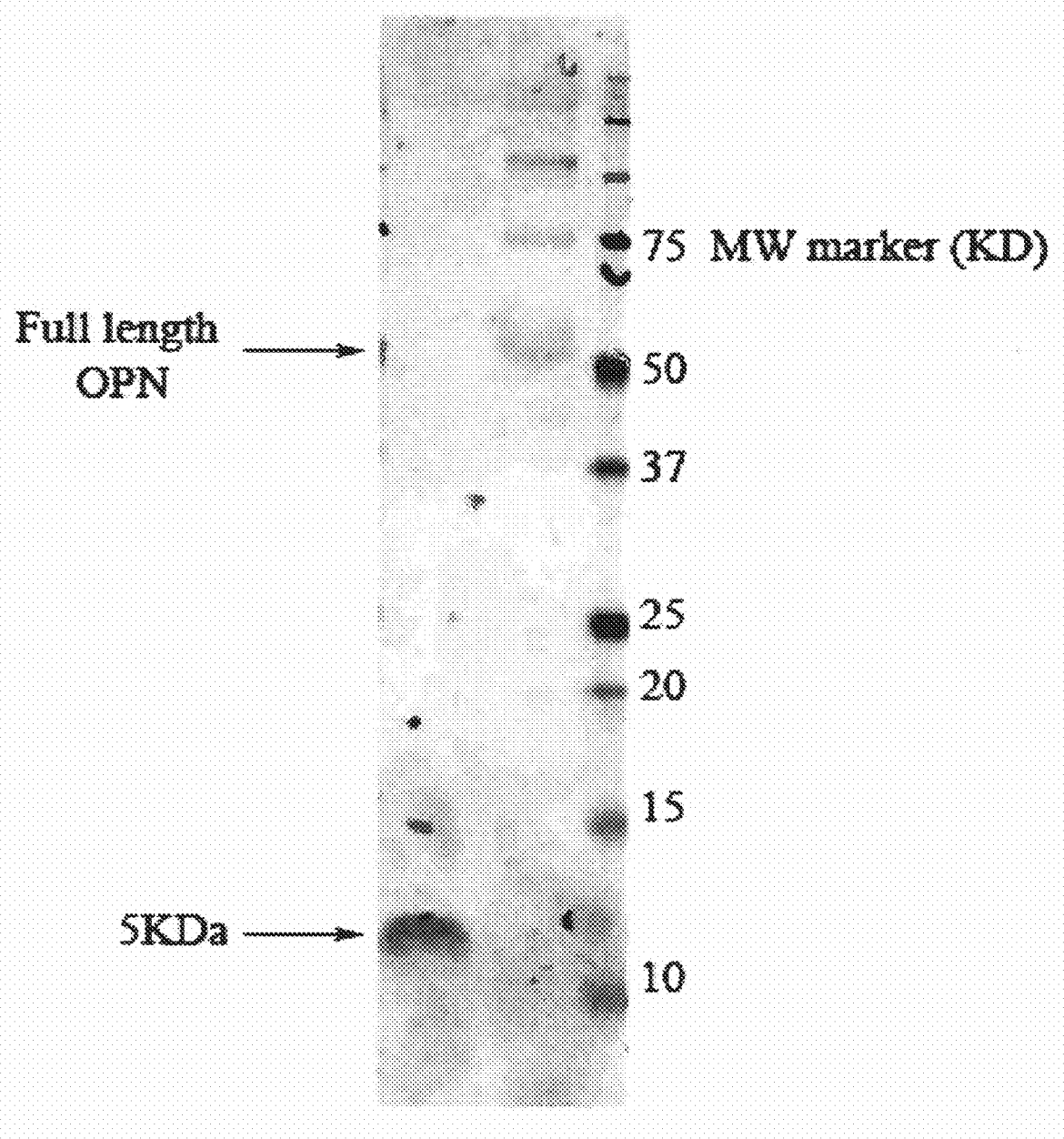
FIG. 9 is a digital image of a western blot showing detection of OPN-5kD with the monoclonal antibody 5kd106-13D.

Hybridoma 5kd106-13D had the highest specificity and sensitivity to binding the OPN-5kD fragment. As shown in FIG. 9, 5kd106-13D antibody detects the OPN-5kD fragment with high specificity, and also has some reactivity to full-length OPN. It is thought that full length OPN is bound to the blotting membrane in a manner that partially blocks access of the 5kd106-13D monoclonal antibody to the epitope within the OPN-5kD epitope sequence contained in the full length molecule.

The epitope of the monoclonal antibody produced by hybridoma 5kd106-13 D is EELNGAY (amino acids 30-36 of SEQ ID NO: 4).

Example 10

Humanization and Production of an scFv

This example provides methods that can be used to determine the CDR amino acid sequences of the monoclonal antibody 5kd106-13D described in Example 9. CDR amino acid sequences from monoclonal antibody 5kd106-13D are used for humanization and construction of recombinant scFv and scFv$_2$ fragments. Protein-based and cell-based assays have been used extensively for the purpose of evaluating engineered antibodies (reviewed by Qu et al., *Methods*. 36:84-95, 2005).

Competitive cell-based binding assays are developed to compare the antigen binding capabilities of engineered antibodies with those of the parental mouse monoclonal antibodies. For initial assays, human HCC cells are used as a source of target cells. For these assays, unlabeled engineered antibodies are used as a competitor of antigen binding by phycoerythrin (PE)-labeled parental antibodies. Briefly, human HCC cells are plated at $1\times10^5$ cells/well in a 96-well plate (100 uL/well). A constant amount of PE-labeled parental antibody (10 nM) is mixed with varying concentrations of unlabeled parental or engineered antibodies (0.2-1,000 nM) and added to each well (100 uL/well), with each experimental condition set up in triplicate. Plates are preblocked to prevent binding of PE-conjugated antibody to the plate surface (phosphate buffered saline (PBS), 0.05% Tween 20, and 5% fetal calf serum (FCS) for 2 hours at room temperature). After adding cells plus antibodies, the plates are incubated on ice with gentle mixing for 2 hr. Plates are then centrifuged and washed five times to eliminate unbound PE-labeled antibody and evaluated for PE signal using a fluorescence plate reader. The fluorescence associated with cells is plotted versus the concentration of unlabeled antibodies, yielding competitive inhibition curves. Successful engineering results in similar curves for the engineered and parental antibodies. Competitive radio-immunoassays can also be used as an alternative for this determination.

Example 11

Detection of OPN-5kD Using Antibodies

This example describes methods that can be used to detect the OPN-5kD fragment using OPN-5kD specific antibodies, such as those specific for the epitope EELNGAY (amino acids 30-36 of SEQ ID NO: 4), for example antibodies produced by hybridoma 5kd106-13D (see Example 9). For example, OPN-5kD can be detected in a biological sample, such as a tumor sample or blood sample (or fraction thereof) to facilitate disease diagnosis in patients not previously diagnosed with disease, confirmation of diagnosis in patients with tentative diagnosis, or disease monitoring in patients undergoing treatment for disease. In some examples, the levels of OPN-5kD are quantified. For example, such methods can be used to diagnose the presence of an OPN-expressing tumor, such as HCC or metastatic HCC, provide a prognosis of a subject having such a tumor (for example determine the likelihood that a patient will likely develop a metastasis), or combinations thereof.

In one example, serum specimens are evaluated from patients with HCC as well as normal subjects who do not have HCC or other cancer for the presence of the OPN-5kD fragment bound by monoclonal antibody 5kd106-13D (or other monoclonal antibody specific for the epitope EELNGAY, amino acids 30-36 of SEQ ID NO: 4). Serum specimens are evaluated from 20-50 HCC patients using Western blot analyses, direct ELISA, or sandwich ELISA. Antibody reactivity with serum specimens from normal donors (negative controls) is also assessed. Blood samples (10 mL) for preparation of serum is obtained and serum is aliquoted and stored at −80° C. until used. In some examples, serum is also analyzed for the presence of full-length OPN.

In some examples, full-length OPN (e.g., SEQ ID NO: 2) is removed from the serum prior to detection of OPN-5kD, for example using filtration to remove higher molecular weight proteins (e.g., full-length OPN) and allowing lower molecular weight proteins (e.g., OPN-5kD) to pass through. In some examples there is no fluid dilution factor so concentration of OPN-5kD in the filtrate is the same as it was in the unfractionated serum. For example, ultrafiltration methods can be used to physically separate the OPN-5kD fragment from OPN.

In some examples, competition ELISA is used to detect the OPN-5kD fragment in serum using an ultra sensitive electrochemiluminescence detection system. Competition assays are well-known in the art. In one example, the 5kd106-13D monoclonal antibody is used as the solid phase capture reagent and ruthenium-labeled OPN-5kD fragment as the equilibrium detection reagent. Addition of the serum or other test sample competes for the binding to the capture reagent. This results in a reduction of signal as unlabeled OPN-5kD fragment competes with the ruthenium-labeled OPN-5kD fragment. Ruthenium is caused to chemiluminesce by electrical current in the microtiter plate (e.g., provided by Meso Scale Discovery, Gaithersburg, Md.) and the resultant signal is measured (e.g., by CCD camera).

It is expected that the levels of the OPN-5kD fragment in serum from normal volunteers will be significantly decreased relative to patients with hepatocellular carcinoma (and conversely, the levels of the OPN-5kD fragment in serum from HCC patients will be significantly increased (for example at least 1.5-fold, at least 2-fold or even at least 5-fold) relative to normal patients), thus demonstrating the utility of monoclonal antibodies provided herein to diagnose or prognose an OPN-expressing tumor such as HCC.

Example 12

OPN-5kD Specific Antibodies Reduce OPN-5kD-Induced Cellular Invasion

This example describes methods that can be used to demonstrate that antibodies specific for OPN-5kD, such as those described in Examples 8 and 9 can inhibit cellular invasion in vitro.

OPN-5kD antibodies (e.g., 5kd106-13D or other antibody specific for the same epitope) are suspended in PBS and applied with cells to the upper wells of Matrigel invasion chambers at equal molar concentrations (2 µM). Invading cells are measured after 36 hours following calcein incorporation as described in the examples above (see Examples 4-6).

Therapeutic antibodies are identified as those that when added at equal molar amounts with OPN-5kD do not increase cellular invasion as compared to OPN-5kD (alone) or a control peptide of no known ability to bind cell surface receptors (GRADSP). Therapeutic antibodies are also identified as those that decrease migration as compared to the controls.

Example 13

Treatment of HCC in an Animal Model Using OPN5-kD Antibodies

This example describes methods than can be used to demonstrate that a therapeutic composition that includes one or more OPN-5kD specific antibodies can be used to treat HCC (such as metastatic HCC) in an animal model. One skilled in the art will appreciate that similar methods can be used to treat other OPN-overexpressing tumors.

Monoclonal OPN-5kD specific antibodies, such as those described in Example 9, for example 5kd106-13D or other monoclonal antibody specific for the epitope EELNGAY (amino acids 30-36 of SEQ ID NO: 4), will be effective in blocking the growth and invasiveness of HCC cancer cells in vivo. The effectiveness of such antibodies in blocking the growth of HCC tumors is tested using subcutaneous implantation of HCC tumor cells in mice as a model. The primary advantages of subcutaneous models are the ease of implantation and subsequent monitoring of tumor size. $5 \times 10^5$ HCC cells are inoculated subcutaneously into the right craniolateral thorax (axilla) using aseptic technique. Tumors are measured every 34 days using vernier calipers until they reach a volume of 0.2-0.3 cm$^3$. At that time, the mice are divided into four groups (8-10 animals each): Group 1 (vehicle control), Groups 2-4 are treated with 0.1, 1.0, or 10 mg/kg a particular test antibody (e.g., 5kd106-13D), administered intraperitoneally, twice a week. The mice are then monitored every 3 days to measure tumor volume (with vernier calipers), body weight, and life span. After no greater than 60 days past implantation, the animals are sacrificed and postmortem evaluations of tumorigenesis, including measurement and weight of implanted tumors and proximal lymph nodes, macroscopic evaluation of soft tissues for tumors (lymph nodes and lung), and formalin fixation of the primary tumor and tissues, are performed. The tissues are evaluated by immunohistochemistry using OPN specific antibodies to determine the level of OPN expression in the tumors. In particular, tumor cells that escape treatment are studied to determine whether they have low levels of OPN expression.

While subcutaneous implantation is a popular and valuable method for modeling tumor cell growth, differences between the microenvironment of the skin and liver can cause rather dramatic differences in cell behavior. For example, HCC may not metastasize when implanted subcutaneously whereas intrahepatic implantation (orthotopic) may facilitate metastasis. Thus, HCC cells are implanted in the liver by exposing the liver via laparotomy and inoculating tumor cells into liver using a surgical microscope. After seven days, the mice begin receiving treatment with antibody, as described above, and the animals are sacrificed no later than 60 days after implantation (or if the animals become moribund). The tumors are palpated at 3-5 day intervals, at which time data on tumor size, animal weight, and survival are collected. Post-mortem evaluations are also performed as described above, with emphasis upon the effect of antibody upon metastatic potential (to lungs and regional lymph nodes). The monoclonal antibodies are believed to block the primary tumor and metastatic potential of HCC cells in a dose-dependent manner.

To minimize identification of strain or clonal-specific effects, identical analyses using other model systems can be employed.

One skilled in the art will appreciate other models for liver cancer can be used, such as s.c. injection of MHCC97 cells with 100% penetrance to develop lung metastasis in 5 weeks in nude mice (see Ye et al., *Nat. Med.*, 10:416, 2003). OPN-5kD-specific antibodies are then administered and mice screened as described above. In some examples metastatic tumor cells are administered in the tail-vein injection and lung metastasis monitored.

Example 14

Treatment of HCC in an Animal Model

Using Fragments of OPN-5kD)

This example describes methods than can be used to demonstrate that a therapeutic composition that includes one or more OPN-5kD peptide fragments, such as a peptide 5 to 60 amino acids in length that has at least 5 contiguous amino acids of OPN-5kD (e.g., SEQ ID NO: 4), can be used to treat HCC (such as metastatic HCC) in an animal model. One skilled in the art will appreciate that similar methods can be used to treat other OPN-expressing tumors.

Mice recognized in the art as a model of HCC can be used. For example, the nude mice model LCI-D20 (see Tang et al., J. Cancer Res. Clin. Oncol. 130:187-96, 2004) or the model described in Ye et al. (*Nat. Med.,* 10:416, 2003) can be used. Mice are administered at least 1 μg of one or more OPN-5kD peptide fragments 5 to 60 amino acids in length having at least 5 contiguous amino acids of OPN-5kD (e.g., SEQ ID NO: 4), such as any of SEQ ID NOS: 5-8, intravenously or at least 100 μg (such as 1 mg) intramuscularly. These peptides can be formulated with an inert diluent or with a pharmaceutically acceptable carrier. If desired, other therapeutic molecules can also be administered, such as one or more anti-neoplastic agents. The therapeutic compositions can be administered in a single dose delivery, via continuous delivery over an extended time period, in a repeated administration protocol (for example, by a, daily, weekly, or monthly repeated administration protocol). In one example, mice receive at least weekly doses of the peptide over at least 6 months. Control mice can receive no peptide (such as an injection that only includes the pharmaceutical carrier).

Following the administration of one or more OPN-5kD peptide fragments, mice are monitored for tumor treatment, such as regression or reduction in metastatic lesions. In particular examples, mice are analyzed one or more times, starting 7 days following treatment. Mice can be monitored using any method known in the art. For example, diagnostic imaging can be used (such as x-rays, CT scans, MRIs, ultrasound,), as well as analysis of biological samples (for example analysis of blood, tissue biopsy, or other biological samples), such as analysis of the type of cells present, or analysis for a particular tumor marker.

A reduction in the number or size of tumors, or a prolonged survival time, in the experimental mice, as compared to the control mice, indicates that the one or more OPN-5kD peptide fragments have an anti-neoplastic therapeutic effect.

Example 15

Treatment of HCC in Humans with Anti-OPN-5kD) or Fragments of OPN-5kD)

This example describes particular methods that can be used to treat a primary or metastatic HCC tumor in humans by administration of (1) an antibody specific for OPN-5kD (such as 5kd106-13D or another monoclonal antibody that recognizes the same epitope), (2) one or more OPN-5kD peptide fragments, such as a peptide 5 to 60 amino acids in length that has at least 5 contiguous amino acids of OPN-5kD (e.g., SEQ ID NO: 4), or both (1) and (2). Although particular methods, dosages, and modes of administrations are provided, one skilled in the art will appreciate that variations can be made without substantially affecting the treatment. One skilled in the art will appreciate that similar methods can be used to treat other OPN-expressing tumors.

Therefore human patients are treated intravenously with at least 1 μg (such as 1-100 μg) of one or more peptides that include or consist of the sequence shown in any of SEQ ID NOS: 5-8, for example for a period of at least 6 months, at least one year, at least 2 years, or at least five years. Administration of the peptides can be used in conjunction with normal cancer therapy (for example rather than replacing the therapy). Thus the therapeutic peptides can be added to the usual and customary chemotherapy, surgery and/or radiation treatments conventionally used for the particular tumor type, such as HCC. Administration of the therapeutic peptides can be continued after chemotherapy and radiation therapy was stopped and can be taken long term (for example over a period of months or years).

Similarly, human patients are treated intravenously with at least 1 μg of 5kd106-13D (or a humanized form, chimeric form, or fragment thereof, or another monoclonal antibody that recognizes the same epitope), for example for a period of at least 6 months, at least one year, at least 2 years, or at least five years. Administration of the antibodies can be used in conjunction with normal cancer therapy (for example rather than replacing the therapy). Thus the therapeutic antibodies can be added to the usual and customary chemotherapy, surgery and/or radiation treatments conventionally used for the particular tumor type, such as HCC. Administration of the therapeutic antibodies can be continued after chemotherapy and radiation therapy was stopped and can be taken long term (for example over a period of months or years).

Briefly, the method can include screening subjects to determine if they have HCC, such as primary or metastatic HCC. Subjects having HCC are selected. In one example, subject having increased levels of the OPN-5kD fragment in their serum are selected. In a clinical trial, half of the subjects would follow the established protocol for treatment of HCC (such as a normal chemotherapy/radiotherapy/surgery regimen). The other half would follow the established protocol for treatment of the tumor (such as a normal chemotherapy/radiotherapy/surgery regimen) in combination with administration of the therapeutic peptides or antibodies described above. In some examples, the tumor is surgically excised (in whole or part) prior to treatment with the therapeutic peptides or antibodies.

Screening Subjects

In particular examples, the subject is first screened to determine if they have HCC. Examples of methods that can be used to screening for HCC include a combination of ultrasound, tissue biopsy, and examination of alpha-feta protein (AFP) levels, wherein serum AFP levels greater than 20 ng/ml or greater than 400 ng/ml and a positive imaging result indicate that the subject has HCC.

In some examples, the tumor is analyzed to determine if it overexpresses OPN, MMP-9, or both, wherein the presence of such overexpression indicates that the tumor can be treated with the disclosed therapies. For example serum can be screened for the presence of OPN-5kD, and the tumor can be screened for OPN-c (and in some examples also OPN-a) expression.

However, such pre-screening is not required prior to administration of the therapeutic peptides or antibodies described herein.

Pre-Treatment of Subjects

In particular examples, the subject is treated prior to administration of therapeutic peptides or antibodies described herein. However, such pre-treatment is not always required, and can be determined by a skilled clinician. For example, the tumor can be surgically excised (in total or in part) prior to administration of one or more therapeutic peptides or antibodies described herein. In addition, the subject can be treated with an established protocol for treatment of the particular tumor present (such as a normal chemotherapy/radiotherapy regimen).

Administration of Therapeutic Compositions

Administration can be achieved by any method known in the art, such as oral administration, inhalation, or inoculation (such as intramuscular, ip, or subcutaneous). In some examples, the therapeutic composition includes one or more of SEQ ID NOS: 5-7 or antibody 5kd106-13D (or a humanized form, chimeric form, or fragment thereof).

The amount of one or more therapeutic peptides or antibodies administered is sufficient to treat a subject having HCC. An effective amount can being readily determined by one skilled in the art, for example using routine trials establishing dose response curves. In addition, particular exemplary dosages are provided above. The therapeutic compositions can be administered in a single dose delivery, via continuous delivery over an extended time period, in a repeated administration protocol (for example, by a, daily, weekly, or monthly repeated administration protocol).

In one example, therapeutic compositions that include an antibody specific for OPN-5kD (such as 5kd106-13D or another monoclonal antibody that recognizes the same epitope) or one or more OPN-5kD peptide fragments, such as a peptide 5 to 60 amino acids in length that has at least 5 contiguous amino acids of OPN-5kD (e.g., SEQ ID NO: 4) are administered iv to a human. As such, these compositions may be formulated with an inert diluent or with an pharmaceutically acceptable carrier.

Assessment

Following the administration of one or more therapies, subjects having a tumor (for example HCC) can be monitored for tumor treatment, such as regression or reduction in metastatic lesions. In particular examples, subjects are analyzed one or more times, starting 7 days following treatment Subjects can be monitored using any method known in the art. For example, diagnostic imaging can be used (such as x-rays, CT scans, MRIs, ultrasound, fiberoptic examination, and laparoscopic examination), as well as analysis of biological samples from the subject (for example analysis of blood, tissue biopsy, or other biological samples), such as analysis of the type of cells present, or analysis for a particular tumor marker. In one example, if the subject has a metastatic HCC, assessment can be made using ultrasound, MRI, or CAT scans, analysis of the type of cells contained in a tissue biopsy, and AFP levels.

Example 16

Evaluation Following Treatment

During or following therapeutic treatment (such as that described in Example 15), subjects can be monitored for the response of their tumor(s) to the therapeutic peptides or antibodies.

Subjects can receive a complete physical evaluation, CBC, acute care, hepatic and mineral panels and appropriate evaluations of all evaluable lesions (for example by x-ray, MRI, CT scan, ultrasound) are obtained every 6-12 weeks during the first six months of therapy and if stable, every 3-6 months thereafter. Other evaluations can be performed as indicated by symptoms or physical findings. For example, surveillance CT of the chest, abdomen and pelvis can be obtained with at least every other assessment and as indicated by symptoms or physical findings.

Example 17

Additional Treatment

In particular examples, if subjects are stable or have a minor, mixed or partial response to treatment, they can be re-treated after re-evaluation with the same schedule and preparation of peptide or antibody that they previously received for up to a year of total therapy.

A mixed response is the shrinkage of some lesions but an increase in others. Subjects with mixed responses may only receive treatment for an additional 2-3 months without showing true disease stability or a bona fide minor or major response (i.e., no further progression). Two re-treatment cycles can be given following a complete response.

Example 18

Diagnosis of HCC in Humans

This example describes particular methods that can be used to diagnose or prognose HCC (such as metastatic HCC) in a human subject. However, one skilled in the art will appreciate that similar methods can be used. In some examples, such diagnosis is performed before treating the subject (for example as described in Example 15).

Biological samples are obtained from the subject. If blood or a fraction thereof (such as serum) is used 0.1-10 ml of blood is collected. Serum can either be used directly or fractionated using filter cut-offs to remove high molecular weight proteins (such as full-length OPN). If desired, the serum can be frozen and thawed before use. If a tissue biopsy sample is used, 1-100 µg of tissue is obtained, for example using a fine needle aspirate RNA is isolated from the tissue using routine methods (for example using a commercial kit).

In one example, OPN-5kD protein levels are determined in a serum sample obtained from the subject. The serum sample described above is incubated with the antibody described in Example 9 (5kd106-13D) for a time sufficient for the antibody to bind to OPN-5kD in the serum. The OPN-5kD/antibody complexes are detected, for example using an ELISA. Alternatively, the serum sample is subjected to 16% SDS-PAGE, and transferred to a membrane (such as nitrocellulose), which is probed with the 5kd106-13D antibody. The antibody/OPN-5kD complexes can be detected with a secondary labeled antibody, or by observing the appropriated sized protein on the gel. The relative amount of OPN-5kD/antibody complexes in the serum sample from the subject can be compared to a reference value, such as a relative amount of OPN-5kD/antibody complexes present in a serum sample from a subject not having a tumor, wherein the presence of significantly more OPN-5kD/antibody complexes in the test sample as compared to the reference sample (such as an increase of at least 2-fold, at least 3-fold, or at least 5-fold) indicates that the subject has HCC, has metastatic HCC, has a poor prognosis, or combinations thereof.

In one example, OPN-c mRNA expression levels are determined in a tumor sample obtained from the subject and in a tissue sample adjacent to (but not including) the tumor. cDNA is generated from the RNA isolated from the tissue samples described above (for example using a commercial reverse transcription kit). OPN-c cDNA is amplified using appropriate primers (for example using primers having a detectable label), and the resulting OPN-c amplicons detected. The relative amount of OPN-c amplicons in the tumor tissue sample can be compared to a reference value, such as a relative amount of OPN-c amplicons present in the adjacent non-tumor sample from the subject, wherein the presence of significantly more OPN-c amplicons in the tumor sample as compared to the non-tumor sample (such as an increase of at least 2-fold, at least 3-fold, or at least 5-fold) indicates that the subject has metastatic HCC, has an increased likelihood of a primary HCC metastasizing, has a poor prognosis, or combinations thereof.

In some examples, relative amount of OPN-5kD protein and OPN-c mRNA expression are determined in the same subject using the methods described above.

Example 19

Screening for Small Molecule Inhibitors

This example provides exemplary methods that can be used to identify small molecule inhibitors that mimic inhibition observed with OPN-5kD specific antibodies.

A binding assay that measures OPN-5kD binding to its antibody (such as 5dk106-13D), for example an ELISA, Western blot, or other immunoassay. Binding of the antibody to OPN-5kD is detected in the presence and absence of one or more test compounds. Such test compounds are commercially available or can be generated using routine methods. Small molecules that disrupt the binding between the antibody and the OPN-5kD fragment are candidate inhibitors of OPN-5kD, and thus may be used in the therapeutic methods provided herein. For example, such molecules may bind to the paratope of the antibody and hence block its ability to bind to the OPN-5kD fragment. Alternatively, the small molecule inhibitors can also bind to the OPN-5kD fragment and block the epitope of the antibody.

Molecules identified using the methods can be further analyzed for their inhibition of OPN-5kD activity, and the ability to treat an OPN-overexpressing tumor, for example inhibit or reduce metastasis of a tumor, for example using the methods described in Examples 12-15.

In view of the many possible embodiments to which the principles of the disclosed invention may be applied, it should be recognized that the illustrated embodiments are only examples of the invention and should not be taken as limiting the scope of the invention. Rather, the scope of the invention is defined by the following claims. We therefore claim as our invention all that comes within the scope and spirit of these claims.

We claim:

1. A method for reducing the growth an OPN-expressing tumor cell, comprising contacting the cell with a therapeutically effective amount of a composition comprising one or more peptides consisting of the amino acid sequence of SEQ ID NO: 5 or 7, thereby reducing the growth of the OPN-expressing tumor cell.

2. The method of claim 1, wherein the OPN-expressing tumor cell is in a subject that has an OPN-expressing tumor and the method is a method of treating the OPN-expressing tumor, and contacting the cell comprises administering to the subject a therapeutically effective amount of the composition, thereby treating the OPN-expressing tumor.

3. The method of claim 2, wherein the OPN-expressing tumor comprises hepatocellular carcinoma (HCC).

4. The method of claim 3, wherein the HCC is a metastasis.

5. The method of claim 4, wherein the metastasis is an intra-hepatic metastasis.

6. The method of claim 4, wherein the metastasis is an extra-hepatic metastasis.

7. The method of claim 2, wherein serum from the subject has detectable OPN-5kD fragment, wherein the tumor expresses a greater amount of OPN-c mRNA than OPN-a mRNA, or both.

8. The method of claim 2, wherein the method further comprises administering one or more additional therapeutic agents at a therapeutically effective amount to the subject.

9. The method of claim 2, further comprising determining whether the subject has significantly increased levels of an OPN-5kD fragment in its serum compared to a subject not having a tumor, wherein the presence of significantly increased levels of the OPN-5kD fragment in the serum indicates that the subject has an OPN-expressing tumor.

10. A composition comprising one or more peptides consisting of the amino acid sequence of SEQ ID NO: 5, 6, 7, or 8.

11. A kit, comprising:
the composition of claim 10; and
at least one anti-neoplastic agent.

12. The kit of claim 11 wherein the at least one anti-neoplastic agent comprises interleukin-2 (IL-2), interleukin-12 (IL-12), granulocyte-macrophage colony stimulating factor (GM-CSF), a chemotherapeutic agent, an antibody to cytotoxic T-lymphocyte antigen-4 (anti-CTLA-4), an adjuvant, or combinations thereof.

13. The kit of claim 11 wherein the at least one anti-neoplastic agent comprises a chemotherapeutic agent.

14. The composition of claim 10, wherein the composition comprises a peptide consisting of the amino acid sequence of SEQ ID NO: 5.

15. The composition of claim 10, wherein the composition comprises a peptide consisting of the amino acid sequence of SEQ ID NO: 6.

16. The composition of claim 10, wherein the composition comprises a peptide consisting of the amino acid sequence of SEQ ID NO: 7.

17. The composition of claim 10, wherein the composition comprises a peptide consisting of the amino acid sequence of SEQ ID NO: 8.

18. The composition of claim 10, wherein the composition comprises peptides consisting of the amino acid sequence of SEQ ID NOS: 5 and 7.

19. The composition of claim 10, wherein the composition comprises peptides consisting of the amino acid sequence of SEQ ID NOS: 5, 6 and 7.

20. The composition of claim 10, wherein the composition further comprises one or more pharmaceutically acceptable carriers.

21. The composition of claim 10, wherein the composition further comprises an anti-neoplastic agent, antibiotic, alkylating agent, antioxidant, or adjuvant.

22. The composition of claim 10, wherein the composition further comprises a chemotherapeutic agent.

23. The composition of claim 10, wherein the composition further comprises an antibody to cytotoxic T-lymphocyte antigen-4 (anti-CTLA-4).

24. The composition of claim 10, wherein the composition comprises 1-1000 μg of the one or more peptides.

25. The composition of claim 10, wherein the composition comprises 1-1000 μmg of the one or more peptides.

26. The method of claim 1, wherein the composition is administered subcutaneously.

27. A method for reducing growth of an OPN-expressing hepatocellular carcinoma (HCC) in a mammal, comprising:
administering to the mammal a therapeutically effective amount of a composition comprising one or more peptides consisting of the amino acid sequence of SEQ ID NO: 5 or 7, thereby reducing growth of the HCC.

28. The method of claim 27, wherein the mammal is a human.

29. The method of claim 27, wherein the composition comprises SEQ ID NO: 5.

30. The method of claim 26, wherein the composition comprises SEQ ID NO: 7.

31. The method of claim 26, wherein the composition is administered subcutaneously.

32. A method for reducing the invasiveness of an OPN-expressing hepatocellular carcinoma (HCC) metastasis in a mammal, comprising:
administering to the mammal a therapeutically effective amount of a composition comprising one or more peptides consisting of the amino acid sequence of SEQ ID NO: 5, 6, or 7, thereby reducing the invasiveness the HCC metastasis.

33. The method of claim 32, wherein the mammal is a human.

34. The method of claim 32, wherein the metastasis is an intra-hepatic metastasis.

35. The method of claim 32, wherein the metastasis is an extra-hepatic metastasis.

36. The method of claim 32, wherein the extra-hepatic metastasis is a lung metastasis.

37. The method of claim 32, wherein the composition comprises SEQ ID NO: 5.

38. The method of claim 32, wherein the composition comprises SEQ ID NO: 6.

39. The method of claim 32, wherein the composition comprises SEQ ID NO: 7.

40. The method of claim 32, wherein the composition comprises SEQ ID NO: 5, 6 and 7.

41. The method of claim 32, wherein the composition is administered subcutaneously.

42. A method for reducing the invasiveness of an OPN-expressing cancer in a mammal, comprising:
administering to the mammal a therapeutically effective amount of a composition comprising one or more peptides consisting of the amino acid sequence of SEQ ID NO: 5, 6, or 7, thereby reducing the invasiveness the cancer.

43. The method of claim 42, wherein the mammal is a human.

44. The method of claim 42, wherein the composition comprises SEQ ID NO: 5.

45. The method of claim 42, wherein the composition comprises SEQ ID NO: 6.

46. The method of claim 42, wherein the composition comprises SEQ ID NO: 7.

47. The method of claim 42, wherein the composition comprises SEQ ID NO: 5, 6 and 7.

48. The method of claim 42, wherein the composition is administered subcutaneously.

49. The method of claim 42, wherein the invasiveness of the OPN-expressing cancer is reduced by at least 10%.

50. The method of claim 2, wherein the subject is a mammal.

51. The method of claim 49, wherein the mammal is a human.

52. The method of claim 1, wherein the composition comprises SEQ ID NO: 5.

53. The method of claim 1, wherein the composition comprises SEQ ID NO: 7.

54. A method for reducing growth a tumor comprising OPN-expressing tumor cells in a mammal, comprising administering to the mammal a therapeutically effective amount of a composition comprising one or more peptides consisting of the amino acid sequence of SEQ ID NO: 5 or 7 thereby reducing the growth of the tumor in the mammal.

55. The method of claim 54, wherein the mammal is a human.

56. The method of claim 54, wherein the composition comprises SEQ ID NO: 5.

57. The method of claim 54, wherein the composition comprises SEQ ID NO: 7.

58. The method of claim 54, wherein the method further comprises administering one or more additional therapeutic agents at a therapeutically effective amount to the mammal.

59. The method of claim 54, further comprising determining whether the mammal has significantly increased levels of an OPN-5kD fragment in its serum compared to a mammal not having a tumor, wherein the presence of significantly increased levels of the OPN-5kD fragment in the serum indicates that the mammal has an OPN-expressing tumor.

60. The method of claim 54, wherein the composition is administered subcutaneously.

61. The method of claim 54, wherein growth of the tumor is reduced by at least 20%.

62. The method of claim 32, wherein the invasiveness of the HCC metastasis is reduced by at least 10%.

63. The method of claim 27, wherein growth of the HCC is reduced by at least 20%.

* * * * *

UNITED STATES PATENT AND TRADEMARK OFFICE
CERTIFICATE OF CORRECTION

| | |
|---|---|
| PATENT NO. | : 7,803,380 B2 |
| APPLICATION NO. | : 12/340211 |
| DATED | : September 28, 2010 |
| INVENTOR(S) | : Takafuji et al. |

It is certified that error appears in the above-identified patent and that said Letters Patent is hereby corrected as shown below:

In the Specification:

Column 9, line 63, "([99])" should read --(1991)--

Column 10, line 58, "Gln or H is for Asn;" should read --Gln or His for Asn;--

Column 10, lines 59-60, "Asn or Gln for H is;" should read --Asn or Gln for His;--

Column 13, line 62, "activity" should read --activity.--

Column 14, line 47, "SEQ ID NO: 4)." should read --SEQ ID NO: 4.--

Column 20, line 60, "receptor an stimulate" should read --receptor and stimulate--

Column 29, line 32, "(an in some" should read --(and in some--

Column 29, line 41, "Thus is some" should read --Thus in some--

Column 30, line 37, "indicates that the" should read --indicates the--

Column 30, line 45, "is has metastasized" should read --has metastasized--

Column 31, line 21, "is has metastasized" should read --has metastasized--

Column 40, line 56, "same effect or" should read --same effector--

Column 44, lines 62-63, "exemplary a magnetic" should read --exemplary magnetic--

Column 48, line 32, "aV133" should read --αVβ3--

Column 49, line 27, "aV133" should read --αVβ3--

Column 49, line 39, "OPN-5kD) Reduce" should read --OPN-5kD reduce--

Column 49, line 40, "OPN-5kD)-Induced Cellular Invasion" should read --OPN-5kD-induced cellular invasion--

Column 50, line 25, "(n=T 5)" should read --(n=15)--

Column 55, line 38, "Anti-OPN-5kD)" should read --Anti-OPN-5kD--

Column 55, line 39, "OPN-5kD)" should read --OPN-5kD--

Signed and Sealed this
Sixth Day of December, 2011

David J. Kappos
*Director of the United States Patent and Trademark Office*

CERTIFICATE OF CORRECTION (continued)
U.S. Pat. No. 7,803,380 B2

Column 58, line 27, "aspirate RNA" should read --aspirate. RNA--

In the Claims:

Column 69, claim 1, line 54, "the growth an" should read --the growth of an--

Column 71, claim 25, line 50, "1-1000 μmg" should read --1-1000 mg--